(12) United States Patent
Gellman et al.

(10) Patent No.: US 9,796,660 B2
(45) Date of Patent: *Oct. 24, 2017

(54) GAMMA AMINO ACID BUILDING BLOCKS

(71) Applicant: WISCONSIN ALUMNI RESEARCH FOUNDATION, Madison, WI (US)

(72) Inventors: Samuel Helmer Gellman, Madison, WI (US); Li Guo, Blue Bell, PA (US); Michael Giuliano, Derby, CT (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,306

(22) Filed: Jun. 6, 2016

(65) Prior Publication Data

US 2016/0280632 A1  Sep. 29, 2016

Related U.S. Application Data

(62) Division of application No. 14/166,007, filed on Jan. 28, 2014, now Pat. No. 9,382,291, which is a division of application No. 12/904,942, filed on Oct. 14, 2010, now Pat. No. 8,664,356.

(60) Provisional application No. 61/251,630, filed on Oct. 14, 2009.

(51) Int. Cl.

| | |
|---|---|
| *A61K 38/00* | (2006.01) |
| *C07C 205/44* | (2006.01) |
| *C07C 205/55* | (2006.01) |
| *C07C 233/48* | (2006.01) |
| *C07C 237/24* | (2006.01) |
| *C07C 271/24* | (2006.01) |
| *C07D 211/56* | (2006.01) |
| *C07D 211/60* | (2006.01) |
| *C07K 5/02* | (2006.01) |
| *C07C 201/12* | (2006.01) |
| *C07C 269/00* | (2006.01) |
| *C07C 271/66* | (2006.01) |
| *C07K 5/065* | (2006.01) |
| *C07K 5/107* | (2006.01) |
| *C07K 7/06* | (2006.01) |

(52) U.S. Cl.
CPC .......... *C07C 205/44* (2013.01); *C07C 201/12* (2013.01); *C07C 205/55* (2013.01); *C07C 233/48* (2013.01); *C07C 237/24* (2013.01); *C07C 269/00* (2013.01); *C07C 271/24* (2013.01); *C07C 271/66* (2013.01); *C07D 211/56* (2013.01); *C07D 211/60* (2013.01); *C07K 5/0205* (2013.01); *C07K 5/06078* (2013.01); *C07K 5/1016* (2013.01); *C07K 7/06* (2013.01); C07C 2601/08 (2017.05); C07C 2601/14 (2017.05)

(58) Field of Classification Search
None
See application file for complete search history.

(56) References Cited

U.S. PATENT DOCUMENTS

| | | | |
|---|---|---|---|
| 6,191,166 B1 | 2/2001 | Audia et al. | |
| 6,914,048 B2 | 7/2005 | Gellman et al. | |
| 6,958,384 B2 | 10/2005 | Gellman et al. | |
| 2003/0211999 A1 | 11/2003 | Gellman et al. | |
| 2004/0116654 A1 | 6/2004 | Gellman et al. | |
| 2007/0087404 A1 | 4/2007 | Stahl et al. | |
| 2008/0166388 A1 | 7/2008 | Palecek et al. | |
| 2010/0021344 A1 | 1/2010 | Gellman et al. | |

FOREIGN PATENT DOCUMENTS

WO  WO 2004/018644 A2  3/2004

OTHER PUBLICATIONS

Kessar & Kloetzel, Heterocyclic compounds. X. Hydrogenated derivatives of isoindole and 2-azaazulene from reductive cyclization of γ-nitro ketones, Journal of Organic Chemistry (1962), 27, 1314-17.*
Benatalah et al., Progress towards new conformationally constrained HIV-1 protease inhibitors, *European Journal of Medicinal Chemistry, Editions Scientifique Elsevier*, Paris, France, vol. 30, No. 11, Jan. 1, 1995, pp. 891-900.
Chi et al., Enantioselective Organocatalytic Michael Addition of Aldehydes to Nitroethylene: Efficient Access to (2-Amino Acids, *Journal of the American Chemical Society*, vol. 130. No. 17, 2008, pp. 5608-5609.
Comer et al., A Microreactor for Microwave-Assisted Capillary (Continuous Flow) Organic Synthesis, *Journal of the American Chemical Society* (2005), 127(22), 8160-8167.
Corse et al, Biosyntheses of penicillins. V. Substituted phenylacetic acid derivtives as penicillin precursors, *Journal of the American Chemical Society* (1948), 70, 2837-43.

(Continued)

*Primary Examiner* — Thomas S Heard
(74) *Attorney, Agent, or Firm* — Daniel A. Blasiole; Joseph T. Leone; DeWitt Ross & Stevens S.C.

(57) ABSTRACT

The invention provides compounds and methods, for example, to carry out organocatalytic Michael additions of aldehydes to cyclically constrained nitroethylene compounds catalyzed by a proline derivative to provide cyclically constrained α-substituted-γ-nitro-aldehydes. The reaction can be rendered enantioselective when a chiral pyrrolidine catalyst is used, allowing for Michael adducts in nearly optically pure form (e.g., 96 to >99% e.e.).
The Michael adducts can bear a single substituent or dual substituents adjacent to the carbonyl. The Michael adducts can be efficiently converted to cyclically constrained protected γ-amino acid residues, which are essential for systematic conformational studies of γ-peptide foldamers. New methods are also provided to prepare other γ-amino acids and peptides. These new building blocks can be used to prepare foldamers, such as α/γ-peptide foldamers, that adopt specific helical conformations in solution and in the solid state.

10 Claims, 5 Drawing Sheets
(1 of 5 Drawing Sheet(s) Filed in Color)

(56) References Cited

OTHER PUBLICATIONS

Garcia-Garcia et al., Catalytic Asymmetric Michael Reactions of Acetaldehyde, *Angew. Chem., Int. Ed.* 2008, 47, pp. 4719-4721.

Guo et al., Helix formation in preorganized beta/gamma-peptide foldamers: hydrogen-bond analogy to the alpha-helix without alpha-amino acid residues, *Journal of the American Chemical Society*, vol. 132, No. 23, Jun. 16, 2010, pp. 7868-7869.

Guo et al., Stereospecific Synthesis of Conformationally Constrained Gamma-Amino Acids: New Foldamer Building Blocks That Support Helical Secondary Structure, *Journal of the American Chemical Society*, vol. 131, No. 44, Oct. 20, 2009, pp. 16018-16020.

Hayashi et al., Asymmetric Michael Reaction of Acetaldehyde Cata-lyzed by Diphenylprolinol Silyl Ether, *Angew. Chem., Int. Ed.* 2008, 47, pp. 4722-4724.

Hoffmann-Emery et al., Efficient Synthesis of Novel NK1 Receptor Antagonists: Selective 1,4-Addition of Grignard Reagents to 6-Chloronicotinic Acid Derivatives, *Journal of Organic Chemistry*, vol. 71, No. 5, 2006, pp. 2000-2008.

International Search Report and Written Opinion by European Patent Office for PCT/US2010/052724 mailed Mar. 8, 2011, 16 pgs.

Nodes et al., Enantioselective Intramolecular Michael Addition of Nitronates Onto Conjugated Esters: Access to Cyclic Gamma-Amino Acids With Up to Three Stereocenters, *Journal of the American Chemical Society*, vol. 131, No. 44, Oct. 14, 2009, pp. 16016-16017.

Sharma et al., 12/10- and 11113-Mixed Helices in ∀/(- and ∃(-Hybrid Peptides Containing C-Linked Carbo-(-amino Acids with Alternating ∀- and ∃-Amino Acids, *Journal of the American Chemical Society*, vol. 128, No. 45, 2006, pp. 14657-14668.

Tilley et al., Analogs of Ac-CCK-7 incorporating dipeptide mimics in place of Met28-Gly29, *Journal of Medicinal Chemistry*, vol. 35, No. 21, Jan. 1, 1998, pp. 3774-3783.

Wiesner et al., Peptide Catalyzed Asymmetric Conjugate Addition Reactions of Aldehydes to Nitroethylene-A Convenient Entry into (2-Amino Acids, *Journal of the American Chemical Society.* vol. 130, No. 17, 2008, pp. 5610-5611.

Woll et al., Parallel Sheet Secondary Structure in 7-Peptides, *Journal of the American Chemical Society* vol. 123, No. 44, 2001, pp. 1107711078.

\* cited by examiner

GAMMA AMINO ACID BUILDING BLOCKS

RELATED APPLICATIONS

This application is a divisional of U.S. patent application Ser. No. 14/166,007, filed Jan. 28, 2014, which issued as U.S. Pat. No. 9,382,291 on Jul. 5, 2016, and which is a divisional of U.S. patent application Ser. No. 12/904,942, filed Oct. 14, 2010, which issued as U.S. Pat. No. 8,664,356 on Mar. 4, 2014, and which claims priority under 35 U.S.C. §119(e) to U.S. Provisional Patent Application No. 61/251,630, filed Oct. 14, 2009, all of which are incorporated herein by reference.

GOVERNMENT SUPPORT

This invention was made with government support under 0551920 awarded by the National Science Foundation. The government has certain rights in the invention.

BACKGROUND

Developing new and efficient asymmetric conjugate addition reactions for carbon-carbon bond formation is a challenging area of organic synthesis. Some recent work has focused on organocatalytic Michael addition of carbonyl compounds to nitroalkenes. Among these reactions, Michael addition of aldehydes to nitroalkenes is of particular interest because of the valuable synthetic intermediates that are generated. β-Aryl nitroalkenes have been the most common Michael acceptors. These Michael reactions provide, for example, α,β-disubstituted-γ-nitrobutyl aldehydes. Access to adducts that bear only a single substituent adjacent to a carbonyl is of interest because such adducts can be readily converted to $\gamma^2$-amino acids. $\gamma^2$-Amino acids are important building blocks for γ-peptide and heterogeneous backbone foldamers.

Oligomers constructed from n-amino acid residues ("β-peptides") or from combinations of α- and β-amino acid residues ("α/β-peptides") can adopt protein-like folding patterns. The conformational properties of these oligomers provide a basis for ongoing development of β- and α/β-peptides that display interesting functional properties. β-Amino acid residues can be endowed with higher intrinsic folding propensities than those of a residues by installation of cyclic constraints to limit backbone torsional mobility. This capacity for residue-based rigidification has proven to be important for both structure and function of β- and α/β-peptide foldamers. Analogous benefits might result from the use of constrained γ-amino acid residues in foldamers, however it is difficult to explore the use of constrained γ-amino acid residues in foldamers because only a few types of ring-containing γ-amino acids are known. The few cyclic γ residues examined to date have been found to promote sheet secondary structure, which contrasts with the helix-favoring effects of the most common cyclic β-residues.

Additionally, the challenges of preparing enantiomerically pure γ-amino acids has limited the study of γ-peptide foldamers to date. Some routes to enantioenriched $\gamma^2$-amino acids have been described but they typically involve specialized chiral auxiliaries. Chiral auxiliary routes are undesirable for preparing multigram quantities of protected $\gamma^2$-amino acids bearing the diverse side chain functionality necessary for foldamer research.

Accordingly, new methods for the synthesis of $\gamma^2$-amino acids would significantly aid the preparation and study of γ-peptide and heterogeneous backbone foldamers. Ring-containing γ-amino acids are also needed to further the study of peptide foldamers. New synthetic methods for the preparation of versatile adducts that can be converted to $\gamma^2$-amino acids, and new methods for the preparation of cyclically constrained γ-amino acid residues, would be of significant value to the research community.

SUMMARY

The invention provides compounds of Formula I:

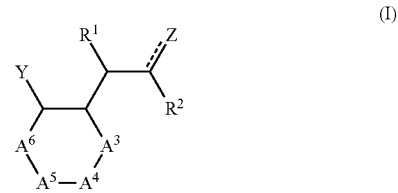

wherein
R$^1$ is hydrogen, alkyl, cycloalkyl, aryl, heteroaryl, or heterocycle;
R$^2$ is H, OH, an amino acid or peptide, or OR$^x$ wherein R$^x$ is alkyl, cycloalkyl, aryl, heteroaryl, heterocycle, or an oxygen protecting group;
Y is nitro, amino, —NHR$^y$, or —N(R$^y$)$_2$ wherein each R$^y$ is independently alkyl, cycloalkyl, aryl, heteroaryl, heterocycle, a nitrogen protecting group, or a nitrogen bonded to an amino acid;
Z is O, S, or H, and the dashed line to Z is an optionally present bond that is absent when Z is H;
A$^3$ is carbon;
A$^4$ is carbon or nitrogen;
A$^5$ is carbon, or nitrogen provided A$^6$ is not a direct bond;
A$^6$ is carbon or a direct bond;
each of A$^3$-A$^6$ are optionally substituted with one or two alkyl, alkoxy, fluoro, optionally protected hydroxy, aryl, (aryl)alkyl, heteroaryl, heterocycle, cycloalkyl, alkanoyl, alkoxycarbonyl, optionally protected amino, optionally protected aminoalkyl, optionally protected alkylamino, dialkylamino, acylamino, trifluoromethyl, trifluoromethoxy, optionally protected carboxy, optionally protected carboxyalkyl, keto, arylsulfonyl, cyano, or azide groups, or when nitrogen, one nitrogen protecting group; and
wherein each alkyl, cycloalkyl, aryl, heteroaryl, or heterocycle of any R$^1$, R$^2$, R$^x$, or R$^y$ is optionally substituted with one to five alkyl, alkoxy, fluoro, optionally protected hydroxy, aryl, (aryl)alkyl, heteroaryl, heterocycle, cycloalkyl, alkanoyl, alkoxycarbonyl, optionally protected amino, optionally protected aminoalkyl, optionally protected alkylamino, dialkylamino, alkylaminoalkyl, dialkylaminoalkyl, acylamino, trifluoromethyl, trifluoromethoxy, optionally protected carboxy, optionally protected carboxyalkyl, keto, arylsulfonyl, cyano, or azide groups;
or a salt or solvate thereof.

The invention also provides compounds of Formula IA:

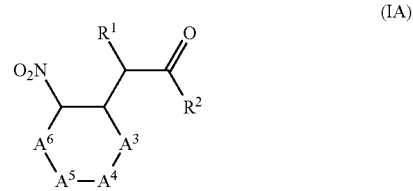

wherein

R$^1$ is hydrogen, alkyl, cycloalkyl, aryl, heteroaryl, or heterocycle; wherein the alkyl, cycloalkyl, aryl, heteroaryl, or heterocycle of R$^1$ is optionally substituted with one to five alkyl, alkoxy, fluoro, optionally protected hydroxy, aryl, (aryl)alkyl, heteroaryl, heterocycle, cycloalkyl, alkanoyl, alkoxycarbonyl, optionally protected amino, optionally protected aminoalkyl, optionally protected alkylamino, dialkylamino, alkylaminoalkyl, dialkylaminoalkyl, acylamino, trifluoromethyl, trifluoromethoxy, optionally protected carboxy, optionally protected carboxyalkyl, keto, arylsulfonyl, cyano, or azide groups;

R$^2$ is H, OH, an amino acid or peptide, or OR$^x$ wherein R$^x$ is alkyl, cycloalkyl, aryl, heteroaryl, or heterocycle; wherein the alkyl, cycloalkyl, aryl, heteroaryl, or heterocycle of R$^x$ is optionally substituted with one to five alkyl, alkoxy, fluoro, optionally protected hydroxy, aryl, (aryl)alkyl, heteroaryl, heterocycle, cycloalkyl, alkanoyl, alkoxycarbonyl, optionally protected amino, optionally protected aminoalkyl, optionally protected alkylamino, dialkylamino, alkylaminoalkyl, dialkylaminoalkyl, acylamino, trifluoromethyl, trifluoromethoxy, optionally protected carboxy, optionally protected carboxyalkyl, keto, arylsulfonyl, cyano, or azide groups;

A$^3$ is carbon;
A$^4$ is carbon or nitrogen;
A$^5$ is carbon, or nitrogen provided A$^6$ is not a direct bond;
A$^6$ is carbon, or a direct bond;
provided that only one or two of A$^3$-A$^6$ are nitrogen; and
each of A$^3$-A$^6$ are optionally substituted with one or two alkyl, alkoxy, fluoro, optionally protected hydroxy, aryl, (aryl)alkyl, heteroaryl, heterocycle, cycloalkyl, alkanoyl, alkoxycarbonyl, optionally protected amino, optionally protected aminoalkyl, optionally protected alkylamino, dialkylamino, acylamino, trifluoromethyl, trifluoromethoxy, optionally protected carboxy, optionally protected carboxyalkyl, keto, arylsulfonyl, cyano, or azide groups, or when nitrogen, one nitrogen protecting group; or a salt or solvate thereof.

The invention also provides compounds of Formula II:

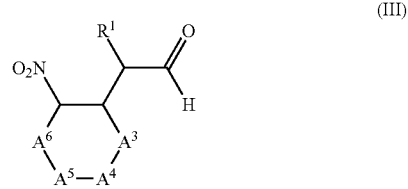

(II)

wherein

R$^1$ is hydrogen, alkyl, cycloalkyl, aryl, heteroaryl, or heterocycle; wherein the alkyl, cycloalkyl, aryl, heteroaryl, or heterocycle of R$^1$ is optionally substituted with one to five alkyl, alkoxy, halo, hydroxy, aryl, (aryl)alkyl, heteroaryl, heterocycle, cycloalkyl, alkanoyl, alkoxycarbonyl, amino, alkylamino, dialkylamino, acylamino, nitro, trifluoromethyl, trifluoromethoxy, carboxy, carboxyalkyl, keto, arylsulfonyl, cyano, or azide groups;

Y is nitro, amino, protected amino, or a nitrogen bonded to an amino acid;

R$^3$ is an amino acid side chain;

P is hydrogen, a carboxylic acid protecting group, or —OP is the nitrogen residue an amino acid or peptide;

A$^3$ is carbon or nitrogen;
A$^4$ is carbon or nitrogen;
A$^5$ is carbon or nitrogen;
A$^6$ is carbon, nitrogen, or a direct bond;
provided that only one or two of A$^3$-A$^6$ are nitrogen; and
each of A$^3$-A$^6$ are optionally substituted with one or two alkyl, alkoxy, halo, hydroxy, aryl, (aryl)alkyl, heteroaryl, heterocycle, cycloalkyl, alkanoyl, alkoxycarbonyl, amino, alkylamino, dialkylamino, acylamino, nitro, trifluoromethyl, trifluoromethoxy, carboxy, carboxyalkyl, keto, arylsulfonyl, cyano, or azide groups, or one nitrogen protecting group; or a salt or solvate thereof.

The invention further provides methods of preparing compounds of Formula I. The methods can include, for example, when R$^2$ is H, contacting a cyclic compound of 5 or 6 ring atoms that includes a nitroethylene moiety within the ring and that optionally includes one or two nitrogen atoms in the ring, wherein the carbon atoms in the ring are optionally substituted and the optional nitrogen atom or atoms in the ring are optionally substituted by a nitrogen protecting group; and an aldehyde that has at least one α-hydrogen; in the presence of an organic solvent, and a proline derivative, for a period of time sufficient to provide the compound of Formula I. Such compounds can be modified, for example, by oxidation, reduction, protection, and/or by conjugation to an amino acid or peptide, to provide other compounds, including other compounds of Formula I.

Additionally, the invention provides methods for preparing compounds of Formula III:

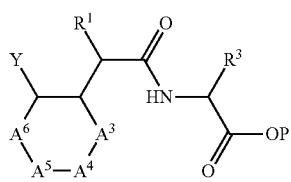

(III)

wherein

R$^1$ is hydrogen, alkyl, cycloalkyl, aryl, heteroaryl, or heterocycle; wherein the alkyl, cycloalkyl, aryl, heteroaryl, or heterocycle of R$^1$ is optionally substituted with one to five alkyl, alkoxy, halo, hydroxy, aryl, (aryl)alkyl, heteroaryl, heterocycle, cycloalkyl, alkanoyl, alkoxycarbonyl, amino, alkylamino, dialkylamino, acylamino, nitro, trifluoromethyl, trifluoromethoxy, carboxy, carboxyalkyl, keto, arylsulfonyl, cyano, or azide groups;

A$^3$ is carbon or nitrogen;
A$^4$ is carbon or nitrogen;
A$^5$ is carbon or nitrogen;
A$^6$ is carbon, nitrogen, or a direct bond;
provided that only one or two of A$^3$-A$^6$ are nitrogen; and
each of A$^3$-A$^6$ are optionally substituted with one or two alkyl, alkoxy, halo, hydroxy, aryl, (aryl)alkyl, heteroaryl, heterocycle, cycloalkyl, alkanoyl, alkoxycarbonyl, amino, alkylamino, dialkylamino, acylamino, nitro, trifluoromethyl, trifluoromethoxy, carboxy, carboxyalkyl, keto, arylsulfonyl, cyano, or azide groups, or one nitrogen protecting group;

comprising contacting:
a compound of Formula IV:

(IV)

wherein R$^1$ is as defined for Formula III; and
a cyclic compound of 5 or 6 ring atoms that includes a nitroethylene moiety within the ring and that optionally includes one or two nitrogen atoms in the ring, wherein the carbon atoms in the ring are optionally substituted and the optional nitrogen atom or atoms in the ring are optionally substituted by a nitrogen protecting group;

in the presence of an organic solvent and a proline derivative, for a period of time sufficient to provide the compound of Formula III. The aldehyde moiety of Formula III can be oxidized to a carboxylic acid moiety, which can be optionally protected by a carboxylic acid protecting group or coupled to an amino acid or peptide. Alternatively the aldehyde can be reduced to an alcohol, which can be optionally protected by a hydroxyl protecting group. Additionally, the nitro group of Formula III can be reduced to an amine, which can be optionally protected by a nitrogen protecting group, or coupled to an amino acid or peptide.

The invention further provides methods for preparing α-substituted-γ-amino acids that includes a ring moiety attached to the carbons β and γ to the carboxylic acid moiety of the α-substituted-γ-amino acid, and the ring includes 5 or 6 carbon atoms, wherein one or two of the ring carbon atoms are optionally replaced with one or two nitrogen atoms, wherein the nitrogen atom or atoms in the ring are optionally substituted by a nitrogen protecting group. In certain embodiments, the α-substituted-γ-amino acid is a compound of Formula I. The method can include contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has at least one α-hydrogen. The contacting can be, for example, in the presence of an organic solvent and a proline derivative or compound.

The duration of the reaction is a period of time sufficient to provide an α-substituted-γ-nitro-aldehyde that includes a ring moiety attached to the carbons β and γ to the aldehyde. The method can further include reducing the aldehyde of the α-substituted-γ-nitro-aldehyde to an alcohol. The method can also include oxidizing the aldehyde or alcohol to a carboxylic acid to provide an α-substituted-γ-nitro-acid. The method can also include reducing the nitro moiety of the α-substituted-γ-nitro-acid to an amine, to provide the α-substituted-γ-amino acid that includes a ring moiety attached to the carbons β and γ to the carboxylic acid moiety of the α-substituted-γ-amino acid.

The invention yet further provides methods for preparing amide compounds that include an α-substituted-γ-amino acid that includes a ring moiety attached to the carbons β and γ to the carboxylic acid moiety of the α-substituted-γ-amino acid, coupled to an α-amino acid, a β-amino acid, or a γ-amino acid. The methods can include contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has at least one α-hydrogen.

The contacting can be in the presence of an organic solvent and a proline derivative, for a period of time sufficient to provide an α-substituted-γ-nitro-aldehyde that includes a ring moiety attached to the carbons β and γ to the aldehyde. The reaction can also include reducing the aldehyde of the α-substituted-γ-nitro-aldehyde to an alcohol. The reaction can further include oxidizing the aldehyde or alcohol to a carboxylic acid to provide an α-substituted-γ-nitro-acid. The reaction can additionally include forming a peptide bond with the carboxylic acid and the nitrogen moiety of an α-amino acid, a β-amino acid, or a γ-amino acid. The α-amino acid, the β-amino acid, or the γ-amino acid may have a protected carboxylic acid group. The method can also include reducing the nitro moiety of the α-substituted-γ-nitro-acid to an amine.

The invention additionally provides methods for preparing a α-substituted-γ-nitro-aldehyde that includes a ring moiety attached to the carbons β and γ to the carboxylic acid moiety of the α-substituted-γ-amino acid. The method can include contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has an α-methylene group. The contacting can be in the presence of an organic solvent, such as an aryl solvent or a chloroalkane solvent. The contacting can also be in the presence of a proline compound, such as an (S)- or (R)-diphenyl-prolinol trialkyl silyl ether. The method can be carried out for a period of time sufficient to provide the α-substituted-γ-nitrobutyraldehyde wherein the α-substituted-γ-nitro-aldehyde that includes a ring moiety attached to the carbons and γ to the carboxylic acid moiety of the α-substituted-γ-amino acid. The method can be carried out using enantioselective or enantiospecific techniques such that the product is prepared in at least about 90% enantiomeric purity.

The invention further provides compounds of Formula V, and methods of preparing a compound of Formula V:

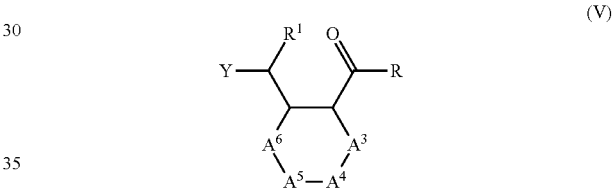

(V)

wherein
Y is $NO_2$ or $NH_2$;
R is H or OH;
$R^1$ is hydrogen, alkyl, cycloalkyl, aryl, heteroaryl, or heterocycle; wherein the alkyl, cycloalkyl, aryl, heteroaryl, or heterocycle of $R^1$ is optionally substituted with one to five alkyl, alkoxy, fluoro, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups;
$A^3$ is carbon;
$A^4$ is carbon or nitrogen;
$A^5$ is carbon, or nitrogen provided that $A^6$ is not a direct bond;
$A^6$ is carbon, or a direct bond; and
each of $A^3$-$A^6$ are optionally substituted with one or two alkyl, alkoxy, halo, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups, or one nitrogen protecting group; or a salt or solvate thereof. In various embodiments, Y of Formula V can also be defined as Y of Formula I, and R of Formula V can be defined as $R^2$ of Formula I.

To prepare compounds of Formula V where Y is nitro and R is H (i.e., a compound of Formula VI), the methods can include contacting a compound of a compound of Formula VII:

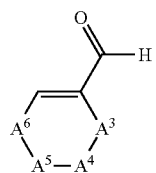

wherein $A^3$-$A^6$ are as defined for Formula V; and
a compound of Formula VIII:

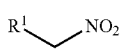

wherein $R^1$ is as defined for Formula V;

in the presence of an organic solvent and a proline derivative, for a period of time sufficient to provide the compound of Formula VI. The contacting can be carried out in the presence of a carboxylic acid, such as benzoic acid, and also optionally in the presence of a base, such as 2,4,6-collidine. The proline derivative can be a chiral pyrrolidine catalyst and the compound of Formula VI can be prepared in an enantiomerically enriched form. The chiral pyrrolidine catalyst can be, for example, an (S)- or (R)-diphenylprolinol trialkyl silyl ether. The organic solvent can be a ($C_1$-$C_4$) alcohol or a chloroalkane solvent. The aldehyde moiety of Formula VI (Formula V where R=H) can be oxidized to a carboxylic acid moiety (Formula V where R=OH), which can be optionally protected by a carboxylic acid protecting group or coupled to an amino acid or peptide. Alternatively the aldehyde can be reduced to an alcohol, which can be optionally protected by a hydroxyl protecting group. Additionally, the nitro group of Formula VI (Formula V where R=nitro) can be reduced to an amine (Formula V where R=amino), which can be optionally protected by a nitrogen protecting group, or coupled to an amino acid or peptide.

In another aspect, the invention provides a peptide that includes at least one γ-amino acid residue of Formula IX or Formula X;
where Formula IX is:

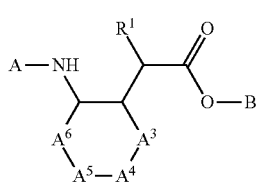

wherein
A is H, a nitrogen protecting group, an amino acid, or a chain of two or more amino acids;
B is H, a carboxylic acid protecting group, an amino acid, or a chain of two or more amino acids;
$R^1$ is hydrogen, alkyl, cycloalkyl, aryl, heteroaryl, or heterocycle, wherein the alkyl, cycloalkyl, aryl, heteroaryl, or heterocycle of $R^1$ is optionally substituted with one to five alkyl, alkoxy, fluoro, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups;
$A^3$-$A^6$ are as defined for Formula I;
and Formula X is:

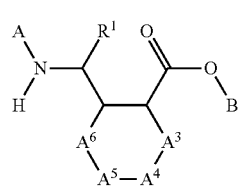

wherein
A is H, a nitrogen protecting group, an amino acid, or a chain of two or more amino acids;
B is H, a carboxylic acid protecting group, an amino acid, or a chain of two or more amino acids;
$R^1$ is alkyl, cycloalkyl, aryl, heteroaryl, heterocycle or optionally hydrogen (for example, when the peptide includes a moiety of Formula IX); wherein the alkyl, cycloalkyl, aryl, heteroaryl, or heterocycle of $R^1$ is optionally substituted with one to five alkyl, alkoxy, fluoro, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups; and
$A^3$-$A^6$ are as defined for Formula I.

In various embodiments, the peptide can include three or more residues and the peptide can form a 12-helix, a 13-helix, or a 14-helix. For example, the peptide can include alternating α- and γ-amino acid residues and thereby form a 12-helix. The peptide can also include one or more γαα peptide sequences thereby forming a 12-helix. The peptide can also include alternating β- and γ-amino acid residues thereby forming a 13-helix. The peptide can also include four or more contiguous γ-amino acid residues thereby forming a 14-helix. The peptide can include a variety of amino acids or amino acid chains, such as the various known natural and unnatural α-amino acids, as well as β-amino acids and/or other γ-amino acids, or combinations thereof. Examples of suitable amino acids and combinations thereof are described by, for example, U.S. Patent Publication Nos. 2004/0116654 (Gellman et al.), 2007/0087404 (Stahl et al.), 2008/0166388 (Palecek et al.), and 2010/0021344 (Gellman et al.), and U.S. Pat. No. 6,914,048 (Gellman et al.) and U.S. Pat. No. 6,958,384 (Gellman et al.), each of which is incorporated herein by reference.

The peptides of the invention can include conformationally constrained γ-amino acids and can be resistant or immune to peptidase and protease degradation. These peptides are therefore useful as tools to model peptide and protein conformations in aqueous solutions, and may be used as non-enzymatically degradable probes to mimic protein behavior in solution.

The invention further provides intermediates for the synthesis of the compounds and compounds of the Formulas described herein, such as the γ-amino acids and various corresponding peptides. Also provided are compounds that are valuable as intermediates for the synthesis of other useful compounds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIGS. 5A-5E illustrate exemplary peptides of the invention that contain one or more γ-amino acids, wherein α-amino acid residues are shaded in yellow, β-amino acid residues are shaded in blue, γ-amino acid residues are shaded in green, and hydrogen bonds are depicted with arrows. FIG. 5A illustrates a 1:1 α/γ-peptide having four 12-membered ring hydrogen bonds. FIG. 5B illustrates a 1:1 α/γ-peptide having four 12-membered ring hydrogen bonds. FIG. 5C illustrates a γαα-peptide having four 12-membered ring hydrogen bonds. FIG. 5D illustrates a 1:1 β/γ-peptide having three 13-membered ring hydrogen bonds.

DETAILED DESCRIPTION

Figure 1:
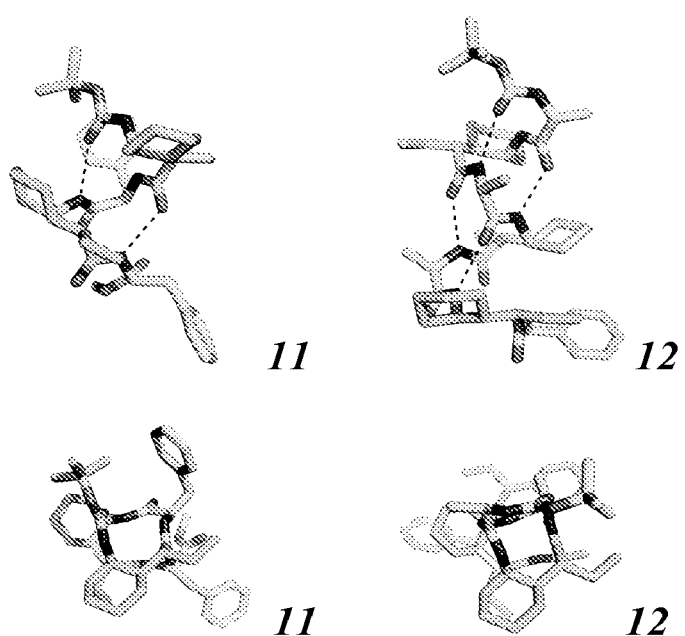
FIG. 1 illustrates crystal structures of 11 (left) and 12 (right) (see Scheme 5). Top views are perpendicular to the helical axis; bottom views are along the helical axis.
Figure 2:
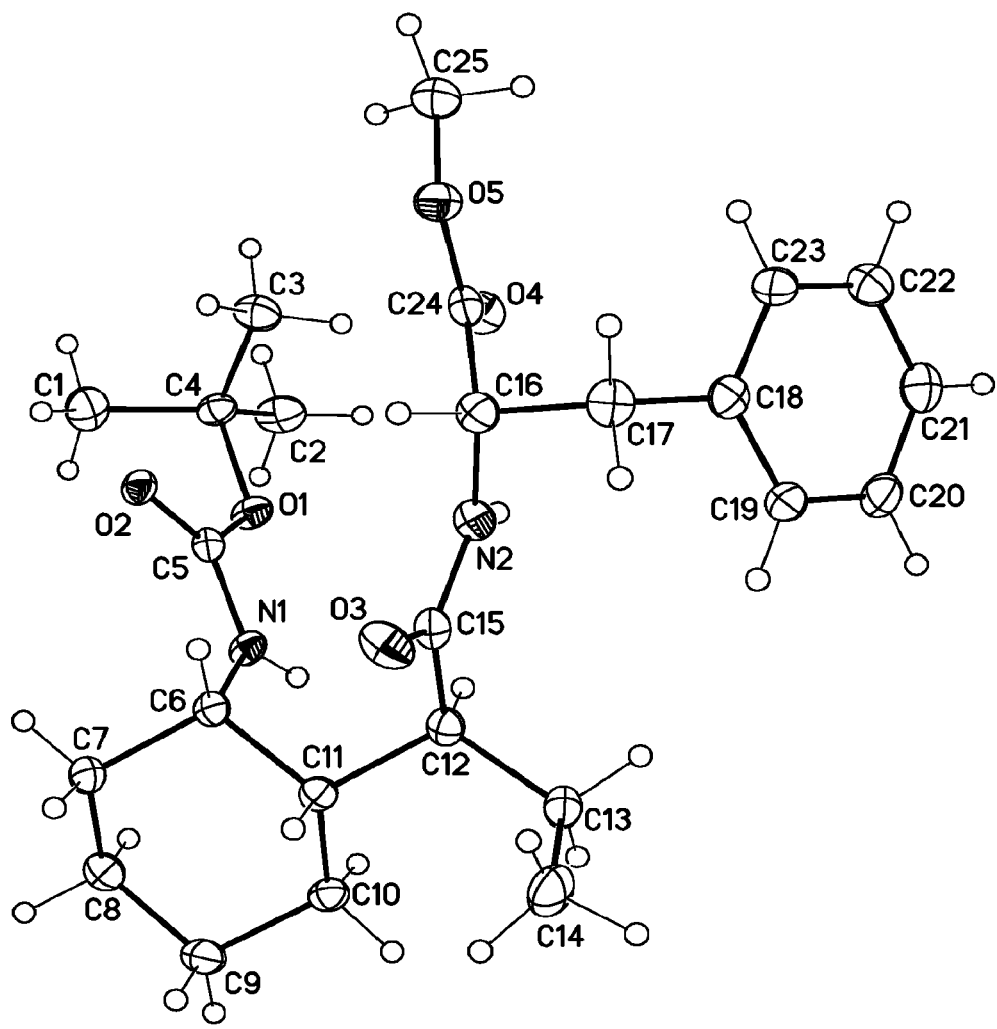
FIG. 2 illustrates the X-ray structure of the L-phenylalanine derivative of the major diastereomer 2a, which was determined to be (S,S,S).
Figure 2:
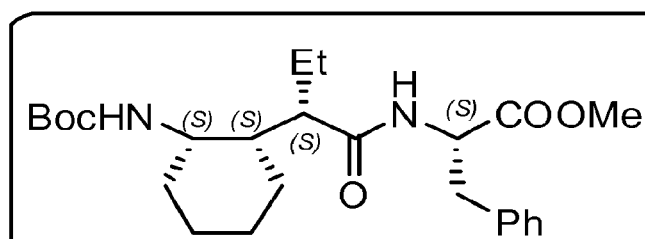
Figure 3:
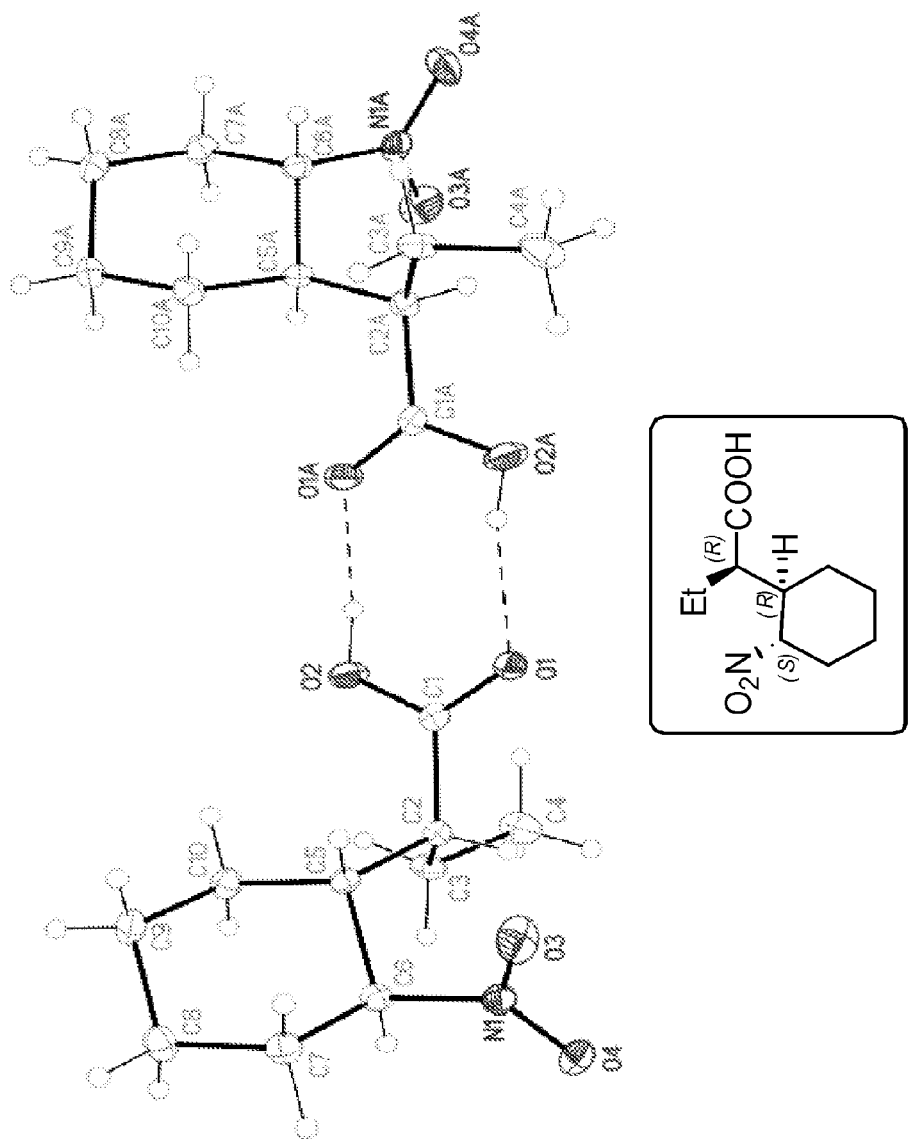
FIG. 3 illustrates the X-ray structure of the minor diastereomer (ent)-3a, prepared from Michael reaction catalyzed by 20 mol % (S)-A and 10 mol % m-nitrobenzoic acid, the absolute configuration of which was determined to be (S,R,R) by X-ray structure analysis of the corresponding nitro acid.

Gamma-amino acids are an important class of non-natural amino acids that are very difficult and/or expensive to prepare. Literature methods for making γ²-amino acids are limited, inefficient, and are not typically amenable to scalable synthesis or to creating structural diversity. These methods typically require about six synthetic steps and use harsh conditions that result in limited functional group tolerance, and low overall yields. They also typically require the separation of diasteriomers, which further reduces the synthetic efficiency of such methods.

The methods described herein allow for the preparation of cyclically constrained γ-amino acids using a Michael addition reaction. The Michael addition reaction is highly enantioselective, high yields are achieved, and the methods are amenable to large scale synthesis. The reaction conditions are mild, and are thus tolerant of a diverse range of functional groups. The starting materials, including the catalyst, are typically readily available and inexpensive. Accordingly, the invention provides flexible and efficient catalytic methods for the preparation of, for example, cyclically constrained amino aldehydes and γ²-amino acids. The methods can provide either the (R)- or (S)-enantiomer of the Michael adduct.

Thus, a highly stereoselective synthesis of novel cyclically constrained γ-amino acid residues is provided by the disclosure herein. The methods can include organocatalytic Michael addition of an aldehyde to a 1-nitrocycloalkene, such as an optionally substituted 1-nitrocyclohexene. After aldehyde reduction, this approach can provide optically active β-substituted-δ-nitro alcohols (96-99% e.e.), which can be converted to γ-amino acid amino acid residues with a variety of substituents at the α-position. These new building blocks can be used to prepare α/γ-peptide foldamers that adopt specific helical conformations in solution and in the solid state (e.g., as schematically illustrated in Scheme A).

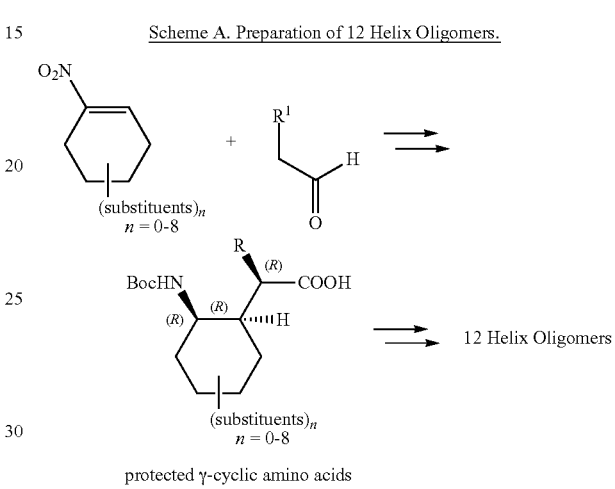

Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude certain optional elements. As such, this statement is intended to serve as antecedent basis for use of such exclusive terminology as "solely," "only," and the like in connection with the recitation of claim elements, or use of a "negative" limitation, which may be used to further described embodiments of the invention.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by one skilled in the art, for any and all purposes, particularly in terms of providing a written description, all ranges disclosed herein also encompass any and all possible subranges and combinations of subranges thereof as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, tenths, etc. As a non limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for various embodiments, the invention encompasses not only the main group, but also the main group absent one or more of the group members. The invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction, or a physical change, e.g., in a solution or in a reaction mixture.

An "effective amount" refers to an amount of a chemical or reagent effective to facilitate a chemical reaction between two or more reaction components, and/or to bring about a recited effect. Thus, an "effective amount" generally means an amount that provides the desired effect.

The term "α-substituted-γ-nitro-aldehyde" refers to a compound of the formula $O_2N—CHX^1—CHX^2—CH(R)—CHO$, where $X^1$ and $X^2$ together with the carbon atoms to which they are attached for an optionally substituted 5 or 6 membered carbocyclic ring or a 5 or 6 membered heterocyclic ring that includes one or two nitrogen atoms in the ring, wherein the nitrogen atom or atoms are optionally substituted by a substituent as described herein or by a nitrogen protecting group, and where the substituent R is considered to be 'alpha' to the aldehyde moiety. The group R can be any organic group or functional group, such as an optionally substituted alkyl group, an optionally protected amino acid or derivative thereof, and/or a substituent as described herein. The term α-substituted-γ-nitro-aldehyde can also refer to a compound of the formula $O_2N—CHX^1—CHX^2—C(R)(R)—CHO$, wherein the compound has two substituents 'alpha' to the aldehyde moiety, and $X^1$ and $X^2$ are as previously described.

The aldehydes useful for the reactions described herein have at least one α-hydrogen atom. Accordingly, the aldehydes employed with have either an α-methylene group or an α-methine group. An "aldehyde that has an α-methylene group" refers to a compound that includes a moiety of the formula $—CH_2—CHO$, and an "aldehyde that has an α-methine group" refers to a compound that includes a moiety of the formula $>CH—CHO$.

The term "proline derivative" refers to L-proline, R-proline, or a chemical derivative thereof. Such derivatives include various pyrrolidine compounds, including certain chiral pyrrolidine catalyst known in the art, for example, a proline compounds with one or more substituents on the pyrrolidine ring. Examples of proline derivatives include diarylprolinol trialkyl silyl ethers, such as diphenylprolinol trialkyl silyl ether, for example, diphenylprolinol trimethyl silyl ether. A proline derivative can be racemic, scalemic, or the derivative can be the (R) or (S) enantiomer.

The term "solvent" refers to any liquid that can dissolve a compound to form a solution. Solvents include water and various organic solvents, such as hydrocarbon solvents, for example, alkanes and aryl solvents, as well as chloroalkane solvents. Examples include hexanes, DMF, DMA, DMSO, benzene, toluene, xylenes, chloroform, methylene chloride, dichloroethane, and alcoholic solvents such as methanol, ethanol, propanol, isopropanol, and linear or branched (sec or tert) butanol.

A "reducing agent" can effectuate the removal of oxygen from a compound or the addition of hydrogen to a compound. Typical reducing agents include various hydride reagents, such as borohydride reagents and aluminum hydride reagents, for example, sodium borohydride and lithium aluminum hydride.

An "oxidizing agent" can effectuate the addition of oxygen to a compound or the removal of hydrogen from a compound. Typical reducing agents include various metal oxides and metal catalysts (e.g., a transition metal, optionally adsorbed onto carbon) in the presence of hydrogen gas. Examples include chromium oxides, such as the Jones reagent, and palladium on carbon in the presence of hydrogen gas.

The term "enantiomerically enriched" refers to mixtures that have one enantiomer present to a greater extent than another. In one embodiment, the term "enantiomerically enriched" refers to a mixture having at least about 50% enantiomeric excess ("ee"). In other embodiments, enantiomerically enriched can refer to a mixture having at least about 75% ee; at least about 80%; at least about 85%; at least about 90%; at least about 92%; at least about 95%; or at least about 98%. In another embodiment, the term "enantiomerically enriched" refers to a mixture having at least about 99% ee. The term "enantiomerically enriched" includes enantiomerically pure mixtures, which are mixtures that are substantially free of the species of the opposite optical activity or one enantiomer is present in very low quantities, for example, about 0.01%, about 0.001% or about 0.0001%.

Specific values listed below for radicals, substituents, and ranges, are for illustration only; they do not exclude other defined values or other values within defined ranges for the radicals and substituents.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene). In some embodiments, certain alkyl groups can be excluded from a definition. For example, in some embodiments, methyl, ethyl, propyl, butyl, or a combination thereof, can be excluded from a specific definition of alkyl in an embodiment.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more hetoeroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or —$(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine, where the point of attachment can be at any atom accessible by known synthetic methods.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

As to any of the above groups, which contain one or more substituents, it is understood, of course, that such groups do not contain any substitution or substitution patterns that are sterically impractical and/or are synthetically non-feasible. It will be appreciated that the compounds of the invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Reference to any of the compounds of the invention also refers to their salt or solvate, for example, hydrate. Examples of salts of the compounds can include salts derived from an appropriate base, such as an alkali metal (for example, sodium or potassium), an alkaline earth (for example, calcium or magnesium), ammonium or NX$_4^+$ (wherein X is, e.g., C$_1$-C$_4$ alkyl). Salts of a hydrogen group or an amino group include salts of organic carboxylic acids such as acetic, behenic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Salts of a compound of a hydroxy group (e.g., of a carboxylic acid) include the anion of the compound in combination with a suitable cation such as Na⁺ or NX$_4^+$ (where each X is independently selected from H or a C$_1$-C$_4$ alkyl group).

The term "amino acid" refers to a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, or Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; or tert-butylglycine) residue having one or more open valences. The term also includes β-amino acids and γ-amino acids. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a (C$_1$-C$_6$)alkyl, phenyl or benzyl ester, or amide). Other suitable amino and carboxy protecting groups are known to those skilled in the art (see for example, T. W. Greene, *Protecting Groups In Organic Synthesis*; Wiley: New York, Third Edition, 1999, and references cited therein; D. Voet, *Biochemistry*, Wiley: New York, 1990; L. Stryer, *Biochemistry*, (3rd Ed.), W. H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein).

The term "peptide" refers to any two or more amino acids linked by an amide (peptide) bond. The amino acid residues of the peptide can be α-amino acid residues, β-amino acid residues, and/or γ-amino acid residues. A "homogeneous peptide" refers to a peptide that includes only one type (e.g., α-, β-, or γ-residues) of amino acid. A "heterogeneous peptide" refers to a peptide that includes two or more of an α-amino acid residue, a β-amino acid residue, and a γ-amino acid residue. Examples of heterogeneous peptides include, for example, α/β-peptides, β/γ-peptides, α/γ-peptides, and α/β/γ-peptides, wherein the amino acid residues can be in any order. The term peptide includes dipeptides and chains of amino acids that include three or more residues. As such, the term peptide includes the term oligopeptide and polyamino acid.

The term "protecting group" refers to a group that, when bound to a hydroxyl, nitrogen, or other heteroatom, prevents undesired reactions from occurring at this group and which can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. For additional information on protecting groups, see also Kocienski, Philip J.; *Protecting Groups* (Georg Thieme Verlag Stuttgart, New York, 1994), which is incorporated herein by reference. Some specific protecting groups that can be employed in conjunction with the methods of the invention are discussed below.

Typical nitrogen protecting groups described in Greene (pages 14-118) include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy) ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-polybenzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate (mesylate), benzenesulfonate, benzylsulfonate, tosylate, or triflate).

The protecting groups used for the amino acids described herein can be nitrogen protecting groups or carboxylic acid protecting groups, e.g., amino-terminus protecting groups or carboxy-terminus protecting groups, respectively. The terms "amino-terminus protecting group" and "carboxy-terminus protecting group" are synonymous with such terms as "N-terminal capping group" and "C-terminal capping group," respectively. A variety of suitable protecting and capping groups, in addition to those described above, are known in the art. Various types of amino- and carboxy-protecting groups that can be used with the amino acids discussed herein are described by, for example, U.S. Pat. No. 5,221,736 (Coolidge et al.); U.S. Pat. No. 5,256,549 (Urdea et al.); U.S. Pat. No. 5,049,656 (Lewis et al.); and U.S. Pat. No. 5,521,184 (Zimmerman).

In certain embodiments, the amino acids and peptides described herein can be modified at their N- and/or C-terminus by various end-capping methodologies known in the art. For example, acetylation of the N-terminus can be accomplished by reacting the final peptide with acetic anhydride, in some instances before cleavage from a resin. The C terminus may be modified by standard methods through the choice of resin linker, such as by using a benzyl hydrylamine (carboxamide) or hydroxybenzyl linker (carboxylic acid). Additional N-terminus modifications include, but are not limited to, protecting groups such as Boc or Cbz, and also acyl groups, including but not limited to, propanoyl, butanoyl, pentanoyl, nonanoic acid, or pentadecanoic acid.

Additional C-terminus modifications include, but are not limited to, N-alkyl or N-aryl or N,N-dialkyl or N,N-diaryl amides and esters.

Compounds and Methods of the Invention.

The invention provides compounds and methods for preparing various useful compounds, for example, compounds of Formulas I—III, V—VI, and IX-X. Certain specific compounds of the invention include, but are not limited to, (S)-2-((1S,2S)-2-nitrocyclohexyl)butan-1-ol; (S)-2-((1S,2S)-2-nitrocyclohexyl)propan-1-ol; (S)-2-((1S,2S)-2-nitrocyclohexyl)pentan-1-ol; (S)-3-methyl-2-((1S,2S)-2-nitrocyclohexyl)butan-1-ol; (S)-2-((1S,2S)-2-nitrocyclohexyl) hexan-1-ol; (S)-2-((1S,2S)-2-nitrocyclohexyl)octan-1-ol; (S)-2-cyclohexyl-2-((1S,2S)-2-nitrocyclohexyl)ethanol; (S)-2-((1S,2S)-2-nitrocyclohexyl)-4-phenylbutan-1-ol; (S)-2-((1S,2S)-2-nitrocyclohexyl)butanoic acid; (S)-2-((1S,2S)-2-(tert-butoxycarbonylamino)cyclohexyl)butanoic acid; (S)-2-((1S,2R)-2-nitrocyclohexyl)butan-1-ol; (S)-2-((1S,2R)-2-nitrocyclohexyl)butanoic acid; (S)-2-((1S,2R)-2-(tert-butoxycarbonyl)cyclohexyl)butanoic acid; their enantiomers; their various diasteriomers; and various derivatives thereof, for example, compounds of Formulas I-X, and compounds described in the Examples below. Compounds that possess a chiral carbon can be prepared as either the (R)- or (S)-enantiomer, at any position that can be controlled by a chiral catalyst, by use of chiral starting materials, and/or by chiral purification techniques. The derivatives include, for example, compounds where an alkyl or aryl group is substituted, where an amine and/or acid moiety is protected, and/or where one or more (e.g., one to about eight) amino acids are covalently linked to an amino or carboxy moiety of an aforementioned compound.

The methods of the invention include preparing cyclically constrained α-substituted-γ-nitro-aldehyde compounds, and derivatives thereof, such as derivatives where the nitro group is reduced to an amine, and/or the aldehyde group is reduced to an alcohol or, in one or two steps, oxidized to a carboxylic acid. Cyclic compounds containing a 1-nitroethylene moiety within the ring, and an aldehyde that has an α-hydrogen atom, can be combined in the presence of an organic solvent, a proline derivative, and optionally a carboxylic acid under suitable reaction conditions to provide the α-substituted-γ-nitro-aldehyde.

Accordingly, various embodiment the invention provide compounds of the Formulas described herein, and methods for preparing them. As would be readily recognized by one skilled in the art, in any of the formulas when one of $A^3$-$A^6$ is carbon, its remaining valences are filled by hydrogen atoms, unless the variable is substituted by one or two substituents, as recited above. Likewise, when one of $A^3$-$A^6$ is nitrogen, the nitrogen atom can be substituted by one of the substituents recited above, or by a nitrogen protecting group. Additionally, while in some embodiments one or two of $A^3$-$A^6$ are nitrogen, each of $A^3$-$A^6$ may be carbon in other embodiments as specified by the definition that each of $A^3$-$A^6$ may be carbon.

In one embodiment, $A^3$ is carbon. In another embodiment, $A^3$ is nitrogen.

In one embodiment, $A^4$ is carbon. In another embodiment, $A^4$ is nitrogen.

In one embodiment, $A^5$ is carbon. In another embodiment, $A^5$ is nitrogen.

In one embodiment, $A^6$ is carbon. In another embodiment, $A^6$ is nitrogen. In another embodiment, $A^6$ is a direct bond, connecting $A^5$ to the carbon that is attached to Y or $NO_2$.

In one embodiment, $R^1$ can be hydrogen. In another embodiment, $R^1$ can be alkyl, for example, $(C_1$-$C_6)$alkyl, optionally substituted. In another embodiment, $R^1$ can be an optionally substituted cycloalkyl, aryl, heteroaryl, or heterocycle. The substituents can include one to five alkyl, alkoxy, halo, hydroxy, aryl, (aryl)alkyl, heteroaryl, heterocycle, cycloalkyl, alkanoyl, alkoxycarbonyl, amino, alkyl amino, dialkylamino, acylamino, nitro, trifluoromethyl, trifluoromethoxy, carboxy, carboxyalkyl, keto, arylsulfonyl, cyano, or azide groups. In any embodiment, the hydroxy, amino, alkylamino and/or carboxy groups of R' may be optionally protected. Hydroxy, amino, alkylamino and carboxy groups are preferably protected during the Michael reaction used to prepare such compounds, but can be removed after the Michael reaction to provide other compounds of the invention.

A specific value for $R^2$ is H. Another specific value for $R^2$ is OH.

The group $R^3$ is an amino acid side chain, for example, the side chain of Ala, Arg, Asn, Asp, Cys, Glu, Gln, Gly, His, Hyl, Hyp, Ile, Leu, Lys, Met, Phe, Pro, Ser, Thr, Trp, Tyr, or Val, as would be readily understood by one of skill in the art. The amino acid side chains can be optionally protected, for example, with oxygen, nitrogen, or sulfur protecting groups.

In one embodiment, P can be H. In another embodiment, P is methyl. In another embodiment, P is acetyl. In another embodiment, P is a carboxylic acid protecting group, for example, as described by Green. In another embodiment, P (or —OP) is an amino acid, for example, Ala, Arg, Asn, Asp, Cys, Glu, Gln, Gly, His, Hyl, Hyp, Ile, Leu, Lys, Met, Phe, Pro, Ser, Thr, Trp, Tyr, or Val, bonded to the carbonyl moiety of formula, thereby forming an amide bond.

In one embodiment, Y can be nitro. In another embodiment, Y is amino (—NH$_2$). In another embodiment, Y is protected amino, such as, —NHBoc-NHAc, —NHBn, —NHFmoc, or —NHCbz. In another embodiment, Y is a nitrogen bonded to an amino acid, for example, the carbonyl moiety of Ala, Arg, Asn, Asp, Cys, Glu, Gln, Gly, His, Hyl, Hyp, Ile, Leu, Lys, Met, Phe, Pro, Ser, Thr, Trp, Tyr, or Val, thereby forming an amide bond.

In yet another embodiment, the invention provides a method for preparing a compound described above wherein $R^2$ is H. The method can include contacting a cyclic compound of 5 or 6 ring atoms that includes a nitroethylene moiety (i.e., a —CH=C(NO$_2$)— group) within the ring and that optionally includes one or two nitrogen atoms in the ring, wherein the carbon atoms in the ring are optionally substituted and the optional nitrogen atom or atoms in the ring are optionally substituted by a nitrogen protecting group; and an aldehyde that has at least one α-hydrogen; in the presence of an organic solvent, and a proline derivative, for a period of time sufficient to provide an α-substituted-γ-nitro-aldehyde.

In an additional embodiment, the invention provides a method for preparing an α-substituted-γ-amino acid that includes a ring moiety attached to the carbons β and γ to the carboxylic acid moiety of the α-substituted-γ-amino acid, and the ring includes 5 or 6 carbon atoms, wherein one or two of the ring carbon atoms are optionally replaced with one or two nitrogen atoms, wherein the nitrogen atom or atoms in the ring are optionally substituted by a nitrogen protecting group, the method comprising contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has at least one α-hydrogen, in the presence of an organic solvent and a proline derivative; for a period of time sufficient to provide an α-substituted-γ-nitro-aldehyde that includes a ring moiety attached to the carbons β and γ to the aldehyde.

The method can further include reducing the aldehyde of the α-substituted-γ-nitro-aldehyde to an alcohol; oxidizing the alcohol to a carboxylic acid to provide an α-substituted-γ-nitro-acid; and/or reducing the nitro moiety of the α-substituted-γ-nitro-acid to an amine, to provide an α-substituted-γ-amino acid that includes a ring moiety attached to the carbons β and γ to the carboxylic acid moiety of the α-substituted-γ-amino acid.

The method can also include protecting the amine group of the α-substituted-γ-amino acid with a nitrogen protecting group, for example, a Boc group, an acetyl group, a benzyl group, an Fmoc group, or a Cbz group.

In an additional embodiment, the invention provides a method for preparing an amide compound that includes an α-substituted-γ-amino acid. The α-substituted-γ-amino acid can include a ring moiety attached to the carbons β and γ to the carboxylic acid moiety of the α-substituted-γ-amino acid. The α-substituted-γ-amino acid can be coupled to a variety of amino acids, such as an α-amino acid, a β-amino acid, or a γ-amino acid.

The method includes contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has at least one α-hydrogen; in the presence of an organic solvent and a proline derivative, for a period of time sufficient to provide an α-substituted-γ-nitro-aldehyde that includes a ring moiety attached to the carbons β and γ to the aldehyde. The method can also include reducing the aldehyde of the α-substituted-γ-nitro-aldehyde to an alcohol; oxidizing the alcohol to a carboxylic acid to provide an α-substituted-γ-nitro-acid; and/or forming a peptide bond with the carboxylic acid and the nitrogen moiety of an α-amino acid, a 3-amino acid, or a γ-amino acid. The α-amino acid, a n-amino acid, or a γ-amino acid can have a protected carboxylic acid group. The method can also include reducing the nitro moiety of the α-substituted-γ-nitro-acid to an amine, to provide an amide compound. In one embodiment, the method further includes protecting the amine group of the α-substituted-γ-amino acid with a nitrogen protecting group.

In another embodiment, the invention provides a method for preparing a α-substituted-γ-nitro-aldehyde that includes a ring moiety attached to the carbons β and γ to the carboxylic acid moiety of the α-substituted-γ-amino acid. The method can include contacting a cyclic compound of 5 or 6 ring atoms that includes a nitroethylene moiety within the ring and that optionally includes one or two nitrogen atoms in the ring, wherein the nitrogen atom or atoms in the ring are optionally substituted by a nitrogen protecting group; and an aldehyde that has an α-methylene group; in the presence of an organic solvent, an (S)- or (R)-diphenylprolinol trialkyl silyl ether, for a period of time sufficient to provide the α-substituted-γ-nitro-aldehyde, wherein the α-substituted-γ-nitro-aldehyde that includes a ring moiety attached to the carbons β and γ to the carboxylic acid moiety of the α-substituted-γ-amino acid is prepared in at least about 90% enantiomeric purity.

As would be recognized by one skilled in the art, the ring moieties of the starting materials or products that include one or two nitrogen atoms can be, for example, piperidine, piperazine, hexahydropyrimidine, pyrrolidine, pyrazolidine, or imidazolidine ring systems. Each carbon and/or nitrogen atom of the ring system can be substituted as recited herein.

Many of these compounds are commercially available from Sigma-Aldrich (St. Louis Mo.) or they can be readily prepared from such compounds using standard synthetic transformations known to those of skill in the art.

By using a chiral pyrrolidine catalyst, the compounds described above can be prepared in an enantiomerically enriched form. The compounds can be prepared in high ee, for example, as determined by NMR analysis, optionally of a derivative, such as a Mosher ester, or by one of the techniques described in the Examples. The compound can be prepared such that it has an enantiomeric purity of, for example, greater than about 75%, greater than about 80%, greater than about 90%, greater than about 95%, greater than about 97%, greater than about 98%, or greater than about 99%. In various embodiments, the enantiomeric purity may be characterized with respect to the carbon attached to $R^1$. In other embodiments, the enantiomeric purity may be characterized with respect to the entire molecule.

The cyclic compound of 5 or 6 ring atoms that includes a nitroethylene moiety can be contacted with an aldehyde that has an α-methylene group, or with an aldehyde that has an α-methine group.

The proline derivative can be a chiral pyrrolidine compound or catalyst. The chiral pyrrolidine catalyst can be an (S)- or (R)-diphenylprolinol trialkyl silyl ether, for example, (S)-diphenylprolinol trimethyl silyl ether, or (R)-diphenylprolinol trimethyl silyl ether.

Depending on the substrates and catalyst employed, the catalyst can be present in varying amounts. Typically a higher catalyst loading is required in the absence of an acid co-catalyst. The method can use about 1-50 mol % of the chiral pyrrolidine catalyst, with respect to the molar amount of the cyclic nitroethylene-containing compound. For example, the chiral pyrrolidine catalyst can be present in about 1-30 mol %, about 1-5 mol %, about 5-30 mol %, or about 10-25 mol %, with respect to the molar amount of the cyclic nitroethylene-containing compound. The proline derivative can also be present, for example, in about 0.5 mol %, about 1 mol %, about 2 mol %, about 5 mol %, about 10 mol %, about 20 mol %, or about 50 mol %, with respect to the molar amount of the cyclic nitroethylene-containing compound.

In any embodiment, the contacting can be carried out in the presence of a carboxylic acid, such as acetic acid, trifluoroacetic acid, benzoic acid, or a nitrobenzoic acid, such as o-, m-, or p-nitrobenzoic acid. The acid can be present in any suitable and effective amount. Accordingly, the carboxylic acid can be present in the reaction in about 1-200 mol % with respect to the molar amount of the cyclic nitroethylene-containing compound. For example, the carboxylic acid can be present in about 5-30 mol %, about 5-20 mol %, about 5-15 mol %, or about 10 mol %, with respect to the molar amount of the cyclic nitroethylene-containing compound. Typically, about 2-100 mol %, or about 5-20 mol % of the cocatalyst is used. Standard amounts include multiples of 5 mol % ranging from 5-100 mol %, with respect to the molar amount of nitroethylene.

The molar amount of the aldehyde can be greater than the molar amount of the cyclic nitroethylene-containing compound. For example, the cyclic nitroethylene-containing compound and the aldehyde can be present in about a 1:1.05 molar ratio, about a 1:1.1 molar ratio, about a 1:2 molar ratio, about a 1:3 molar ratio, about a 1:5 molar ratio, or about a 1:10 molar ratio.

Any suitably effective solvent can be used. The organic solvent can be a suitable organic solvent such as hexanes, DMSO, DMF, DMA, isopropanol, methylene chloride, chloroform, or an aryl solvent, such as benzene, toluene, or xylenes. In one embodiment, the aryl solvent is benzene or toluene. In another embodiment, the solvent is methylene chloride or chloroform. In some instances, an acid can be used as the solvent. For example, the solvent can be a carboxylic acid, such as acetic acid, which can also act as a co-catalyst. When an acid is used as the solvent, other solvents may be optional and not required.

The reaction can typically be run at about 0° C., or 3° C., or up to about room temperature (~23° C.). Under some circumstances, it may be desirable to run the reaction at a low temperature, for example, at less than about 0° C., or about −30° C. to about 0° C. Under other circumstances, it may be desirable to heat the reaction to above room temperature, for example, to about 30° C., about 40° C., about 50° C., or to about the reflux temperature of the solvent used in the reaction. Increased reaction temperatures can increase the reaction rate or total conversion of the starting materials to the product.

Favorable yields were obtained in numerous trials of the Michael addition reactions. In one embodiment, the yield of the Michael adduct compound is greater than about 50%. In another embodiment, the yield of the Michael adduct compound is greater than about 55%, greater than about 60%, greater than about 70%, greater than about 75%, greater than about 80%, greater than about 85%, or greater than about 90%. In some embodiments, aldol products are afforded in less than about 20% yield, in less than about 15% yield, in less than about 10% yield, or in less than about 5% yield.

As would be readily recognized by one skilled in the art, the methods can include reducing an aldehyde moiety of a product compound an alcohol. The reducing can include the use of a hydride, for example, a borohydride reagent, such as a sodium borohydride, or a lithium hydride reagent, such as lithium aluminum hydride. The method can also include oxidizing the alcohol to a carboxylic acid. The oxidizing can include the use of a chromium reagent, such as the Jones reagent. Additionally, the method can include reducing the nitro moiety of a product compound to an amine. The reducing can include the use of hydrogen gas and a transition metal reagent. The oxidizing and reducing steps can be carried out in any practical order, as recognized by one skilled in the art.

Organocatalyzed Michael Addition Reactions

New synthetic approaches to γ-amino acids and derivatives thereof are provided herein. The γ-amino acids can include a cycloalkyl or heterocyclic constraint on the $C_β$-$C_γ$ bond and a variable side chain at $C_α$. For example, the γ-amino acids, their precursors, and/or their derivatives, can include a ring, such as a cyclohexyl or piperidinyl constraint, on the $C_β$-$C_γ$ bond, as well as a variable side chain at $C_α$. All three stereocenters of the γ-amino acid skeleton are generated from achiral precursors in a single process with high diastereo- and enantioselectivity. When the cyclic moiety includes a stereocenter, additional diastereomers and enantiomers result. These new types of γ-amino acid residues support helix formation by an α/γ-peptide backbone.

The methods disclosed herein include a pyrrolidine-catalyzed Michael addition of an aldehyde to a 1-nitrocycloalkene or a 1-nitroheterocycloalkene. The 1-nitrocycloalkene can be a 5-8 membered ring, optionally with one or more substituents on the ring, as illustrated in Scheme 1. The ring can also be a 1-nitro unsaturated ring with one or two nitrogen atoms in the ring, optionally with one or more substituents on the ring.

Scheme 1.

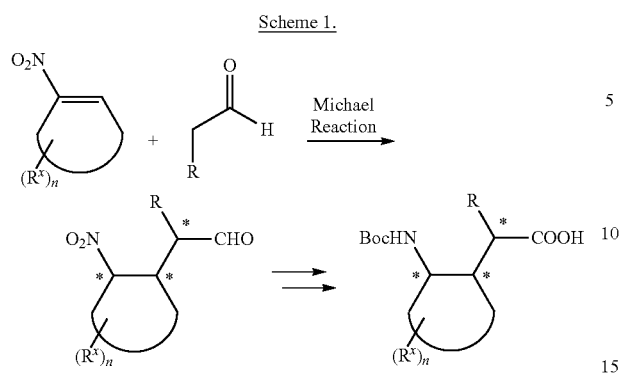

where R can be hydrogen, alkyl, cycloalkyl, aryl, heteroaryl, or heterocycle, each of which can be optionally substituted; $R^x$ can be alkyl, cycloalkyl, aryl, heteroaryl, or heterocycle, each of which can be optionally substituted; and n is 0 to about 10; wherein the 1-nitrocycloalkene is a 5, or 6 membered ring.

Chiral pyrrolidines have been shown to catalyze the Michael addition of aldehydes to nitroalkenes with high stereoselectivity. Most precedents involve β-aryl nitroalkenes, such as β-nitrostyrene, which lead to $\gamma^{2,3}$-amino acids. The Michael addition of aldehydes to nitroethylene provides access to $\gamma^2$-amino acids has also been reported (Chi et al., J. Am. Chem. Soc. 2008, 130, 5608).

Scheme 2 shows the pyrrolidine-catalyzed Michael addition of an aldehyde to 1-nitrocyclohexene. In Schemes 1 and 2, the Michael adduct can be further modified to conformationally constrained γ-amino acids by a series of facile oxidation/reduction reactions, optionally with the addition of protecting groups, such as Boc or benzyl groups.

Scheme 2.

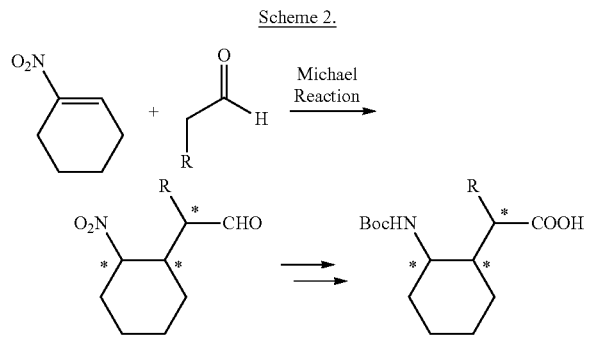

Wennemers and coworkers concurrently devised an effective tripeptide catalyst for nitroethylene additions (J. Am. Chem. Soc. 2008, 130, 5610). In complementary work, List and coworkers, and Hayashi and coworkers, found that (S)-A catalyzes highly enantioselective Michael additions of acetaldehyde to β-substituted nitroalkenes, which provides $\gamma^3$-amino acids (Angew. Chem., Int. Ed. 2008, 47, 4719 and Angew. Chem., Int. Ed. 2008, 47, 4722, respectively). Several pyrrolidine catalysts and acidic co-catalysts were analyzed to facilitate the Michael reaction. Herein is described the results of an analysis of pyrrolidine (S)-A along with acidic co-catalyst B, which proved to be highly suitable in terms of efficiency and enantioselectivity for preparation of the desired products.

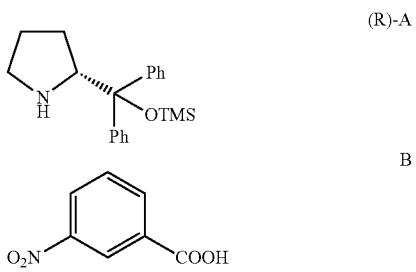

Attention was drawn to 1-nitrocyclohexene as a Michael acceptor because the adducts can be easily converted to novel cyclically constrained γ-amino acid residues. Reaction of n-butanal and 1-nitrocyclohexene (2:1 molar ratio) in the presence of 20 mol % A in toluene provided only 25% of the Michael adduct after 24 hours, and the two major diastereomers (2a and 3a) were produced in a ~1:1 ratio (Table 1, entry 1).

TABLE 1

Co-catalyst effects[a]

| entry | co-catalyst (mol %) | yield[b] (%) | dr[b,c] (2a:3a) | M:4[d] |
|---|---|---|---|---|
| 1 | none | 25 | 1:1 | 1:1 |
| 2 | m-NO$_2$C$_6$H$_4$CO$_2$H (10) | 44 | 6:1 | 1:2.2 |
| 3[e] | m-NO$_2$C$_6$H$_4$CO$_2$H (10) | 80 | 7:1 | 1:3.2 |
| 4[e] | HOAc (100) | 80 | 5:1 | 1:5.0 |
| 5[e] | TFA (10) | 0 | n.d | n.d. |
| 6[e] | Benzoic acid (10) | 82 | 5:1 | 1:1.8 |

[a]Reactions were performed with 1.0M 1-nitrocyclohexene using 2 equivalents of aldehyde.
[b]Determined from $^1$H NMR of the crude reaction mixture after 24 hours.
[c]See Example 1.
[d]M stands for all Michael adduct diastereomers observed by NMR.
[e]5 equivalents of n-butanal were employed.

When 10 mol % B was employed as a co-catalyst, the Michael adduct yield rose to 44% yield, and 2a was favored (6:1 dr); however, the major product was 4, resulting from aldol condensation. Michael adduct yield was improved to 80% (7:1 dr) by using 5 equivalents of n-butanal. Under these conditions, replacing B with either benzoic acid or acetic acid caused a modest decline in diastereoselectivity, and replacing B with trifluoroacetic acid completely inhibited the reaction. The acidic component may facilitate catalyst turnover, perhaps by promoting hydrolysis of an imminium intermediate. Thus, the selectivity for 2a relative to trans diastereomer 3a may result from preferential equatorial protonation of the 2-substituted cyclohexane nitronate intermediate.

Solvent choice proved to have a substantial impact on Michael adduct yield and diastereo-selectivity (Table 2). Both parameters reached suitable levels when the reaction was conducted in $CH_2Cl_2$ and catalyzed by 20 mol % A and 10 mol % B, starting with 0.5 M 1-nitrocyclohexene. These conditions led to high selectivity for cis adduct 2a (17:1 dr relative to 3a).

TABLE 2

Solvent effects.[a]

| entry | solvent | concentration of 1-nitrocyclohexene | Yield[b] (%) | dr[b] (2a:3a) |
|---|---|---|---|---|
| 1 | Toluene | 1.0M | 80 | 7:1 |
| 2 | Hexane | 1.0M | 80 | 5:1 |
| 3 | DMSO | 1.0M | 26 | 1:1 |
| 4 | DMF | 1.0M | 80 | 6:1 |
| 5 | i-PrOH | 1.0M | 55 | 4:1 |
| 6 | $CHCl_3$ | 1.0M | 85 | 10:1 |
| 7 | $CH_2Cl_2$ | 1.0M | 86 | 10:1 |
| 8 | $CHCl_3$ | 0.5M | 81 | 15:1 |
| 9 | $CH_2Cl_2$ | 0.5M | 82 | 17:1 |

[a]Reactions were performed using 5 equivalents of aldehyde.
[b]Determined from $^1$H NMR analysis of the crude reaction mixture after 24 hours.

Further exploration revealed that Michael additions to 1-nitrocyclohexene, catalyzed by A, are highly enantioselective and that many aldehydes are compatible with the catalytic process (Table 3). For these studies, ee was determined by HPLC after γ-nitro aldehydes had been reduced to the corresponding nitro alcohols, to avoid epimerization at the α-carbon.

TABLE 3

Aldehydes variation

TABLE 3-continued

| entry | product | R | t (h) | Yield[a] (%) | dr[b] | ee[c,d] (%) |
|---|---|---|---|---|---|---|
| 1 | 2a | Et | 38 | 87 | 17:1 | 99 |
| 2 | 2b | Me | 36 | 84 | 8:1 | 97 |
| 3 | 2c | n-Pr | 40 | 86 | 16:1 | 99 |
| 4 | 2d | i-Pr | 54 | 79 | 10:1 | >99 |
| 5 | 2e | n-Bu | 40 | 85 | 16:1 | 99 |
| 6 | 2f | n-Hex | 42 | 81 | 15:1 | >99 |
| 7 | 2g | c-Hex | 54 | 70 | 16:1 | >99 |
| 8 | 2h | $CH_2CH_2Ph$ | 40 | 75 | 9:1 | 98 |
| 9 | 2i | $(CH_2)_4N(Boc)_2$ | 42 | 73 | 13:1 | 96 |

[a]Yield of isolated alcohol (major diastereomer) after reduction with $NaBH_4$.
[b]Determined from $^1$H NMR of the crude reaction mixture.
[c]Determined by chiral HPLC analysis of the alcohol derived from 2a-i.
[d]Absolute configuration of 2a and 3a was determined by the X-ray structure analysis; see Expl. 1.

In terms of Michael addition scope (Table 3), it is noteworthy that aldehydes bearing a branch point adjacent to nucleophilic carbon (such as 1d and 1g) are tolerated, although these examples require somewhat longer reaction times (e.g., >2 days) to produce good yields, potentially due to steric effects reducing reactivity. The success of the aldehyde with a protected lysine-like side chain (1i) facilitates the synthesis of oligomers that can be subjected to conformational analysis in aqueous solution.

The absolute configuration of the major diastereomer generated with n-butanal and A was determined via derivatization (Scheme 3). Nitro alcohol 5 was oxidized to the corresponding nitro acid 6, which was then coupled to L-phenylalanine methyl ester. The nitro group in the product was hydrogenated, and the resulting amino group was protected with a Boc group. A crystal structure of this α/γ-dipeptide revealed the (S,S,S) configuration for the γ-amino acid residue. The absolute configuration of other Michael adducts (Table 3) was assigned by analogy. γ-Nitro acid 6 could be easily converted to the Boc-protected γ-amino acid 7.

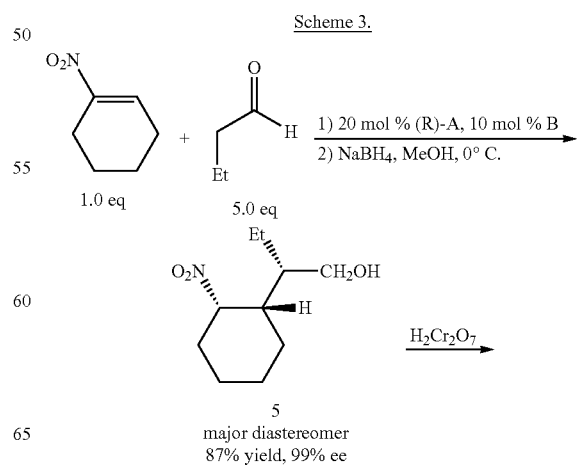

Scheme 3.

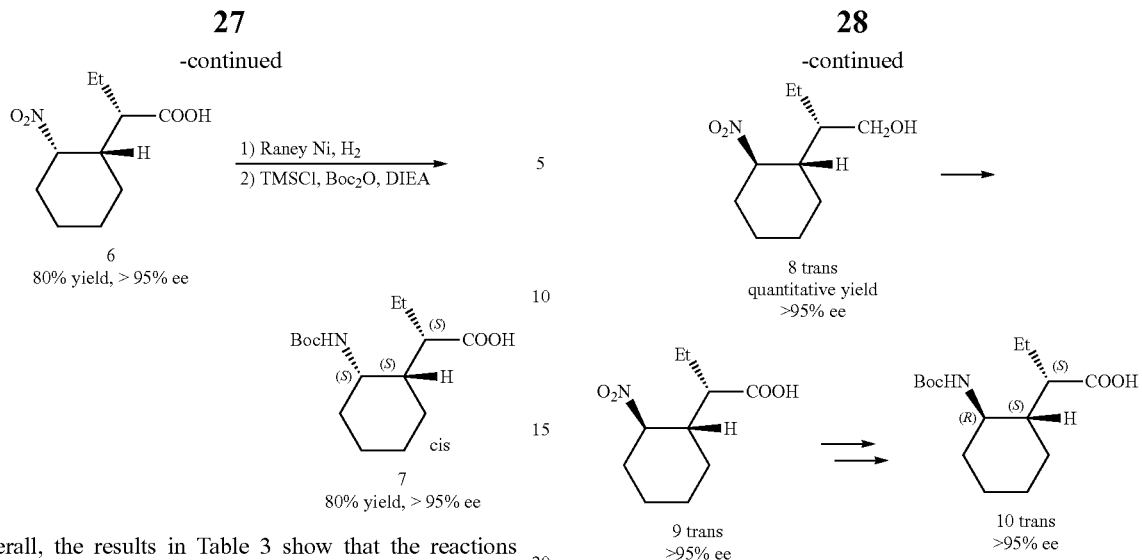

Overall, the results in Table 3 show that the reactions allow for rapid access to stereochemically pure γ-amino acid building blocks with a cis cyclohexyl constraint in the backbone and a variety of substituents adjacent to the carbonyl. The utility of the Michael addition-based approach is enhanced by the fact that the analogous trans diastereomers can be easily generated as well, as illustrated in Scheme 4. Thus, treating cis nitro alcohol 5 with NaHCO$_3$ in ethanol at reflux quantitatively induces epimerization at the nitro-bearing carbon. Subsequent oxidation yields nitro acid 9, which is identical to the nitro acid obtained by oxidation of 3a (the minor product of the Michael addition, which was characterized crystallographically). Boc-protected γ-amino acid 10 can be readily prepared from 9.

Scheme 4.

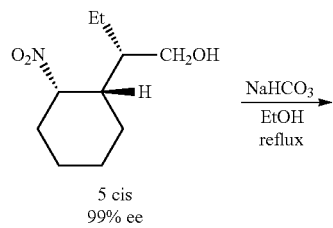

The availability of cyclically constrained γ-amino acid building blocks in stereochemically pure form led to the exploration of the conformational behavior of oligomers containing the corresponding subunits. Oligomers constructed from α- and flexible γ-amino acid subunits can display a variety of discrete folding patterns. It is believed that the α/γ-peptide foldamers will be conformationally stabilized by γ-residues with appropriate cyclic constraints.

Simulations from Hofmann et al. (*J. Org. Chem.* 2006, 71, 2000) have identified a number of helical conformations that could be adopted by oligomers with a 1:1 alternation of α- and γ-residues. The helix containing 12-atom ring C=O(i)-H—N(i+3) H-bonds, which may be designated the α/γ-peptide "12-helix", is predicted to have the g, g local conformation about the $C_\alpha$-$C_\beta$ (ζ) and $C_\beta$-$C_\gamma$ (θ) bonds. Fundamental principles indicate that γ-residues derived from 7 (Scheme 5) will favor this local conformation. It is believed that the α/γ-peptide 12-helix secondary structure would be favored by combining (R,R,R)-7 (generated with (S)-A) with D-α-amino acid residues. This was tested by preparation and analysis of tetramer 11 and hexamer 12.

Scheme 5. Intramolecular H-bonding patterns in the crystal structures of 11 and 12.

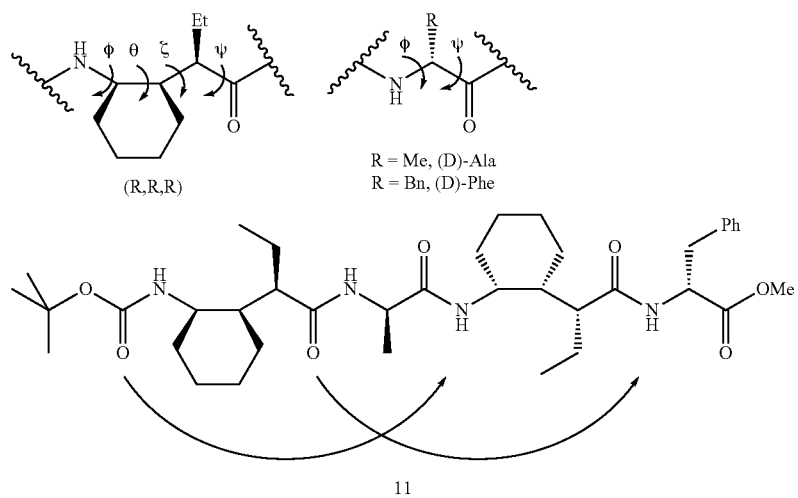

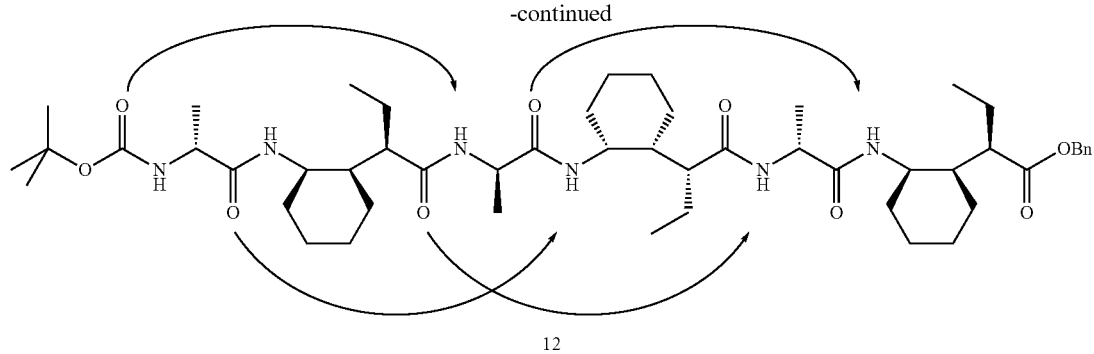

12

Crystal structures of both 11 and 12 reveal 12-helical conformations (FIG. 1). In each case the maximum number of C=O(i)-H—N(i+3) H-bonds is formed. α/γ-Peptide 12 displayed sufficient proton resonance dispersion in CDCl$_3$ solution to enable NOESY analysis. Among the unambiguous NOEs involving backbone protons, four strong NOEs were observed between protons from different γ-residues: C$_\gamma$H(2)-NH(4), C$_\gamma$H(2)-C$_\alpha$H(4), C$_\gamma$H(4)-C$_\alpha$H(6) and C$_\gamma$H(4)-NH(6) (Scheme 6). The C$_\gamma$H(i)-NH(i+2) distances in the crystal structure of 12 are 2.5 and 2.7 Å, and the C$_\gamma$H(i)-C$_\alpha$H(i+2) distances are 2.4 and 2.4 Å, which indicates that these two NOE patterns should be characteristic of the α/γ-peptide 12-helix in solution. Balaram and coworkers (*J. Am. Chem. Soc.* 2009, 131, 5956) have recently suggested that 1:1 α/γ-peptides derived from exclusively achiral amino acids can adopt the 12-helix in chloroform, but in these cases only nearest neighbor NH(i)-NH(i+1) NOEs were observed.

Scheme 6. Characteristic NOEs patterns observed for the 1:1 α/γ-peptide hexamer 12 in CDCl$_3$.

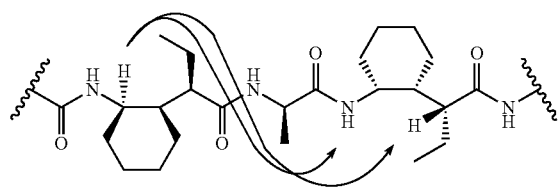

Accordingly, a short and general route to γ-amino acids has been developed that features a cycloalkyl or heterocyclic constraint on the C$_\beta$-C$_\gamma$ bond and a variety of side chains at C$_\alpha$. The route involves a Michael addition of an aldehyde to 1-nitro-cycloalkane or heterocycle, a process that can be catalyzed by a pyrrolidine, such as A. Under selected conditions, the reaction strongly favors just one of the eight possible stereoisomers. A second stereoisomer is available via epimerization at C$_\gamma$. Absolute configuration can be controlled by the enantiomer of catalyst A, which also can be employed. α/γ-Peptides containing the constrained γ-residues favor a specific helical conformation. Incorporation of these new γ-residues into other types of heterogeneous peptidic backbones allows for access to new families of foldamers. Synthetic approaches related to those described herein can provide access to γ-amino acids with complementary constraints that further broaden the foldamer realm.

Preparation of Peptides

The compounds and peptides described herein can be prepared by the synthetic chemical procedures described herein, as well as other procedures such as those used for making α-amino acid peptides. Such procedures include both solution and solid phase procedures, such as the use of Boc and Fmoc protection methods. Thus the compounds and peptides described herein can be prepared by successive amide bond-forming procedures in which amide bonds are formed between the amino group of a first amino acid residue or a precursor thereof and the carboxyl group of a second amino acid residue or a precursor thereof. The amide bond-forming step may be repeated as many times, and with specific α-amino acid residues and/or β-amino acid residues and/or γ-amino acid residues and/or precursors thereof, as required to give the desired peptide. Also peptides comprising two, three, or more amino acid residues (α or β or γ) may be joined together to yield larger α/β/γ-peptides. Cyclic compounds may be prepared by forming peptide bonds between the N-terminal and C-terminal ends of a previously synthesized linear polypeptide.

Additionally, β$^3$-amino acids may be produced enantioselectively from corresponding α-amino acids; for instance, by Arndt-Eisert homologation of N-protected α-amino acids. Such homologation may be conveniently followed by coupling of the reactive diazo ketone intermediate of the Wolff rearrangement with an amino acid residue described herein.

The method described herein can be used to establish discrete compound collections or libraries of compounds, for example, for use analyzing peptide folding or in screening for compounds having desirable activities, in particular biological activities indicative of particular pharmaceutical uses.

Solid-Phase and Solution-Phase Polypeptide Synthesis: Construction of polypeptides using any type of amino acid residue can be accomplished using conventional and widely recognized solid-phase or solution-phase synthesis. Very briefly, in solid-phase synthesis, the desired C-terminal amino acid residue is linked to a polystyrene support as a benzyl ester. The amino group of each subsequent amino acid to be added to the N-terminus of the growing peptide chain is protected with Boc, Fmoc, or another suitable protecting group. Likewise, the carboxylic acid group of each subsequent amino acid to be added to the chain is activated with DCC and reacted so that the N-terminus of the growing chain bears a removable protecting group. The process is repeated (with rinsing of the beads between each step) until the desired polypeptide is completed. In typical processes, the N-terminus of the growing chain is protected with a Boc group, which is removed using trifluoracetic acid, leaving behind a protonated amino group. Triethylamine is used to remove the proton from the N-terminus of the chain, leaving a free amino group, which is then reacted with the activated carboxylic acid group from a new protected amino acid. When the desired chain length is reached, a strong acid, such as hydrogen bromide in trifluoracetic acid, is used to both cleave the C-terminus from the polystyrene support and to remove the N-terminus protecting group.

Solid-phase peptide synthesis is widely employed and is well known. See, for example, "Peptide Synthesis, Structures, and Applications" by Academic Press (1995). Consequently, it will not be described in further detail here. Conventional solution-phase peptide synthesis can also be used with equal success.

Accordingly, the amino acids described herein can be used to fabricate polypeptide compounds ("peptides") by any means of polypeptide synthesis now known or developed in the future. Using current methods of peptide synthesis, peptides of about 100 residues long can be readily prepared. Peptides used to study protein folding an interactions are often about five or ten total residues to about 50 total residues, typically about 20 and about 50 total residues. Ranges above and below these stated ranges are also within the scope of the invention. Many commercial services, such as Abgent (San Diego, Calif., USA) offer peptide synthesis services up to about 100 residues.

Compound Salts and Solvates

The compounds described herein may be isolated in various forms. The compounds may be isolated in the form of a salt or solvate. For example, in cases where compounds are sufficiently basic or acidic to form stable nontoxic acid or base salts, isolation of the compounds as salts may be achieved. Examples of acceptable salts are organic acid addition salts formed with acids which form suitable anions, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts. Various salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium or magnesium) salts of carboxylic acids can also be prepared by analogous methods. Other suitable salts are found in, for example, Handbook of Pharmaceutical Salts, P. H. Stahl and C. G. Wermuch, Eds., 2002, Verlag Helvitica Chemica Acta (Zurich, Switzerland) and S. M. Berge, et al., "Pharmaceutical Salts," *J. Pharm. Sci.*, 66: p. 1-19 (January 1977), both of which are incorporated herein by reference.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compound Preparation and Analysis

I. Materials and Instrumentation

Proton nuclear magnetic resonance ($^1$H NMR) spectra were recorded on Bruker AC-300 (300 MHz) spectrometers. Chemical shifts were recorded in parts per million (ppm, δ) relative to tetramethylsilane (δ 0.00). NMR splitting patterns are designated as singlet (s), doublet (d), triplet (t), or quartet (q). First-order splitting patterns were assigned on the basis of the appearance of the multiplet. Splitting patterns that could not be easily interpreted are designated as multiplet (m) or broad (br). Carbon nuclear magnetic resonance ($^{13}$C NMR) spectra were recorded on a Bruker AC-300 (75 MHz) spectrometer. Mass spectra (MS) were obtained using an electrospray ionization (ESI) mass spectrometer. Optical rotations were measured using a 1 mL cell with a 1 dm path length on a Perkin-Elmer 241 digital polarimeter and are reported as follows: $[\alpha]^n_D$ (e in g per 100 mL solvent). Flasks were oven-dried overnight and cooled under a stream of nitrogen. Reagents were typically purchased from Aldrich Chemical Company. Flash chromatography was performed using silica gel 60 Å (32-63 mesh) from Sorbent Technologies. Reactions were monitored by thin layer chromatography (TLC) using 0.25 mm E, using Merck pre-coated silica gel 60 (particle size 0.040-0.063 mm). Visualization was performed using a UV lamp or potassium permanganate stain.

II. General Procedure for Organocatalytic Michael Reaction of Aldehydes with 1-Nitrocyclohexene To an 8 mL vial equipped with a small magnetic stir bar was added 0.2 mmol of amine catalyst A (65 mg, 20 mol %) in CH$_2$Cl$_2$ (1 mL), 0.1 mmol 3-nitrobenzoic acid B (16.7 mg, 10 mol %) and 5.0 mmol aldehyde (5.0 equiv.). Aldehydes 1g and 1h were prepared in one step from commercially available alcohols via PCC oxidation. The mixture was stirred at room temperature for about 1 minute, and then 1 mmol 1-nitrocyclohexene (113 μL, 1.0 equiv.) was added. The total volume of the reaction mixture was about 2 mL ([1-nitrocyclohexene] in reaction mixture ~0.5 M). The mixture was stirred at room temperature. The reaction progress was monitored by $^1$H NMR analysis of the crude reaction mixture.

Specifically, 50 μL crude reaction mixture was mixed with 500 μL CDCl$_3$ for $^1$H NMR analysis. After the NMR showed that the reaction was complete. The crude reaction mixture was purified via SiO$_2$ column chromatography eluting with EtOAc/hexane to give the desired α-substituted-γ-nitroaldehyde (major diastereomer). The major diastereomer was isolated from the minor diastereomers before reduction by NaBH$_4$. They are sometimes not separable by silica gel column chromatography after transformation of aldehydes into alcohols. To a stirred suspension of aldehydes in MeOH (10 mL) at 0° C. was added excess NaBH$_4$ (1.7 mmol, 65 mg). The mixture was stirred for a few minutes. The mixture was then slowly poured into a 100 mL beaker containing 10 mL 1 M NH$_4$Cl at 0° C., and the resulting mixture was extracted with EtOAc (about 3×10 mL). Extraction of the product into the organic phase was monitored by TLC analysis. The organic layers were collected, washed with 20 mL brine, dried over MgSO$_4$ and filtered. The filtrate was concentrated to give the crude alcohol product, which was purified via column chromatography eluting with EtOAc/hexane to give the desired β-substituted-δ-nitroalcohols.

III. Stereochemistry Determination

Combining n-butanal and nitroalkene reactants (6:1) with 20 mol % (R)-A and 10 mol % m-nitrobenzoic acid in dichloromethane for 36 hours at room temperature (~23° C.), the crude reaction mixture was purified via SiO₂ column chromatography eluting with EtOAc/hexane to give the desired α-substituted-γ-nitroaldehyde (major diastereomer 2a). Reduction of the aldehyde 2a by using NaBH₄ (to avoid epimerization at C2), provided the δ-nitro alcohol product 5. Jones oxidation of δ-nitro alcohol 5 provided the γ-nitro-α-alkylbutyric acid 6, which was then coupled to (L)-phenylalanine methyl ester to afford coupling product. The α/γ dipeptide was prepared in an efficient one-pot operation involving nitro group reduction followed by Boc protection.

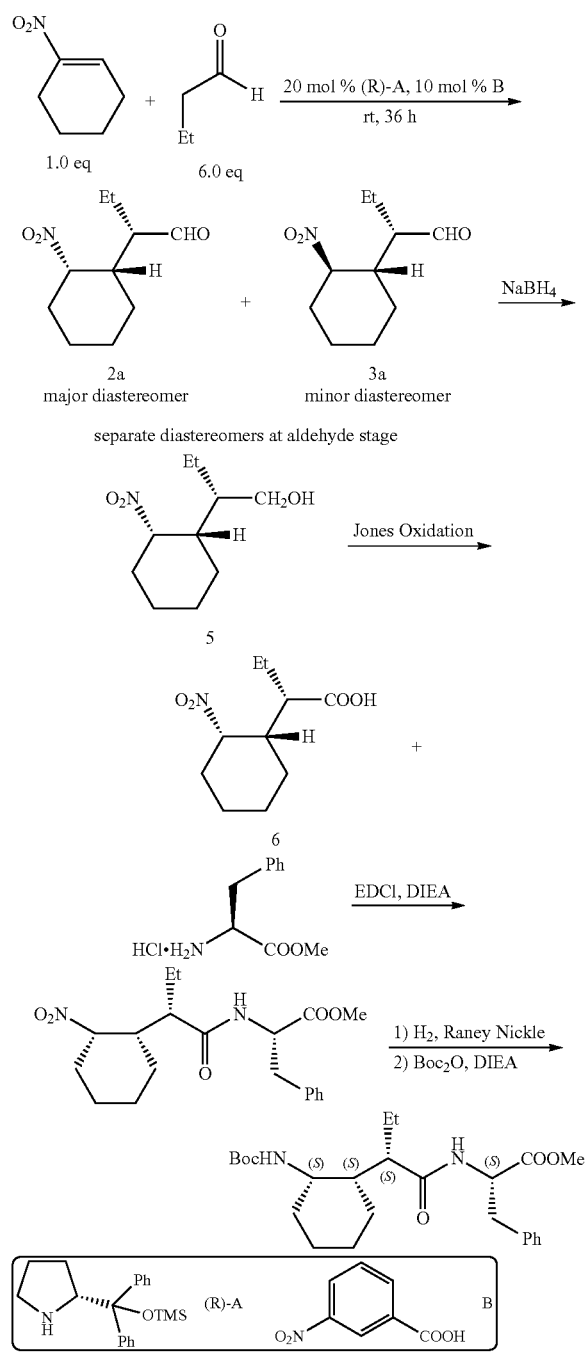

The absolute configuration of major diastereomer 2a was determined as (S,S,S) by the X-ray structure analysis of the L-phenylalanine derivative, and other β-substituted-δ-nitrobutanol configurations were assigned by analogy. The absolute configuration of minor diastereomer (ent)-3a, which was prepared from Michael reaction catalyzed by 20 mol % (S)-A and 10 mol % m-nitrobenzoic acid, was determined as (S,R,R) by X-ray structure analysis of the corresponding nitro acid.

IV. Determination of the Michael Product d.r. Via ¹H NMR

The d.r. values shown in Tables 2 and 3 in description above were determined via ¹H NMR analysis of crude reaction mixtures. In a typical procedure, 50 μL Michael reaction solution was dissolved in 500 μL CDCl₃ for ¹H NMR analysis.

A representative d.r. determination, involving the product from n-butanal, was carried out as follows. The product from n-butanal was prepared as illustrated below in Scheme 1-1. Three out of eight possible stereoisomers, 2a, 3a and I, were detected in the ¹H NMR spectrum of the crude reaction mixture. Based on integration of C(=O)—H resonances, 2a:3a:I=100:5.7:1.5. The reported d. r. values in this and other cases are based on only the two most abundant diastereomers (in this case 2a:3a=17:1). Only very small amounts of I of the analogous minor products in other cases were observed.

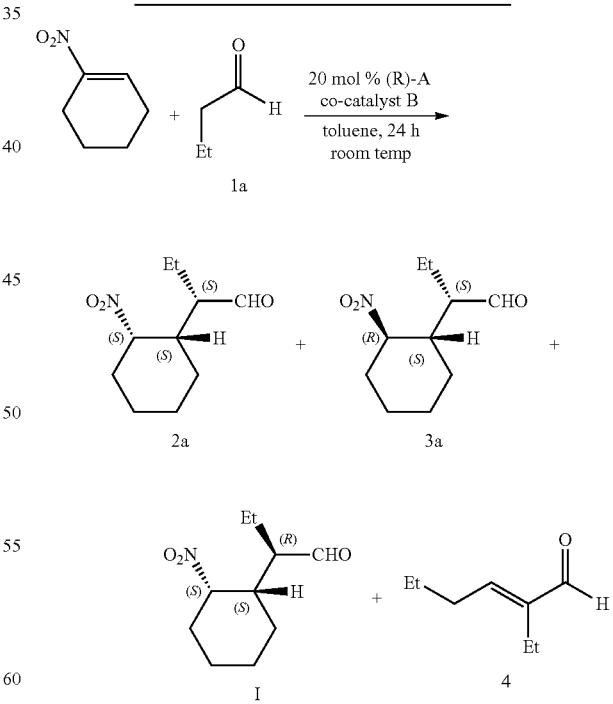

The absolute stereochemistry of 2a (S,S,S) and 3a (R,S,S) was determined by X-ray crystallography analysis of derivatives, as described above in Section III. Based on this knowledge, and on comparative analysis of the ¹H NMR spectra of purified samples of 2a, 3a and I, two stereocenters were assigned in product I, S adjacent to the nitro group and R adjacent to the aldehyde, using coupling constant data, as discussed below.

Scheme 1-2. $^1$H NMR analysis of isolated product 2a

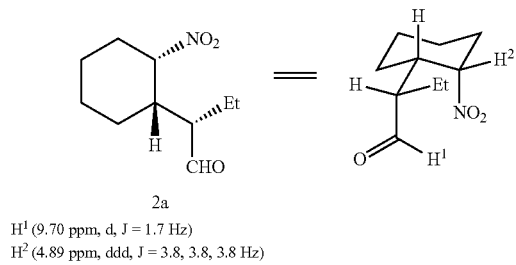

2a $H^1$ (9.70 ppm, d, J = 1.7 Hz)
$H^2$ (4.89 ppm, ddd, J = 3.8, 3.8, 3.8 Hz)

Scheme 1-2 shows the $^1$H NMR spectrum of aldehyde 2a. The coupling constant between $H^2$ and neighboring protons are consistent with the expectation that $H^2$ has equatorial-equatorial and equatorial-axial relationships (small coupling constants in each case: J=3.8, 3.8, 3.8 Hz). Thus, $H^2$ appears to occupy an equatorial position, as expected. The resulting stereochemical assignment of the stereocenter adjacent to $H^2$ based on the coupling constants is in agreement with the stereochemistry indicated by X-ray crystallography of derivatives of 2a, as described above.

Scheme 1-3. $^1$H NMR analysis of isolated product 3a

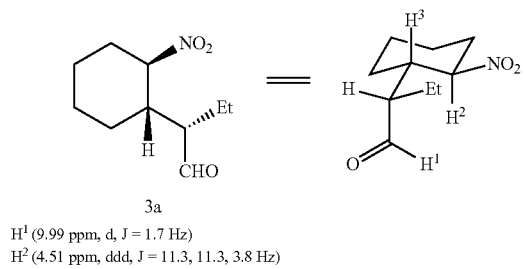

3a $H^1$ (9.99 ppm, d, J = 1.7 Hz)
$H^2$ (4.51 ppm, ddd, J = 11.3, 11.3, 3.8 Hz)

For 3a, the coupling constants between $H^2$ and neighboring protons indicate axial-equatorial and axial-axial relationships (one small and two large coupling constants: J=11.3, 11.3, 3.8 Hz). This information indicates that protons $H^2$ and $H^3$ occupy axial positions. The resulting stereochemical assignments are consistent with those obtained from X-ray crystallography of a derivative of 3a, as described above.

Scheme 1-4 illustrates the $^1$H NMR analysis of aldehyde I. The coupling constants between $H^2$ and neighboring protons indicate equatorial-equatorial and equatorial-axial relationships (all coupling constants are small: J=3.8, 3.8, 3.8 Hz). These data indicate that $H^2$ occupies an equatorial position. In principle, either of the two conformations shown above is consistent with this assignment, but there is a logical preference for the one in which $H^3$ is axial because in the alternative both substituents would be axial on the cyclohexane ring. Therefore, it has been concluded that I must be the diastereomer that differs from 2a at the stereocenter adjacent to the aldehyde, as indicated in Scheme 1-4. This conclusion is supported by the difference in coupling constants for the aldehyde proton ($H^1$) in I (J=3.3 Hz) and 2a (J=1.7 Hz).

V. Characterization Information for Michael Products (S)-2-((1S,2S)-2-Nitrocyclohexyl)butan-1-ol

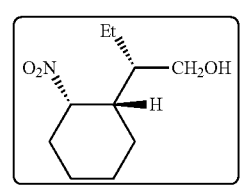

2a

The product was obtained as a yellow oil following the standard procedure and purified by column chromatography. TLC $R_f$=0.55 (EtOAc/hexanes, v/v, 1:1). The enantiomeric excess was determined by HPLC using a Chiracel OD-H column, λ=220 nm, hexane/isopropanol (v/v: 99.5/0.5, premixed), flow rate=1.0 mL/min; $t_R$=49.7 min (minor), 51.7 min (major) (99% ee); $^1$H NMR: (299.7 MHz, CDCl$_3$) δ 4.99 (q, J=2.7 Hz, 1H), 3.70 (m, 2H), 2.34 (m, 1H), 1.89 (m, 1H), 1.84-1.70 (m, 4H), 1.64-1.45 (m, 4H), 1.39-1.22 (m, 3H), 0.90 (t, J=6.9 Hz, 3H); $^{13}$C NMR: (75.4 MHz, CDCl$_3$) δ 84.70, 61.85, 43.25, 40.63, 31.22, 25.68, 23.75, 21.04, 20.50, 11.63; HRMS m/z (ESI): calcd. for C$_{10}$H$_{19}$NO$_3$Na [M+Na]$^+$ 224.1258. found 224.1267. Optical rotation: [α]$^{rt}_D$+1.32 (c 0.985, CHCl$_3$).

Scheme 1-4. $^1$H NMR of isolated product I.

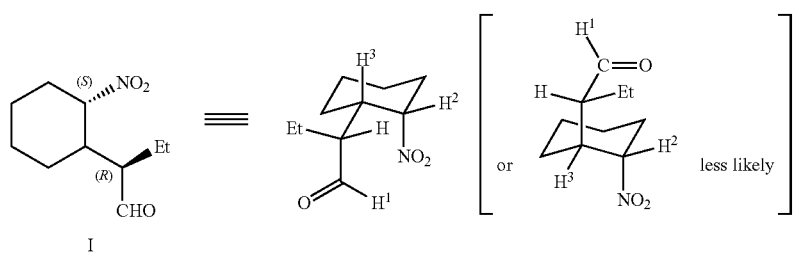

I $H^1$ (9.59 ppm, d, J = 3.3 Hz)
$H^2$ (4.81 ppm, ddd, J = 3.8, 3.8, 3.8 Hz)

(S)-2-((1S,2S)-2-Nitrocyclohexyl)propan-1-ol

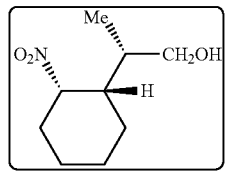

The product was obtained as a yellow oil following the standard procedure and purified by column chromatography. TLC $R_f$=0.45 (EtOAc/hexanes, v/v, 1:1). The enantiomeric excess was determined by HPLC using a Chiracel AD-H column, λ=220 nm, hexane/isopropanol (v/v: 95/5), flow rate=0.6 mL/min; $t_R$=24.3 min (major), 36.6 min (minor) (97% ee); $^1$H NMR: (299.7 MHz, CDCl$_3$) δ 4.98 (q, J=2.9 Hz, 1H), 3.61 (m, 2H), 2.31 (m, 1H), 1.90 (m, 1H), 1.82-1.65 (m, 5H), 1.62-1.57 (m, 1H), 1.40-1.29 (m, 3H), 0.981 (d, J=6.9, 3H) $^{13}$C NMR: (75.4 MHz, CDCl$_3$) δ 84.6, 66.1, 41.6, 37.0, 30.9, 25.5, 23.6, 20.4, 15.3; C$_9$H$_{17}$NO$_3$Na [M+Na]$^+$ 210.1101. found 210.1102. Optical rotation: [α]$^{rt}_D$+5.8 (c 0.34, CHCl$_3$).

(S)-2-((1S,2S)-2-Nitrocyclohexyl)pentan-1-ol

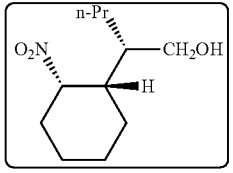

The product was obtained as a yellow oil following the standard procedure and purified by column chromatography. TLC $R_f$=0.25 (EtOAc/hexanes, v/v, 1:3). The enantiomeric excess was determined by HPLC using a Chiracel OD-H column, λ=220 nm, hexane/isopropanol (v/v: 99.3/0.7), flow rate=0.7 mL/min; $t_R$=44.7 min (minor), 45.4 min (major) (99% ee); $^1$H NMR: (299.7 MHz, CDCl$_3$) δ 4.99 (q, J=2.3 Hz, 1H), 3.68 (m, 2H), 2.38-2.95 (m, 1H), 1.95-1.85 (m, 1H), 1.81-1.69 (m, 4H), 1.64-1.51 (m, 3H), 1.43-1.22 (m, 6H), 0.90 (t, J=6.4 Hz, 3H); $^{13}$C NMR: (75.4 MHz, CDCl$_3$) δ 84.6, 62.3, 41.7, 40.8, 31.2, 30.8, 25.7, 23.8, 20.5, 20.5, 14.5; HRMS m/z (ESI): calcd. for C$_{11}$H$_{21}$NO$_3$Na [M+Na]$^+$ 238.1414. found 238.1411. Optical rotation: [α]$^{rt}_D$-5.1 (c 1.76, CHCl$_3$).

(S)-3-methyl-2-((1S,2S)-2-nitrocyclohexyl)butan-1-ol

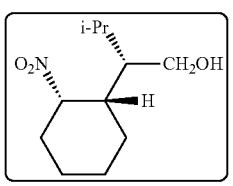

The product was obtained as a white solid following the standard procedure and purified by column chromatography. TLC $R_f$=0.65 (EtOAc/hexanes, v/v, 1:1). The enantiomeric excess was determined by HPLC using a Chiracel OD-H column, λ=220 nm, hexane/isopropanol (v/v: 96/4), flow rate=0.8 mL/min; $t_R$=26.3 min (minor), 27.2 min (major) (>99% ee); $^1$H NMR: (299.7 MHz, CDCl$_3$) δ 5.11 (q, J=3.4 Hz, 1H), 3.82 (m, 1H), 3.67 (m, 1H), 2.41-2.32 (m, 1H), 1.99 (pd, J=7, 3.1 Hz, 1H), 1.95-1.75 (m, 5H), 1.59 (m, 2H), 1.47 (m, 1H), 1.33 (m, 1H), 1.20 (m, 1H), 1.00 (d, J=7 Hz, 3H), 0.83 (d, J=7.0 Hz, 3H); $^{13}$C NMR: (75.4 MHz, CDCl$_3$) δ 84.9, 60.8, 46.7, 40.1, 31.6, 26.5, 25.7, 23.9, 22.2, 20.4, 17.2; HRMS m/z (ESI): calcd. for C$_{11}$H$_{21}$NO$_3$Na [M+Na]$^+$ 238.1414. found 238.1412. Optical rotation: [α]$^{rt}_D$+1.06 (c 1.70, CHCl$_3$).

(S)-2-((1S,2S)-2-Nitrocyclohexyl)hexan-1-ol

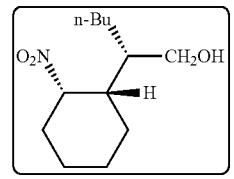

The product was obtained as a pale yellow oil following the standard procedure and purified by column chromatography. TLC $R_f$=0.575 (EtOAc/hexanes, v/v, 1:1). The enantiomeric excess was determined by HPLC using a Chiracel AD-H column, λ=220 nm, hexane/isopropanol (v/v: 98/2), flow rate=0.7 mL/min; $t_R$=30.6 min (major), 35.1 min (minor) (99% ee); $^1$H NMR: (299.7 MHz, CDCl$_3$) δ 4.99 (q, J=2.8 Hz, 1H), 3.71, 3.65 (AB of ABX, $J_{AB}$=11.0 Hz, $J_{AX}$=2.4 Hz, $J_{BX}$=4.0 Hz, 2H), 2.39-2.28 (m, 1H), 1.95-1.86 (m, 1H), 1.81-1.68 (m, 4H), 1.64-1.49 (m, 3H), 1.38-1.14 (m, 8H), 0.89 (t, J=6.9 Hz, 3H); $^{13}$C NMR: (75.4 MHz, CDCl$_3$) δ 84.6, 62.3, 41.8, 40.9, 31.3, 29.6, 28.2, 25.7, 23.8, 23.2, 20.5, 14.2; HRMS m/z (ESI): calcd. for C$_{12}$H$_{23}$NO$_3$Na [M+Na]$^+$ 252.1571. found 252.1579. Optical rotation: [α]$^{rt}_D$-6.48 (c 1.96, CHCl$_3$).

(S)-2-((1S,2S)-2-Nitrocyclohexyl)octan-1-ol

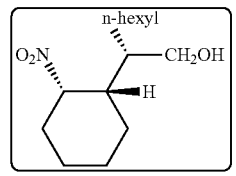

The product was obtained as a yellow oil following the standard procedure and purified by column chromatography. TLC $R_f$=0.54 (EtOAc/hexanes, v/v, 1:1). The enantiomeric excess was determined by HPLC using a Chiracel OD-H column, λ=220 nm, hexane/isopropanol (v/v: 95/5), flow rate=0.4 mL/min; $t_R$=51.2 min (minor), 53.1 min (major) (>99% ee); $^1$H NMR: (299.7 MHz, CDCl$_3$) δ 4.99 (q, J=2.7 Hz, 1H), 3.72, 3.65 (AB of ABX, $J_{AB}$=10.8 Hz, $J_{AX}$=3.7 Hz, $J_{BX}$=4.3 Hz, 2H), 2.34 (m, 1H), 1.89 (m, 1H), 1.80-1.69 (m, 4H), 1.68-1.50 (m, 4H), 1.32-1.20 (m, 11H), 0.88 (t, J=7.2 Hz, 3H); $^{13}$C NMR: (75.4 MHz, CDCl$_3$) δ 84.6, 62.3, 41.9, 40.9, 32.0, 31.2, 29.8, 28.5, 27.4, 25.7, 23.8, 22.8, 20.5, 14.2; HRMS m/z (ESI): calcd. for C$_{14}$H$_{17}$NO$_3$Na [M+Na]$^+$ 280.188. found 280.1890. Optical rotation: $[\alpha]^{rt}_D$-6.5 (c 0.99, CHCl$_3$).

(S)-2-cyclohexyl-2-((1S,2S)-2-nitrocyclohexyl)ethanol

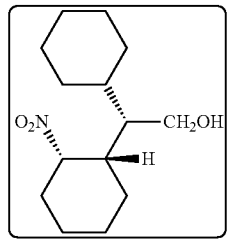

2g

The product was obtained as a white solid following the standard procedure and purified by column chromatography. TLC R$_f$=0.15 (EtOAc/hexanes, v/v, 1:3). The enantiomeric excess was determined by HPLC using a Chiracel AD-H column, λ=220 nm, hexane/isopropanol (v/v: 95/5), flow rate=1.0 mL/min; t$_R$=9.6 min (major), 12.4 min (minor) (>99% ee); $^1$H NMR: (299.7 MHz, CDCl$_3$) δ 5.10 (q, J=2.80 Hz, 1H), 3.82, 3.69 (AB of ABX, J$_{AB}$=11.4 Hz, J$_{AX}$=3.0, J$_{BX}$=4.2 Hz, 2H), 2.37 (m, 1H), 1.97-1.87 (m, 2H), 1.86-1.77 (m, 2H), 1.78-1.66 (m, 4H), 1.65-1.57 (m, 4H), 1.47-1.40 (m, 2H), 1.39-1.24 (m, 4H), 1.20-1.06 (m, 3H); $^{13}$C NMR: (75.4 MHz, CDCl$_3$) δ 85.02, 61.37, 46.77, 39.33, 37.77, 32.89, 31.89, 28.33, 27.72, 27.37, 26.97, 25.82, 23.94, 20.98. HRMS m/z (ESI): calcd. for C$_{14}$H$_{25}$NO$_3$Na [M+Na]$^+$ 278.170. found 278.1733. Optical rotation: $[\alpha]^{rt}_D$-5.6 (c 0.3, CHCl$_3$).

(S)-2-((1S,2S)-2-Nitrocyclohexyl)-4-phenylbutan-1-ol

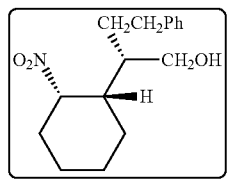

2h

The product was obtained as a yellow oil following the standard procedure and purified by column chromatography. TLC R$_f$=0.55 (EtOAc/hexanes, v/v, 1:1). The enantiomeric excess was determined by HPLC using a Chiracel AD-H column, λ=220 nm, hexane/isopropanol (v/v: 95/5), flow rate=0.8 mL/min; t$_R$=15.2 min (major), 16.9 min (minor) (98% ee); $^1$H NMR: (299.7 MHz, CDCl$_3$) δ 7.31-7.24 (m, 2H), 7.21-7.14 (m, 3H), 4.99 (q, J=3.5 Hz, 1H), 3.77, 3.72 (AB of ABX, J$_{AB}$=11.0 Hz, J$_{AX}$=3.30 Hz, J$_{BX}$=3.70 Hz, 2H), 2.75-2.63 (m, 1H), 2.60-2.49 (m, 1H), 2.39-2.29 (m, 1H), 1.93-1.84 (m, 1H), 1.83-1.72 (m, 4H), 1.9-1.55 (m, 10H), 1.37-1.26 (m, 2H); $^{13}$C NMR: (75.4 MHz, CDCl$_3$) δ 142.4, 128.7, 128.5, 126.1, 84.6, 62.2, 41.8, 40.9, 33.9, 31.2, 30.6, 25.7, 23.9, 20.5; HRMS m/z (ESI): calcd. for C$_{16}$H$_{23}$NO$_3$Na [M+Na]$^+$300.1571. found 300.1560. Optical rotation: $[\alpha]^{rt}_D$-9.8 (c 1.23, CHCl$_3$).

Compound 2i

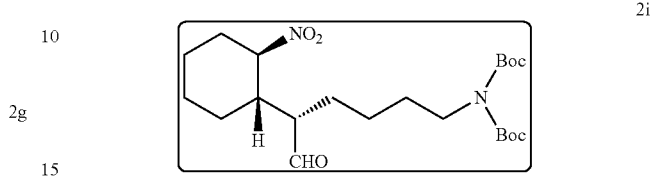

The product was obtained as a yellow oil following the standard procedure and purified by column chromatography. TLC R$_f$=0.65 (EtOAc/hexanes, v/v, 1:3). The enantiomeric excess was determined by HPLC of the alcohol derived from 2i using a Chiracel AD-H column, λ=220 nm, hexane/isopropanol (v/v: 95/5), flow rate=0.6 mL/min; t$_R$=15.2 min (major), 16.9 min (minor) (98% ee); $^1$H NMR: (299.7 MHz, CDCl$_3$) δ 9.70 (d, 1H, J=1.9 Hz), 4.86 (q, J=3.4 Hz, 1H), 3.54 (t, J=7.5 Hz, 2H), 2.55 (m, 1H), 2.31 (m, 1H), 2.11 (m, 1H), 1.88 (m, 1H), 1.77-1.54 (m, 10H), 1.50 (s, 18H), 1.37-1.1 (m, 8H), 0.86 (m, 4H); $^{13}$C NMR: (75.4 MHz, CDCl$_3$) δ 203.72, 152.98, 101.12, 83.67, 82.48, 52.54, 46.04, 38.26, 29.90, 29.38, 28.30, 26.78, 25.19, 23.67, 23.36, 20.38; HRMS m/z (ESI): calcd. for C$_{22}$H$_{38}$N$_2$O$_7$Na [M+Na]$^+$ 300.1571. found 300.1560. Optical rotation: $[\alpha]^{rt}_D$-9.8 (c 1.23, CHCl$_3$).

Cyclic γ-Amino Acid Synthesis Shown in Scheme 1-5 and Scheme 1-6:

Briefly, butyraldehyde was subjected to the stereoselective Michael reaction conditions. The crude reaction mixture was purified via SiO$_2$ column chromatography eluting with EtOAc/hexane to give the desired α-substituted-γ-nitroaldehyde (major diastereomer). Reduction of the aldehyde by using NaBH$_4$ (to avoid epimerization at C2), provides the δ-nitro alcohol product 5. Jones oxidation of 5 provided the γ-nitro-α-alkylbutyric acid 6, which was then transformed to protected cyclic γ-amino acid 7 in an efficient one-pot operation involving nitro group reduction followed by Boc protection.

Scheme 1-5. Synthesis of cyclic γ-Amino Acid

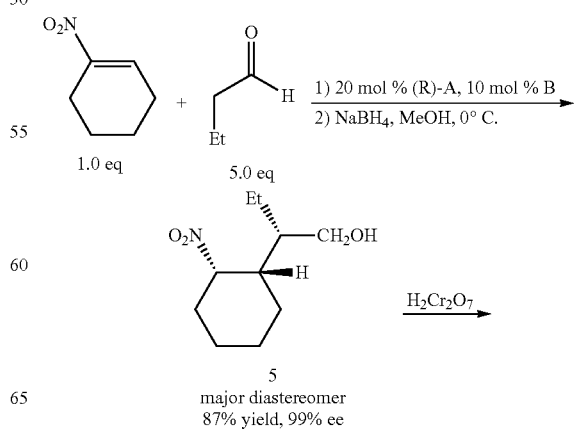

41

-continued

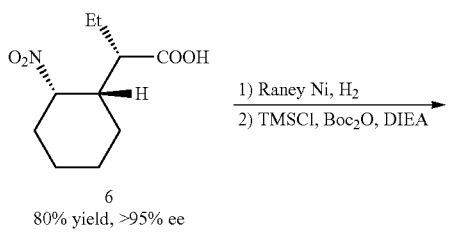

6
80% yield, >95% ee

1) Raney Ni, $H_2$
2) TMSCl, $Boc_2O$, DIEA
→

7
80% yield, >95% ee (S)-2-((1S,2S)-2-Nitrocyclohexyl)butanoic acid

6

To 6.1 mmol alcohol 5 dissolved in 60 mL acetone at 0° C. was added 9.1 mmol $H_2Cr_2O_7$ (18 mL Jones reagent). The mixture was stirred for 5 h, during which time the mixture warmed to room temperature. Excess isopropanol was added, and the mixture was stirred for 10 min. The mixture was filtered, and the solution was diluted with 40 mL 1 N HCl and extracted with $Et_2O$. Complete extraction of the product into the $Et_2O$ phase was monitored by TLC. The organic layers was washed with brine, dried over $MgSO_4$, filtered and concentrated to give a viscous oil, of which the desired product 5 (1.1 g, 5.1 mmol) was purified via column chromatography eluting with EtOAc/hexane (1:10 to 1:3; v/v) to give pure product as a yellow oil in 83% yield. TLC $R_f$=0.46 (EtOAc/hexanes, v/v, 1:1). $^1H$ NMR: (299.7 MHz, $CDCl_3$) δ 4.85 (q, J=3.5 Hz, 1H), 2.49 (ddd, J=10.3, 9.2, 4.2 Hz, 1H), 2.36 (m, 1H), 2.06-1.49 (m, 10H), 1.41-1.28 (m, 1H), 0.93 (t, J=7.5 Hz, 3H); $^{13}C$ NMR: (75.4 MHz, $CDCl_3$) δ 84.1, 48.2, 40.5, 30.7, 25.2, 23.4, 23.1, 20.2, 11.0; HRMS m/z (ESI): calcd. for $C_{10}H_{17}NO_4Na$ [M+Na]$^+$ 238.1050. found 238.1044. The ee of this compound (>95%) was determined by coupling one portion to L-Phe-OMe and another portion to D-Phe-OMe and then analyzing the products by $^1H$ NMR spectroscopy. Optical rotation: $[\alpha]^{rt}_D$+ 11.8 (c 1.74, $CHCl_3$).

42

(S)-2-((1S,2S)-2-(tert-butoxycarbonylamino)cyclohexyl)butanoic acid

7

γ-nitro acid 6 (1.1 g, 5.1 mmol) was dissolved in methanol (10 mL), and flask was flushed with $N_2$. To the flask was added Raney Nickle (0.1 g), and the flask was attached to a Parr apparatus and shaken for 24 hours at a $H_2$ pressure of 40 psi. The reaction mixture was filtered through a pad of celites and concentrated to give a white solid amino acid. The amino acid was suspended in anhydrous $CH_2Cl_2$ (20 mL) and stirred vigorously. TMSCl (1.29 mL, 10.2 mmol) was added in one portion and stirred at room temperature for 2 h. The mixture was cooled to 0° C., and DIEA (1.59 mL, 9.1 mmol) and $Boc_2O$ (1.7 g, 7.7 mmol) were added sequentially. The reaction was allowed to warm to room temperature and stirred for 12 h. The resulting mixture was concentrated to provide a yellow oil which was then dissolved in EtOAc (50 mL). To this mixture, water was added (20 mL), and the solution was acidified with 1 N HCl. The separated organic layer was dried ($MgSO_4$), filtered and concentrated to give a white solid. The desired Boc protected product 7 (1.1 g, 5.1 mmol) was purified via column chromatography eluting with EtOAc/hexane (1:10 to 1:1; v/v) to give pure product as a white solid in 80% yield. TLC $R_f$=0.3 (EtOAc/hexanes, v/v, 1:1). $^1H$ NMR: (299.7 MHz, $CD3OD$) δ 6.38 (d, 0.34H), 3.83 (bs, 1H), 2.24 (dt, J=9.8, 3.8 Hz, 1H), 1.84-1.64 (m, 5H), 1.55-1.2 (m, 14H), 1.36-1.18 (m, 2H), 0.925 (t, J=7.6 Hz, 3H); $^{13}C$ NMR: (75.4 MHz, $CD_3OD$) δ 78.7, 49.3, 49.0, 41.5, 31.4, 27.6, 25.5, 23.8, 22.7, 20.2, 10.6; HRMS m/z (ESI): calcd. for $C_{15}H_{27}NO_4Na$ [M+Na]$^+$ 308.1833. found 308.1831. Optical rotation: $[\alpha]^{rt}_D$+8.49 (c 0.73, $CHCl_3$).

Scheme 1-6. Synthesis of cyclic γ-Amino Acid

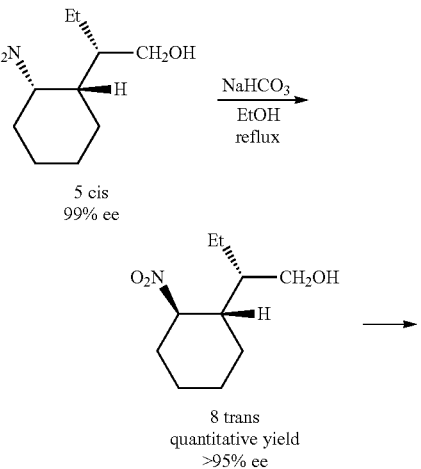

5 cis
99% ee

NaHCO$_3$
EtOH
reflux 8 trans
quantitative yield
>95% ee

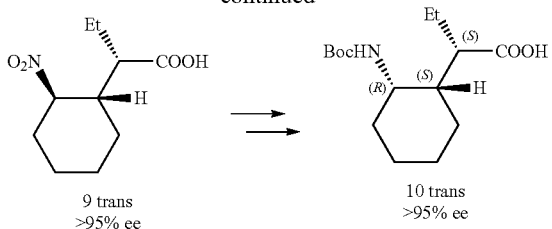

9 trans
>95% ee 10 trans
>95% ee (S)-2-((1S,2R)-2-Nitrocyclohexyl)butan-1-ol 8

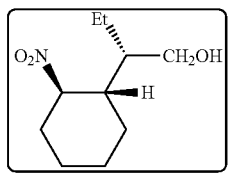

8

To a mixture of nitro alcohol 8 (2.05 g, 10 mmol) and sodium bicarbonate (8.4 g, 100 mmol) was added absolute ethanol (30 mL), and the mixture was refluxed for 4 hours. The mixture was filtered through celite and the filtrate was concentrated. The desired product 8 (2 g, 10 mmol) was purified via column chromatography eluting with EtOAc/hexane (1:10 to 1:1; v/v) to give pure product as a colorless oil in quantatitive yield. TLC $R_f$=0.54 (EtOAc/hexanes, v/v, 1:1). $^1$H NMR (300 MHz, CDCl$_3$) δ 4.52 (dt, J=11.6, 3.9 Hz, 1H), 3.68 3.45 (AB of ABX, $J_{AB}$=10.3 Hz, $J_{AX}$=4.50 Hz, $J_{BX}$=9.70 Hz, 2H), 2.35 (m, 1H), 2.25 (m, 1H), 1.97-1.74 (m, 4H), 1.48-1.24 (m, 5H), 1.07 (m, 2H), 0.929 (t, J=7.4, 3H); $^{13}$C NMR (75 MHz, CDCl$_3$) δ 88.92, 63.12, 43.24, 41.65, 32.61, 25.13, 24.70, 24.51, 19.24, 13.20; HRMS (ESI): calcd. for C$_{10}$H$_{19}$NO$_3$Na [M+Na]$^+$ 224.1258. found 224.1267. Optical rotation: $[\alpha]^{rt}_D$+28.55 (c 1.31, CHCl$_3$).

(S)-2-((1S,2R)-2-Nitrocyclohexyl)butanoic acid 9

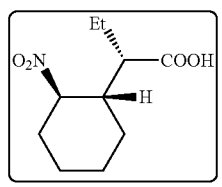

9

The product was obtained as a white solid following the procedure for preparing compound 6 and purified by column chromatography. TLC $R_f$=0.46 (EtOAc/hexanes, v/v, 1:1). $^1$H NMR (300 MHz, CDCl$_3$) δ 11.70 (1H), 4.49 (dt, J=4.0, 11.2 Hz, 1H), 2.50 (tt, J=3.4, 11.6 Hz, 1H), 2.27 (m, 2H), 1.87 (m, 4H), 1.67 (m, 1H), 1.48 (m, 1H) 1.29 (m, 3H), 0.95 (t, J=7.2 Hz, 3H); $^{13}$C NMR (75 MHz, CDCl$_3$) δ 180.55, 87.99, 48.10, 43.06, 32.20, 25.94, 24.81, 24.36, 18.85, 13.25; HRMS m/z (ESI): calcd. for C$_{10}$H$_{17}$Na$_4$Na [M+Na]$^+$ 238.1050. found 238.1044. Optical rotation: $[\alpha]^{rt}_D$+3.52 (c 2.33, CHCl$_3$).

(S)-2-((1S,2R)-2-(tert-butoxycarbonyl)cyclohexyl)butanoic acid 10

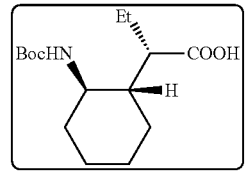

10

The product was obtained as a colorless oil following the procedure for preparing compound 7 and purified by column chromatography. TLC $R_f$=0.33 (EtOAc/hexanes, v/v, 1:1). $^1$H NMR (300 MHz, CDCl$_3$) (the broadness of the peaks and the presence of two NH peaks suggested that two interconverting rotamers were present) δ 11.58 (1H), 6.11 (d, J=10.1 Hz, 0.33 H), 4.50 (d, J=10.2 Hz, 0.65 H), 3.43, 3.21 (m, 1H, mixtures of rotamers), 2.48, 2.28 (m, 1H, mixtures of rotamers), 2.0-1.8 (m, 1H), 1.77-1.52 (m, 6H), 1.45 (s, 9H), 1.19 (m, 4H), 0.91 (t, J=6.9 Hz, 3H); $^{13}$C NMR (75 MHz, CDCl$_3$) (mixtures of rotamers) δ 182.26, (181.21), 157.34, (155.64), 79.44, (80.69), (55.29), 51.97, (49.48), 48.32, (46.69), 46.32, (45.12), 34.96, 28.59 (28.10), 27.23, 25.80, 25.70, (21.24), 19.35, 13.08, 12.48; HRMS m/z (ESI): calcd. for C$_{15}$H$_{27}$NO$_4$Na [M+Na]$^+$ 308.1833. found 308.1836. Optical rotation: $[\alpha]^{rt}_D$−5.99 (c 0.95, CHCl$_3$)

VI. Peptide Synthesis and Purification

Peptides 11 and 12 were synthesized by conventional solution phase methods using a fragment condensation strategy. The tert-butyloxycarbonyl group (Boc) was used for N-terminal protection, and the C-terminal was protected as a benzy ester (OBn). Deprotection at the N-terminus was performed using 4N HCl in dioxane, and hydrogenation was done to remove the C-terminal protecting groups.

Boc-protected amino acids, N,N-Diisopropylethylamine (DIEA), and coupling reagents (N,N-dimethylamino) propyl-3-ethylcarbodiimide hydrochloride (EDCI) and 1-hydroxybenzo-triazole (HOBt) were purchased from Sigma-Aldrich and Chem-Impex. X-ray quality crystals of 11 and 12 were grown from a chloroform/diethyl ether mixture and by evaporation of a CHCl$_3$/heptane mixture, respectively.

(Et)ACHA stands for cyclic gamma amino acid residue (R,R,R) which was synthesized by n-butanal and (S)-A in this section (peptide synthesis).

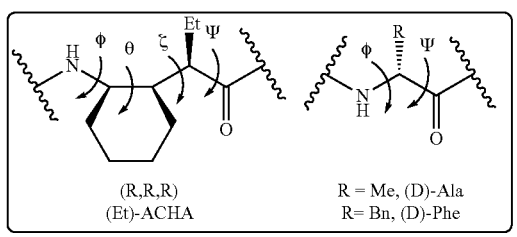

A. Synthesis of Boc-(D)Ala-(Et)ACHA-(D)Ala-(Et)ACHA-(D)Ala-(Et)ACHA-OBn (12)
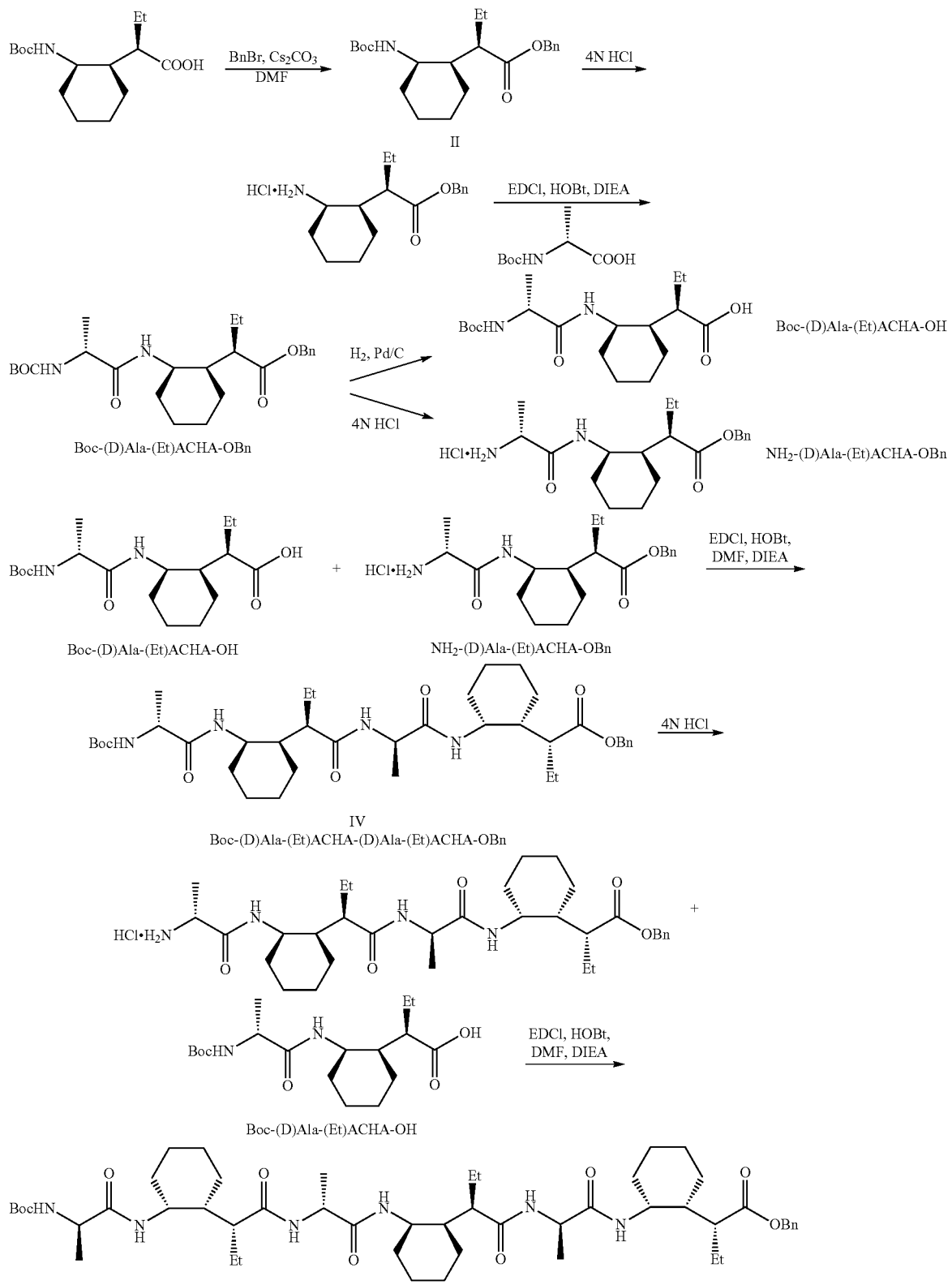

(1) Boc-(D)Ala-(Et)ACHA-OBn III.

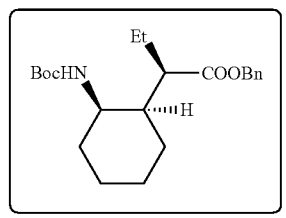

277 mg (0.97 mmol) of Boc-(Et)ACHA-OH and $Cs_2CO_3$ (316 mg, 0.97 mmol) were dissolved in DMF (10 mL). Benzyl bromide (140 μL, 1.16 mmol) was added. The mixture was stirred at the room temperature for overnight. The mixture was diluted with ethyl acetate (50 mL) and washed with saturated aqueous $NaHCO_3$ and brine. The organic layers were collected, dried over $MgSO_4$ and filtered. The filtrate was concentrated to give the crude product, which was purified via column chromatography eluting with EtOAc/hexane to give the desired benzyl ester Boc-(Et)ACHA-OBn II as an oil. TLC $R_f$=0.53 (EtOAc/hexanes, v/v, 1:3). $^1$H NMR (300 MHz, $CDCl_3$) δ 11.70 (1H), 4.49 (dt, J=4.0, 11.2 Hz, 1H), 2.50 (tt, J=3.4, 11.6 Hz, 1H), 2.27 (m, 2H), 1.87 (m, 4H), 1.67 (m, 1H), 1.48 (m, 1H) 1.29 (m, 3H), 0.95 (t, J=7.2 Hz, 3H); $^{13}$C NMR (75 MHz, $CDCl_3$) δ 175.78, 155.42, 136.53, 128.62, 128.44, 128.16, 79.23, 66.34, 48.57, 41.47, 31.20, 28.63, 28.31, 25.05, 24.93, 23.19, 21.28, 11.59; HRMS m/z (ESI): calcd. for: $C_{22}H_{33}NO_4Na$ $[M+Na]^+$ 398.2302. found 398.2306. Optical rotation: $[α]^{rt}_D$–20 (c 6.29, $CHCl_3$).

The white solid Boc-(Et)ACHA-OBn was dissolved in 4N HCl in dioxane (10 mL) and stirred for three hours at room temperature. The solvent was blown off under a stream of $N_2$. The residue was placed under high vacuum for one hour and carried on without further purification ($HCl.NH_2$-(Et)ACHA-OBn).

Boc-(D)Ala-(Et)ACHA-OBn III:

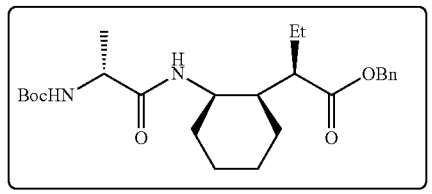

Boc-(D)-Ala-OH (284 mg, 1.5 mmol) was added directly to a solution of $HCl.NH_2$-(Et)ACHA-OBn (468 mg, 1.5 mmol), EDCI (345 mg, 1.8 mmol), HOBt (243 mg, 1.8 mmol), and N,N-Diisopropylethylamine (392 μL, 2.25 mmol) in $CH_2Cl_2$ (10 mL). The resulting solution was stirred for one day at room temperature. The reaction mixture was diluted with excess amount of EtOAc, washed with aqueous 10% citric acid, aqueous saturated $NaHCO_3$ and brine. The organic layer was dried over $MgSO_4$, filtered and concentrated to give the desired amide, which was purified via column chromatography to yield 636 mg (95% yield) peptide Boc-(D)Ala-(Et)ACHA-OBn as white foam. TLC $R_f$=0.52 (EtOAc/hexanes, v/v, 1:1). $^1$H NMR (300 MHz, $CDCl_3$) δ 7.37-7.29 (m, 5H), 6.66 (br, 1H), 4.99, 5.20 (AB, $J_{AB}$=12.3 Hz, 2H), 4.99 (br, 1H), 4.14 (m, 1H), 4.07 (p, J=7.2 Hz, 1H), 2.28 (ddd, J=4.2, 9.9, 9.9 Hz, 1H), 1.89-1.62 (m, 6H), 1.52 (m, 2H) 1.44 (s, 9H), 1.27 (m, 1H), 1.23 (m, 1H), 1.24 (d, J=7.1 Hz, 3H), 1.07 (m, 1H), 0.83 (t, J=7.3 Hz, 3H); $^{13}$C NMR (75 MHz, $CDCl_3$) δ 175.55, 171.91, 156.13, 136.37, 128.60, 128.22, 80.26, 77.68, 77.26, 76.83, 66.50, 50.12, 49.63, 46.77, 41.52, 31.11, 28.52, 25.70, 24.82, 23.29, 20.63, 17.40, 11.65; HRMS m/z (ESI): calcd. for: $C_{25}H_{38}N_2O_5Na$ $[M+Na]^+$ 469.2673. found 469.2672.

(2) Boc-(D)Ala-(Et)ACHA-OH.

Boc-(D)Ala-(Et)ACHA-OBn (300 mg, 0.67 mmol) was dissolved in methanol (10 mL), and flask was flushed with $N_2$. To the flask was added Pd/C 10% (0.05 g), and the flask was attached to a Parr apparatus and shaken for 6~7 hours at a $H_2$ pressure of 10 psi. The reaction mixture was filtered through a pad of celite diatomaceous earth and concentrated to give a white solid (Boc-(D)Ala-(Et)ACHA-OH) (226 mg, 95%). The crude product was carried on without further purification.

(3) $HCl.NH_2$-(D)Ala-(Et)ACHA-OBn.

The white solid Boc-(D)Ala-(Et)ACHA-OBn (336 mg, 0.75 mmol) was dissolved in 4N HCl in dioxane (10 mL) and stirred for three hours at room temperature. The solvent was blown off under a stream of $N_2$. The residue was placed under high vacuum for one hour and carried on without further purification ($HCl.NH_2$-(D)Ala-(Et)ACHA-OBn).

(4) Boc-(D)Ala-(Et)ACHA-(D)Ala-(Et)ACHA-OBn IV.

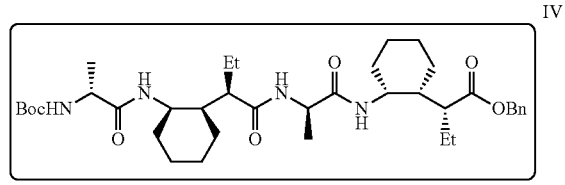 [SMILES: CC[C@@H](C(=O)N[C@H](C)C(=O)N[C@@H]1CCCC[C@@H]1[C@@H](CC)C(=O)OCc1ccccc1)[C@H]1CCCC[C@H]1NC(=O)[C@@H](C)NC(=O)OC(C)(C)C]

Boc-(D)Ala-(Et)ACHA-OH (178 mg, 0.5 mmol) was added directly to a solution of $HCl.NH_2$-(D)Ala-(Et)ACHA-OBn (191 mg, 0.5 mmol), EDCI (115 mg, 0.6 mmol), HOBt (67.5 mg, 0.6 mmol), and DIEA (105 μL, 0.6 mmol) in DMF (5 mL). The resulting solution was stirred for two days at room temperature. The reaction mixture was diluted with excess amount of EtOAc, washed with aqueous 10% citric acid, aqueous saturated $NaHCO_3$ and brine. The organic layer was dried over $MgSO_4$, filtered and concentrated to give the desired peptide, which was purified via column chromatography to yield peptide Boc-(D)Ala-(Et)ACHA-(D)Ala-(Et)ACHA-OBn as a white solid (308 mg, 90% yield). $^1$H NMR (300 MHz, $CDCl_3$) δ 7.52 (d, J=7.4 Hz, 1H), 7.40-7.25 (m, 5H), 7.20 (d, J=9.5 Hz, 1H), 5.23, 4.99 (AB, $J_{AB}$=12.2 Hz, 2H), 4.92 (d, J=5.6 Hz, 1H), 4.36 (dq, J=7.0, 7.0 Hz, 1H), 4.25 (m, 1H), 4.08 (dq, J=1.4, 7.0 Hz, 1H), 4.0 (m, 1H), 2.29 (ddd, 9.8, 9.8, 3.9 Hz 1H), 1.91-1.61 (m, 9H), 1.55-1.1 (m, 29H), 0.85-0.78 (m, 6H); $^{13}$C NMR (75 MHz, $CDCl_3$) δ 175.76, 175.68, 172.32, 171.63, 156.17, 136.64, 128.70, 128.52, 128.05, 80.87, 66.41, 51.36, 50.44, 49.81, 49.39, 47.15, 46.64, 42.96, 41.73, 31.33, 31.06, 28.51, 25.97, 25.90, 24.65, 24.32, 23.25, 22.51, 20.85, 20.50, 17.80, 17.34, 12.12, 11.60; HRMS m/z (ESI): calcd. for $C_{38}H_{60}N_4O_7Na$ $[M+Na]^+$ 707.9217. found 707.9227.

(5) $HCl.NH_2$-(D)Ala-(Et)ACHA-(D)Ala-(Et)ACHA-OBn.

The white solid Boc-(D)Ala-(Et)ACHA-(D)Ala-(Et)ACHA-OBn (116 mg, 0.17 mmol) was dissolved in 4N HCl in dioxane (5 mL) and stirred for three hours at room temperature. The solvent was blown off under a stream of $N_2$. The residue was placed under high vacuum for one hour and carried on without further purification ($HCl.NH_2$-(D)Ala-(Et)ACHA-(D)Ala-(Et)ACHA-OBn).

(6) Boc-(D)Ala-(Et)ACHA-(D)Ala-(Et)ACHA-(D)Ala-(Et)ACHA-OBn 12.

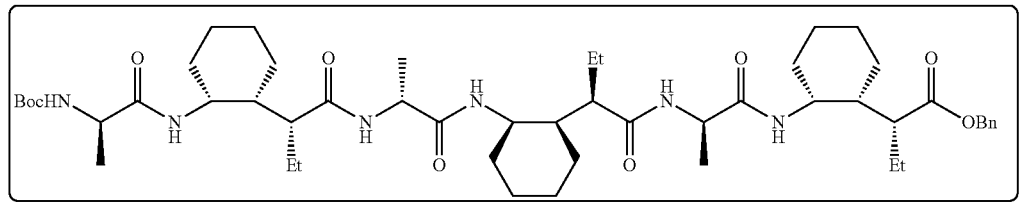

Boc-(D)Ala-(Et)ACHA-OH (55 mg, 0.154 mmol) was added directly to a solution of amine (HCl.NH$_2$-(D)Ala-(Et)ACHA-(D)Ala-(Et)ACHA-OBn) (96 mg, 0.154 mmol), EDCI (36 mg, 0.185 mmol), HOBt (25 mg, 0.185 mmol), and DIEA (40 μL, 0.23 mmol) in DMF (2 mL). The resulting solution was stirred for two days at room temperature. The reaction mixture was diluted with excess amount of EtOAc, washed with aqueous 10% citric acid, aqueous saturated NaHCO$_3$ and brine. The organic layer was dried over MgSO$_4$, filtered and concentrated to give the desired peptide, which was purified via column chromatography to yield 137 mg (92% yield) peptide Boc-(D)Ala-(Et)ACHA-(D)Ala-(Et)ACHA-(D)Ala-(Et)ACHA-OBn as a white solid. $^1$H NMR (300 MHz, CDCl$_3$) δ 8.01 (d, J=8.00 Hz, 1H), 7.92 (d, J=9.4 Hz, 1H), 7.69 (d, J=9.8 Hz, 1H), 7.42-7.22 (m, 5H), 6.99 (d, J=2.1 Hz, 1H), 6.60 (d, J=9.9 Hz, 1H), 5.28, 5.02 (AB, J$_{AB}$=12.6 Hz, 2H), 4.32 (m, 1H), 4.22 (m, 2H), 4.02 (m, 3H), 2.42 (ddd, 10.0, 10.0, 3.5 Hz 1H), 1.98-1.16 (m, 45H), 0.88-0.71 (m, 18H); $^{13}$C NMR (75 MHz, CDCl$_3$) δ 176.61, 175.96, 175.78, 172.66, 172.59, 172.35, 156.58, 137.14, 128.64, 128.42, 127.78, 81.62, 66.16, 52.94, 52.78, 51.37, 50.62, 50.46, 48.72, 47.01, 46.76, 46.65, 42.39, 42.21, 41.72, 31.94, 31.81, 31.39, 29.91, 28.53, 26.46, 26.30, 25.69, 24.88, 24.28, 23.54, 23.06, 22.81, 22.31, 20.80, 20.57, 20.16, 18.19, 18.02, 16.70, 12.48, 11.53, 11.37; HRMS m/z (ESI): calcd. for C$_{51}$H$_{83}$N$_6$O$_9$ [M+H]$^+$ 923.6217. found 923.6227.

B. Synthesis of Boc-(Et)ACHA-(D)Phe-(Et)ACHA-(D)Phe-OMe (11)

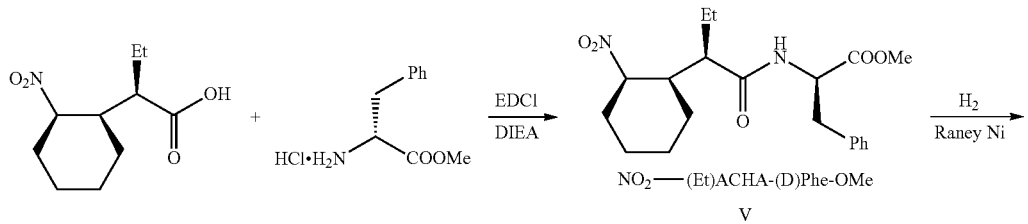

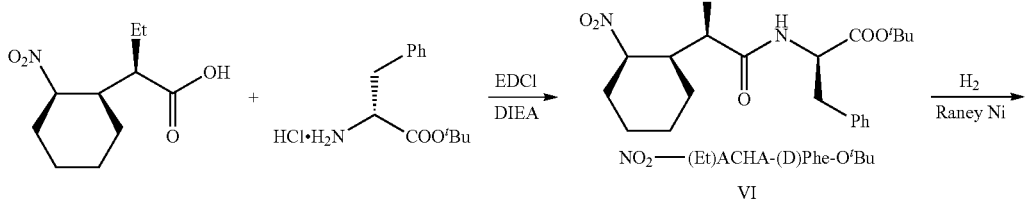

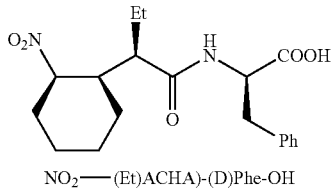

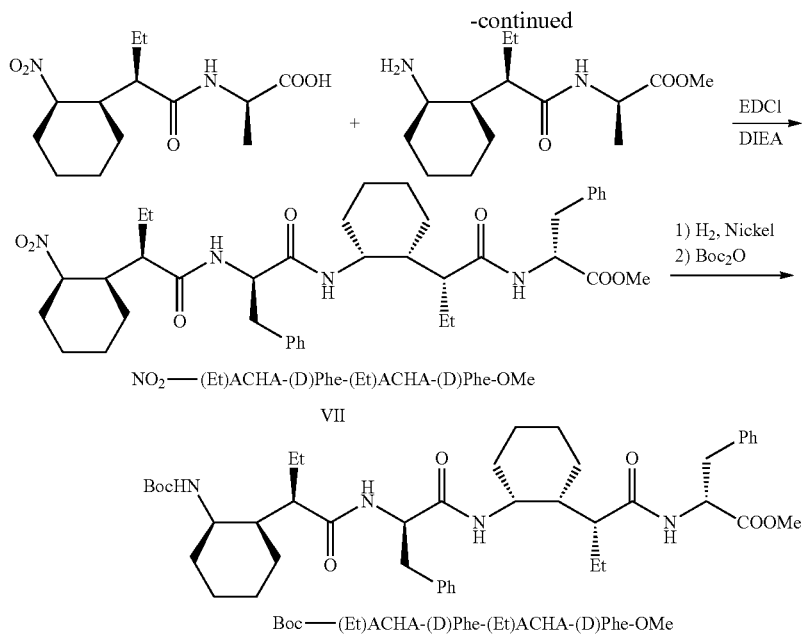

NO₂—(Et)ACHA-(D)Phe-(Et)ACHA-(D)Phe-OMe

VII

Boc—(Et)ACHA-(D)Phe-(Et)ACHA-(D)Phe-OMe

11

(1) NO₂-(Et)ACHA-(D)Phe-OMe V.

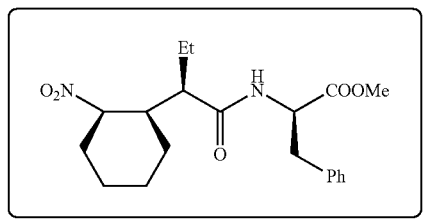

V

Nitro acid (215 mg, 1 mmol) was added directly to a solution of HCl.NH₂-Phe-OMe (238 mg, 1.1 mmol), EDCI (240 mg, 1.2 mmol), HOBt (170 mg, 1.2 mmol), and DIEA (275 μL, 1.5 mmol) in CH₂Cl₂ (10 mL). The resulting solution was stirred for one day at room temperature. The reaction mixture was diluted with excess amount of EtOAc, washed with aqueous 10% citric acid, aqueous saturated NaHCO₃ and brine. The organic layer was dried over MgSO₄, filtered and concentrated to give the desired product, which was purified via column chromatography to yield peptide NO₂-(Et)ACHA-(D)Phe-OMe as an oil (312 mg, 83% yield). TLC $R_f$=0.54 (EtOAc/hexanes, v/v, 1:1). $^1$H NMR (300 MHz, CDCl₃) δ 7.32-7.13 (m, 5H), 5.93 (d, J=8.4 Hz, 1H), 4.88 (dt, J=5.4, 8.2 Hz, 1H), 4.76 (q, J=3.4 Hz, 1H), 3.72 (s, 3H), 3.18, 2.98 (AB of ABX, $J_{AB}$=14.1 Hz, $J_{AX}$=5.4 Hz, $J_{BX}$=8.1 Hz, 2H), 2.39 (m, 1H), 2.19 (dt, J=3.9, 10.4 Hz, 1H), 1.96-1.22 (m, 10H), 0.63 (t, J=7.4 Hz, 3H); $^{13}$C NMR (75 MHz, CDCl₃) δ 174.49, 171.86, 136.11, 129.29, 129.19, 128.91, 127.37, 84.33, 53.22, 52.63, 52.56, 50.90, 42.55, 37.98, 30.91, 25.51, 23.64, 20.52, 11.58; HRMS m/z (ESI): calcd. C20H28N2O5Na for [M+H]⁺ 399.1891. found 399.1898.

(2) NH₂-(Et)ACHA-(D)Phe-OMe.

NO₂-(Et)ACHA-(D)Phe-OMe (312 mg, 0.83 mmol) was dissolved in methanol (10 mL), and flask was flushed with N₂. To the flask was added Raney Nickle (0.05 g), and the flask was attached to a Parr apparatus and shaken for 16 hours at a H₂ pressure of 40 psi. The reaction mixture was filtered through a pad of celites and concentrated to give a white solid NH₂-(Et)ACHA-(D)Phe-OMe (259 mg, 90%). The crude product was carried on without further purification.

(3) NO₂-(Et)ACHA-(D)Phe-O$^t$Bu VI.

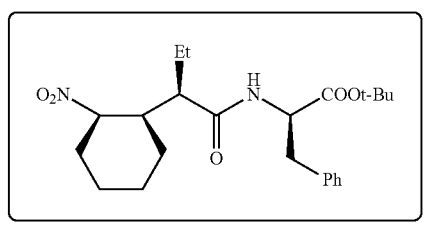

VI

Nitro acid (345 mg, 1.6 mmol) was added directly to a solution of HCl.NH₂-Phe-O$^t$Bu (464 mg, 1.8 mmol), EDCI (368 mg, 1.92 mmol), HOBt (260 mg, 1.92 mmol), and DIEA (418 μL, 2.4 mmol) in CH₂Cl₂ (10 mL). The resulting solution was stirred for one day at room temperature. The reaction mixture was diluted with excess amount of EtOAc, washed with aqueous 10% citric acid, aqueous saturated NaHCO₃ and brine. The organic layer was dried over MgSO₄, filtered and concentrated to give the desired product, which was purified via column chromatography to yield peptide NO₂-(Et)ACHA-(D)Phe-O$^t$Bu as an oil (569 mg, 85% yield). TLC $R_f$=0.54 (EtOAc/hexanes, v/v, 1:1). $^1$H NMR (300 MHz, CDCl₃) δ 7.30-7.16 (m, 5H), 6.03 (d, J=7.5 Hz, 1H), 4.76 (q, J=3.4 Hz, 1H), 4.74 (m, 1H), 3.08, 3.01 (AB of ABX, $J_{AB}$=14.1 Hz, $J_{AX}$=6.3 Hz, $J_{BX}$=7.2 Hz, 2H), 2.36 (m, 1H), 2.17 (dt, J=3.8, 10.4 Hz, 1H), 1.98-1.08 (m, 19H), 0.71 (t, J=7.4 Hz, 3H); $^{13}$C NMR (75 MHz, CDCl₃)

δ 174.14, 170.40, 136.45, 129.48, 128.65, 127.14, 84.36, 82.45, 53.99, 50.77, 42.36, 38.51, 30.75, 28.07, 25.50, 23.65, 23.56, 20.45, 11.65; HRMS m/z (ESI): calcd. $C_{23}H_{35}N_2O_5$ for [M+H]$^+$ 419.2541. found 419.2536.

(4) NO$_2$-(Et)ACHA-(D)Phe-OH.

The white solid NO$_2$-(Et)ACHA-(D)Phe-O$^t$Bu. (418 mg, 1.0 mmol) was dissolved in 4N HCl in dioxane (10 mL) and stirred for three hours at room temperature. The solvent was blown off under a stream of N$_2$. The residue was placed under high vacuum for one hour and carried on without further purification NO$_2$-(Et)ACHA-(D)Phe-OH.

(5) NO$_2$-(Et)ACHA-(D)Phe-(Et)ACHA-(D)Phe-OMe.

NO$_2$-(Et)ACHA-(D)Phe-OH (259 mg, 0.75 mmol) was added directly to a solution of NH$_2$-(Et)ACHA-(D)Phe-OMe (268 mg, 0.77 mmol), EDCI (115 mg, 0.91 mmol), and DIEA (190 µL, 1.05 mmol) in CH$_2$Cl$_2$ (8 mL). The resulting solution was stirred for two days at room temperature. The reaction mixture was diluted with excess amount of EtOAc, washed with aqueous 10% citric acid, aqueous saturated NaHCO$_3$ and brine. The organic layer was dried over MgSO$_4$, filtered and concentrated to give the desired peptide, which was purified via column chromatography to yield 415 mg (80% yield) peptide NO$_2$-(Et)ACHA-(D)Phe-(Et)ACHA-(D)Phe-OMe.

(6) Boc-(Et)ACHA-(D)Phe-(Et)ACHA-(D)Phe-OMe 11.

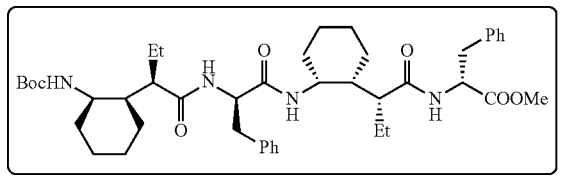

11

NO$_2$-(Et)ACHA-(D)Phe-(Et)ACHA-(D)Phe-OMe (138 mg, 0.20 mmol) was dissolved in methanol (10 mL), and flask was flushed with N$_2$. To the flask was added Raney Nickle (0.05 g), and the flask was attached to a Parr apparatus and shaken for 24 hours at a H$_2$ pressure of 40 psi. The reaction mixture was filtered through a pad of celites and concentrated to give a white solid NH$_2$-(Et)ACHA-(D)Phe-OMe (118 mg, 90%). The crude product was dissolved in CH$_2$Cl$_2$. Boc$_2$O (60 mg, 0.27 mmol) and DIEA (47 µL, 0.27 mmol) was added. The resulting solution was stirred for 5 hours at room temperature. The reaction mixture was diluted with excess amount of EtOAc, washed with aqueous saturated NaHSO$_4$ and brine. The organic layer was dried over MgSO$_4$, filtered and concentrated to give the desired peptide, which was purified via column chromatography to yield 108 mg (80% yield) peptide Boc-(Et)ACHA-(D)Phe-(Et)ACHA-(D)Phe-OMe 11 as a white solid. $^1$H NMR (300 MHz, CDCl$_3$) δ 7.72 (d, J=7.4 Hz, 1H), 7.32-7.15 (m, 12H), 6.54 (d, J=6.7 Hz, 1H), 4.81 (m, 2H), 4.55 (m, 1H), 4.27 (d, J=8.4 Hz, 1H), 3.75 (s, 3H), 3.30, 2.96 (AB of ABX, $J_{AB}$=14.3 Hz, $J_{AX}$=4.6 Hz, $J_{BX}$=9.9 Hz, 2H), 3.19, 3.10 (AB of ABX, $J_{AB}$=13.7 Hz, $J_{AX}$=6.5 Hz, $J_{BX}$=8.4 Hz, 2H), 1.89-0.86 (m, 33H) 0.54 (t, J=7.5 Hz, 3H), 0.42 (t, J=7.3 Hz, 3H); $^{13}$C NMR (75 MHz, CDCl$_3$) δ 177.00, 174.96, 172.29, 171.03, 156.26, 137.38, 129.44, 128.99, 128.73, 128.20, 126.89, 126.49, 79.87, 55.89, 54.26, 52.13, 50.42, 50.32, 48.36, 47.32, 43.04, 42.01, 38.13, 37.47, 31.52, 31.17, 28.39, 25.92, 25.68, 23.48, 23.10, 22.35, 20.32, 20.08, 11.69, 11.48; HRMS m/z (ESI): calcd. for $C_{44}H_{65}N_4O_7$ [M+H]$^+$ 761.4848. found 761.4858.

Crystallographic Experimental Section.

Data Collection for Hexamer 12.

A colorless crystal with approximate dimensions 0.29× 0.18×0.14 mm3 was selected under oil under ambient conditions and attached to the tip of a MiTeGen MicroMount® tip. The crystal was mounted in a stream of cold nitrogen at 100(2) K and centered in the X-ray beam by using a video camera. The crystal evaluation and data collection were performed on a Bruker SMART APEXII diffractometer with Cu Kα(λ=1.54178 Å) radiation and the diffractometer to crystal distance of 4.03 cm.

The initial cell constants were obtained from three series of scans at different starting angles. Each series consisted of 41 frames collected at intervals of 0.6° in a 25° range about with the exposure time of 5 seconds per frame. The reflections were successfully indexed by an automated indexing routine built in the APEXII program. The final cell constants were calculated from a set of 9946 strong reflections from the actual data collection.

The data were collected by using the full sphere data collection routine to survey the reciprocal space to the extent of a full sphere to a resolution of 0.82 Å. A total of 46372 data were harvested by collecting 19 sets of frames with 0.7° scans in with an exposure time 5-15 sec per frame. These highly redundant datasets were corrected for Lorentz and polarization effects. The absorption correction was based on fitting a function to the empirical transmission surface as sampled by multiple equivalent measurements (Bruker-AXS. (2007) APEX2, SADABS, and SAINT Software Reference Manuals. Bruker-AXS, Madison, Wis., USA).

Structure Solution and Refinement.

The systematic absences in the diffraction data were consistent for the space groups P2$_1$ that yielded chemically reasonable and computationally stable results of refinement (Sheldrick, G. M. (2008) SHELXL. *Acta Cryst.* A64, 112-122).

A successful solution by the direct methods provided most non-hydrogen atoms from the E-map. The remaining non-hydrogen atoms were located in an alternating series of least-squares cycles and difference Fourier maps. Non-hydrogen non-disordered atoms were refined with anisotropic displacement coefficients. Atoms C44-C51 were disordered over two positions with the major component occupied 78.2(3)% of the time. The disordered atoms were refined isotropically with restraints and constraints. Hydrogen atoms on the carbon atoms were included in the structure factor calculation at idealized positions and were allowed to ride on the neighboring atoms with relative isotropic displacement coefficients. The H atoms on the N and O atoms were located in the difference map and their positions were refined independently.

There are also two water molecules per foldamer in the lattice. The water molecules were refined with an idealized geometry (see Dolomanov et al., *J. Appl. Cryst.* (2009) 42, 339-341). The absolute configuration was assigned from synthesis but is also confirmed independently, all chiral centers are R. The final least-squares refinement of 611 parameters against 10465 data resulted in residuals R (based on F2 for I≥2σ) and wR (based on F2 for all data) of 0.0436 and 0.1087, respectively. The final difference Fourier map was featureless. The molecular diagrams are drawn with 40% probability ellipsoids.

TABLE 1-1

Crystal data and structure refinement for hexamer 12 (gellman117).

| | |
|---|---|
| Identification code | gellman117 |
| Empirical formula | $C_{51}H_{82}N_6O_9 \cdot 2\ H_2O$ |
| Formula weight | 959.26 |
| Temperature | 100(2) K |
| Wavelength | 1.54178 Å |
| Crystal system | Monoclinic |
| Space group | $P2_1$ |
| Unit cell dimensions | a = 14.5595(15) Å   α = 90° |
| | b = 12.4587(13) Å   β = 97.105(3)°. |
| | c = 15.6241(17) Å   γ = 90°. |
| Volume | 2812.3(5) Å$^3$ |
| Z | 2 |
| Density (calculated) | 1.133 Mg/m3 |
| Absorption coefficient | 0.642 mm$^{-1}$ |
| F(000) | 1044 |
| Crystal size | 0.29 × 0.18 × 0.14 mm$^3$ |
| Theta range for data collection | 2.85 to 71.46°. |
| Index ranges | −15 <= h <= 17, −15 <= k <= 15, −19 <= l <= 19 |
| Reflections collected | 46372 |
| Independent reflections | 10465 [R(int) = 0.0289] |
| Completeness to theta = 67.00° | 97.7% |
| Absorption correction | Empirical with SADABS |
| Max. and min transmission | 0.9155 and 0.8373 |
| Refinement method | Full-matrix least-squares on $F^2$ |
| Data/restraints/parameters | 10465/8/611 |
| Goodness-of-fit on $F^2$ | 1.025 |
| Final R indices [I > 2sigma(I)] | R1 = 0.0436, wR2 = 0.1065 |
| R indices (all data) | R1 = 0.0464, wR2 = 0.1087 |
| Absolute structure parameter | −0.03(14) |
| Largest diff. peak and hole | 0.369 and −0.356 e.Å$^{-3}$ |

Data Collection for Tetramer 11.

A colorless crystal with approximate dimensions 0.56× 0.31×0.28 mm3 was selected under oil under ambient conditions and attached to the tip of a MiTeGen MicroMount® tip. The crystal was mounted in a stream of cold nitrogen at 100(1) K and centered in the X-ray beam by using a video camera. The crystal evaluation and data collection were performed on a Bruker SMART APEXII diffractometer with Cu Kα (λ=1.54178 Å) radiation and the diffractometer to crystal distance of 4.03 cm.

The initial cell constants were obtained from three series of scans at different starting angles. Each series consisted of 41 frames collected at intervals of 0.6° in a 25° range about with the exposure time of 10 seconds per frame. The reflections were successfully indexed by an automated indexing routine built in the APEXII program. The final cell constants were calculated from a set of 9995 strong reflections from the actual data collection.

The data were collected by using the full sphere data collection routine to survey the reciprocal space to the extent of a full sphere to a resolution of 0.83 Å. A total of 35684 data were harvested by collecting 19 sets of frames with 0.6° scans in with an exposure time 10-20 sec per frame. These highly redundant datasets were corrected for Lorentz and polarization effects. The absorption correction was based on fitting a function to the empirical transmission surface as sampled by multiple equivalent measurements.

Structure Solution and Refinement.

The systematic absences in the diffraction data were consistent for the space groups $P2_1$ and $P2_1/m$. The E-statistics strongly suggested the non-centrosymmetric space group $P2_1$ that yielded chemically reasonable and computationally stable results of refinement, as referenced above.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. Hydrogen residing on carbon atoms were included in the structure factor calculation at idealized positions and were allowed to ride on the neighboring atoms with relative isotropic displacement coefficients. The amide H atoms were found in the difference map and refined independently. The chiral centers were R.

The final least-squares refinement of 519 parameters against 7776 data resulted in residuals R (based on F2 for I≥2σ) and wR (based on F2 for all data) of 0.0270 and 0.0708, respectively. The final difference Fourier map was featureless. The molecular diagram is drawn with 40% probability ellipsoids.

TABLE 1-2

Crystal data and structure refinement for tetramer 11 (gellman118).

| | |
|---|---|
| Identification code | gellman118 |
| Empirical formula | $C_{44}H_{64}N_4O_7$ |
| Formula weight | 760.99 |
| Temperature | 100(1) K |
| Wavelength | 1.54178 Å |
| Crystal system | Monoclinic |
| Space group | $P2_1$ |
| Unit cell dimensions | a = 10.770(3) Å   α = 90°. |
| | b = 17.053(5) Å   β = 99.878(19)°. |
| | c = 11.738(4) Å   γ = 90°. |
| Volume | 2123.8(11) Å$^3$ |
| Z | 2 |
| Density (calculated) | 1.190 Mg/m3 |
| Absorption coefficient | 0.642 mm$^{-1}$ |
| F(000) | 824 |
| Crystal size | 0.56 × 0.31 × 0.28 mm$^3$ |
| Theta range for data collection | 3.82 to 72.20°. |
| Index ranges | −13 <= h <= 13, −21 <= k <= 19, −14 <= l <= 14 |
| Reflections collected | 35684 |
| Independent reflections | 7776 [R(int) = 0.0201] |
| Completeness to theta = 67.00° | 100.0% |
| Absorption correction | Empirical with SADABS |
| Max. and min transmission | 0.8382 and 0.7139 |
| Refinement method | Full-matrix least-squares on $F^2$ |
| Data/restraints/parameters | 7776/1/519 |
| Goodness-of-fit on $F^2$ | 1.038 |
| Final R indices [I > 2sigma(I)] | R1 = 0.0270, wR2 = 0.0706 |
| R indices (all data) | R1 = 0.0272, wR2 = 0.0708 |
| Absolute structure parameter (Flack x) | −0.05(9) |
| Absolute structure parameter (Hooft y) | −0.01(3) |
| Largest diff. peak and hole | 0.190 and −0.152 e.Å$^{-3}$ |

TABLE 1-3

Hydrogen bonds for hexamer 12(gellman117) [Å and °].

| D—H . . . A | d(D—H) | d(H . . . A) | d(D . . . A) | <(DHA) |
|---|---|---|---|---|
| O(10)—H(10A) . . . O(7) | 0.851(2) | 2.061(17) | 2.837(2) | 151(3) |
| O(10)—H(10B) . . . O(11) | 0.852(2) | 2.039(10) | 2.875(4) | 167(4) |
| O(11)—H(11B) . . . O(6) | 0.851(2) | 2.62(6) | 2.781(3) | 92(4) |
| O(11)—H(11A) . . . O(8)#1 | 0.851(2) | 2.40(5) | 2.857(3) | 115(4) |
| N(1)—H(1) . . . O(7)#2 | 0.77(3) | 2.11(3) | 2.879(2) | 173(3) |
| N(3)—H(3) . . . O(2) | 0.84(3) | 2.10(3) | 2.936(2) | 173(2) |
| N(4)—H(4) . . . O(3) | 0.87(3) | 2.01(3) | 2.875(2) | 173(2) |
| N(5)—H(5) . . . O(4) | 0.83(3) | 2.05(3) | 2.882(2) | 175(2) |
| N(6)—H(6) . . . O(5) | 0.88(3) | 1.97(3) | 2.850(2) | 178(2) |

Symmetry transformations used to generate equivalent atoms:
1 −x, y + ½, −z + 1
2 x + 1, y, z

TABLE 1-4

Hydrogen bonds for tetramer 11(gellman118) [Å and °].

| D—H...A | d(D—H) | d(H...A) | d(D...A) | <(DHA) |
|---|---|---|---|---|
| N(4)—H(4)...O(3) | 0.862(17) | 2.076(17) | 2.9331(15) | 172.3(15) |
| N(3)—H(3)...O(2) | 0.831(16) | 2.264(16) | 3.0466(16) | 157.2(14) |
| N(1)—H(1)...O(5)#1 | 0.840(17) | 2.341(17) | 3.1780(16) | 173.8(14) |

Symmetry transformations used to generate equivalent atoms:
1x + 1, y, z

Two-Dimensional NMR Analysis.

Scheme 1-7. Characteristic NOEs patterns observed for the 1:1 α/γ-peptide hexamer in CDCl3.

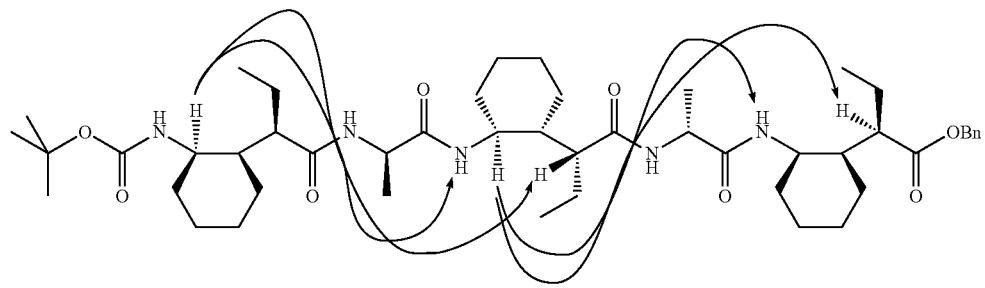

Boc-Ala(01)-EtCyHex (02)-Ala(03)-EtCyHex(04)-Ala(05)-EtCyHex(06)-OBn

EtCyHex refer to cyclic gamma amino acid residue (R,R,R), which was synthesized by n-butanal and (S)-A as described in this section.

TABLE 1-5

NMR Chemical Shift Data (ppm).

| Residue Number | NH | α | β | γ | Unassigned |
|---|---|---|---|---|---|
| N-Terminus | | 0.844 | | | |
| Ala-1 | 5.077 | 3.939 | 1.311 | | |
| EtCyhex-2 | 6.617 | 1.865 | 1.646 | 4.056 | 1.824, 1.751, 1.656, 1.402, 1.309 |
| Ala-3 | 7.076 | 4.000 | 1.369 | | |
| EtCyhex-4 | 7.797 | 1.919 | 1.66 | 4.194 | 1.791, 1.681, 1.644, 1.593, 1.416, 1.176, 1.388 |
| Ala-5 | 8.153 | 4.234 | 1.365 | | |
| EtCyhex-6 | 8.065 | 2.423 | 1.979 | 4.329 | 1.852, 1.841, 1.763, 1.683, 1.499, 1.453, 1.225 |
| C-Terminus | CH$_2$ = 5.021, 5.288 | O = 7.73, M = 7.409, P = 7.327 | | | |

NMR Acquisitions:

NMR samples were prepared by dissolving the peptide in CDCl$_3$ (0.03% TMS). Samples were prepared with total volumes of approximately 600 μL for 5 mm NMR tubes. Samples were referenced to tetramethylsilane. The NMR samples were stable in solution for weeks showing no apparent precipitation of peptide or decrease in NMR signal strength over the entire period of study. In all cases sharp lines were observed in 1D spectra suggesting that the peptides were not aggregated in solution. NMR experiments were performed on Varian INOVA 600 MHz spectrometers at 4° C. using a Varian 3 mm $^1$H/$^{13}$C/$^{15}$N with 3 axis PFG. The reported temperatures are presumed to be accurate to 1 K.

gCOSY, TOCSY, ROESY Methods:

Standard Varian pulse sequences were used, and data were processed using Varian VNMR 6.1 software and analyzed with the Sparky program (see Goddard, D. T.; Kneller, D. G. SPARKY 3, University of California, San Francisco). Spectral windows of 8000 Hz were used. Shifted sine bell window functions were generally applied before Fourier transformation. For all samples gCOSY spectra were obtained in absolute mode with gradient echo coherence selection; TOCSY[2] and ROESY[2,4] spectra were acquired in the sensitive mode with hypercomplex phase cycling (States-Haberkorn method). Experiments were performed by collecting 2048 points in f2 and 300-600 points in f1. TOCSY experiments employed a standard MLEV-17 spin lock sequence with a spin lock field of 7-8 KHz and mixing time of 80 ms. ROESY experiments used spin-locking fields of ~3 kHz's and mixing times of 250 ms. The $^1$H chemical shift assignment of the peptides was achieved by the sequential assignment procedures (see Wuthrich, K.; *NMR of Proteins and Nucleic Acids*; Wiley-Interscience: New York, 1986).

Example 2. Five and Six-Membered Ring Diastereomers

Other diastereomers may be prepared using the enantiomer of the chiral pyrrolidine catalyst used in Example 1. Using chiral co-catalyst (S)-A, the reactions illustrated in Scheme 2-1 were conducted.

Scheme 2-1.

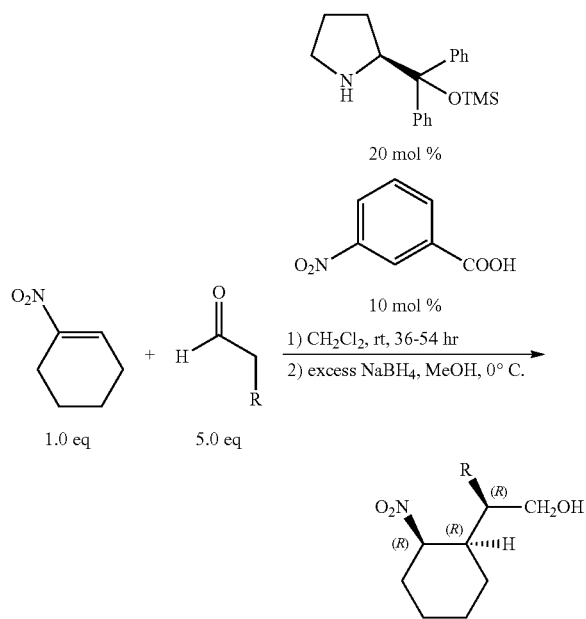

where R is —CH$_2$—CO$_2$Me, —Bn, or —CH$_2$—CH$_2$—CO$_2$-tBu.

Additional diastereomers can be prepared by epimerization of the nitro, as show above in Scheme 4 of the specification. The following compounds were prepared, according to the general methods outlined in Example 1, using chiral co-catalyst (S)-A.

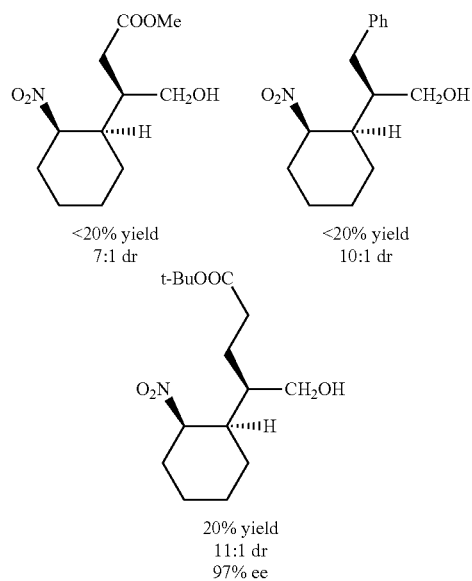

Reaction conditions and yields were not optimized. Aldol products competed with the Michael adducts, thereby reducing the yields obtained in these reactions with (S)-A. Additionally, five-membered ring system were found to be suitable substrates for the Michael addition reaction, as illustrated below in Scheme 2-2.

Scheme 2-2.

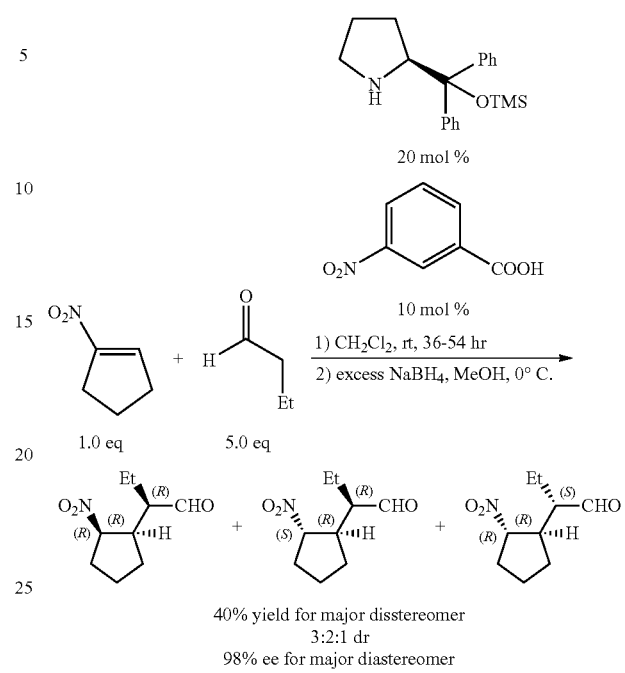

40% yield for major disstereomer
3:2:1 dr
98% ee for major diastereomer

A high enantiomeric excess was obtained for the major diastereomer for this unoptimized reaction. Additional diastereomers can be prepared by epimerization of the nitro, as show above in Scheme 4 of the specification.

Example 3. Ring Substitution and Heterocyclic Adducts

Additional Michael adducts can be prepared by using substituted nitrocyclohexenes, as illustrated in Scheme 3-1.

Scheme 3-1.

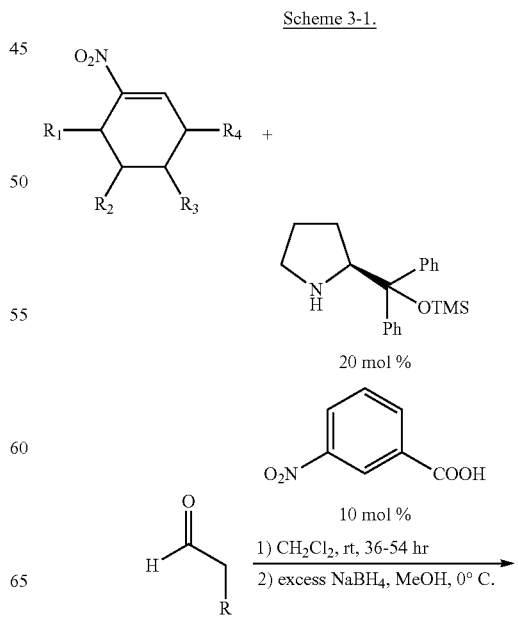

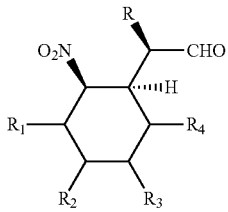

wherein $R_1$, $R_2$, $R_3$, $R_4$ can be, for example, hydrogen, alkyl, cycloalkyl, aryl, heteroaryl, or heterocycle, or protected amino.

The nitrocyclohexene starting materials can be monosubstituted, di-, tri-, or tetra-substituted with various groups, as described herein.

Other examples of the Michael reaction are illustrated below in Scheme 3-2, where an optionally protected 5-nitro-1,2,3,6-tetrahydropyridine or 4-nitro-1,2,3,6-tetrahydropyridine is allowed to react with the aldehyde. Additional diastereomers can be prepared by epimerization of the nitro, as show above in Scheme 4 of the specification.

Scheme 3-2.

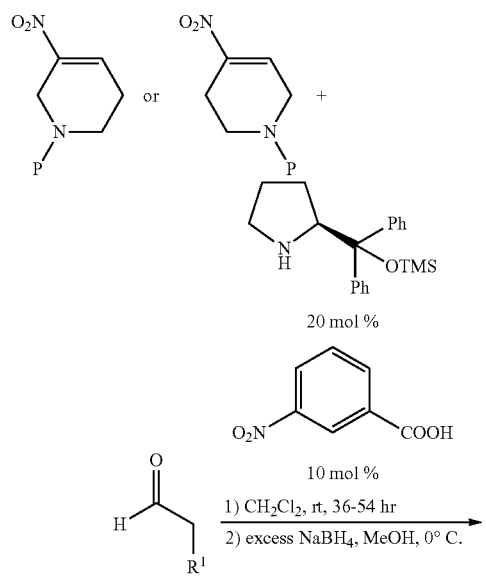

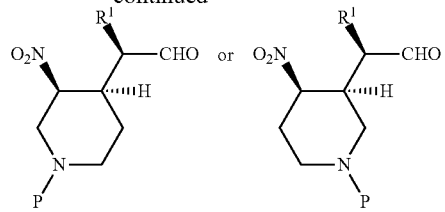

where P is H or a nitrogen protecting group, and $R^1$ is as described above for Formula I.

Example 4. New Methods for Preparing γ-Amino Acids and Peptides

A new methodology has been developed for the preparation of γ-amino acids. Novel peptides containing γ-amino acids can be prepared with these new amino acids using standard amide bond formation reactions and N and C terminus protection procedures when appropriate. A Michael reaction between nitromethane and cyclohexene-1-carbaldehyde provided nitro alcohols 20 and 21 (Scheme 4-1). These products formed an inseparable mixture of isomers (dr=7:1) in a 90% yield.

Scheme 4-1.

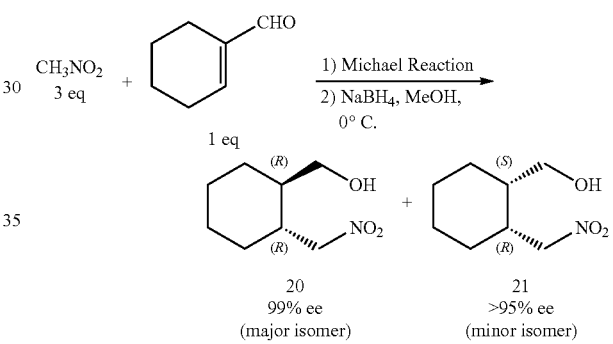

Jones oxidation of nitro alcohols 20 and 21 provided the (R,R) product as a white solid and the (R,S) product as an oil, thereby allowing for separation and isolation of the compounds (Scheme 4-2). Reduction and Boc protection afforded protected γ-amino acids for preparing novel peptides.

Scheme 4-2.

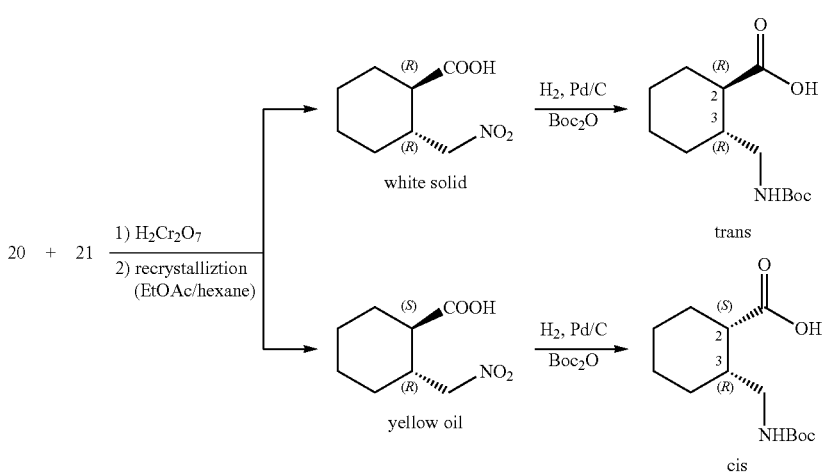

This methodology therefore allows for access to new cis and trans cyclically constrained γ-amino acids. These amino acids can be readily incorporated into polypeptides that include other γ-amino acids, or alternatively, α-amino acids, β-amino acids, and/or combinations thereof. Examples of α/γ-Peptides prepared are illustrated below in Scheme 4-3.

123, 11077). A highly stereoselective and high yielding Michael addition of nitromethane to cyclic enals A and B via iminium-mediated pyrrolidine catalysis is described herein (Scheme 5-A). This methodology can be extended to substituted and functionalized nitroalkanes, as discussed below.

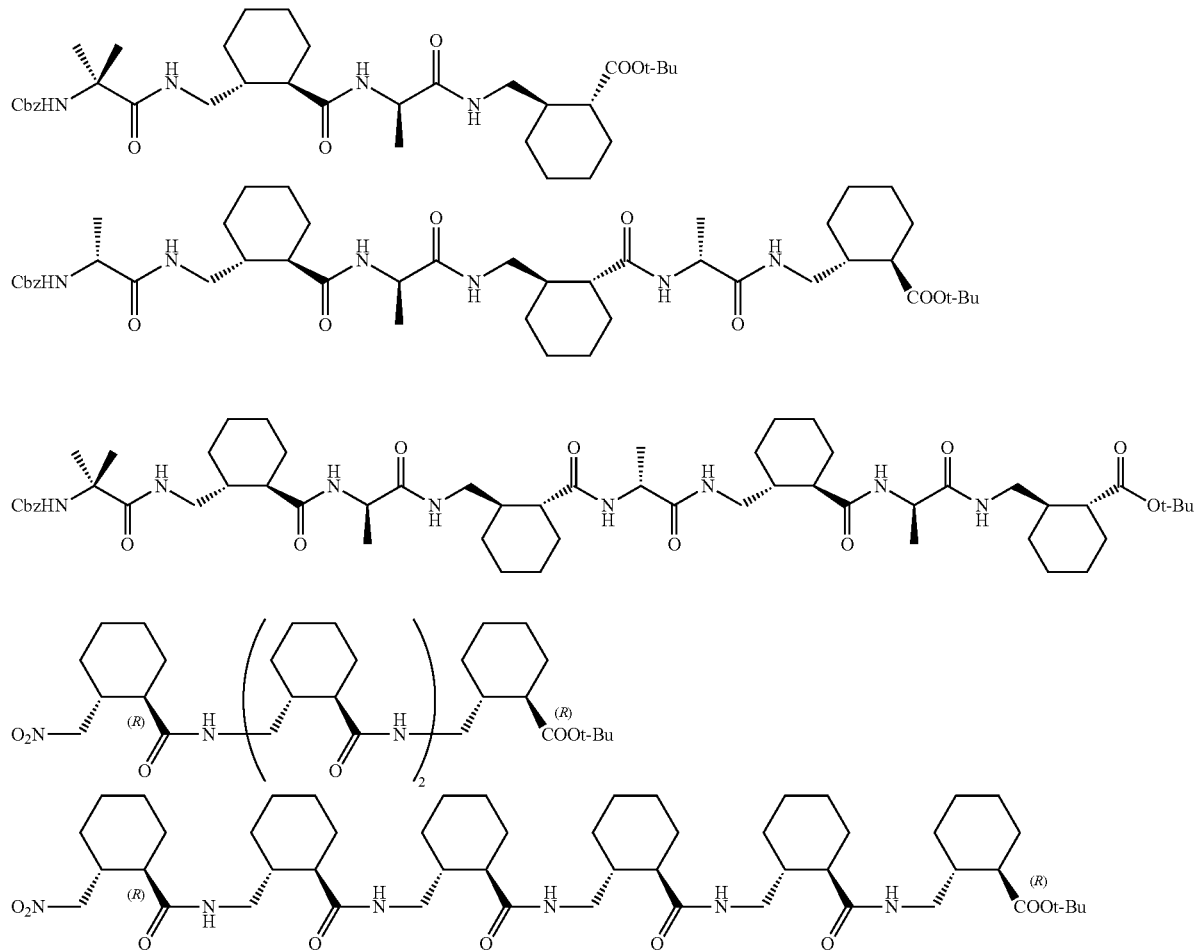

Scheme 4-3. α/γ-Peptides (1:1) and γ-Peptides.

By taking advantage of various protecting groups, or by starting with a γ-nitro acid, the polypeptides can be built up from either the C-terminus or the N-terminus (or its nitro equivalent).

Example 5. γ-Peptides Containing 5 or 6-Membered Rings

Recent synthetic efforts by the laboratory of the applicants of this disclosure have focused on the preparation of ring-constrained γ-amino acids and their incorporation into unnatural peptide oligomers (Guo et al., *J. Am. Chem. Soc.* 2009, 131, 16018; Guo et al., *J. Am. Chem. Soc.* 2010, 132, 7868; Woll et al., *J. Am. Chem. Soc.* 2001,

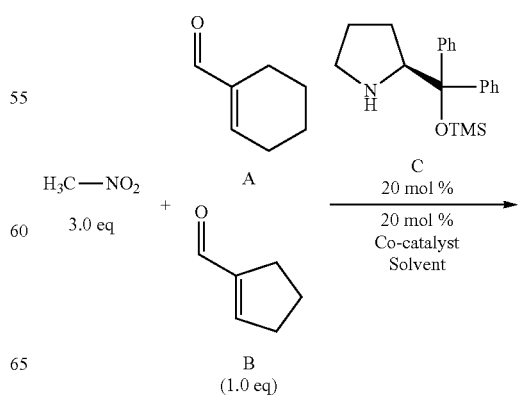

Scheme 5-A. Michael addition of nitromethane to cyclic enals.

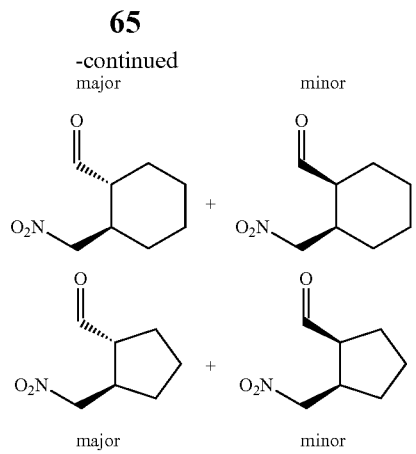

* absolute configurations were confirmed by crystal structure analysis of derivatives I. Synthetic Methodology.

The Hayashi/Jorgenson-type (S)-(−)-α,α-diphenylpyrrolidine methanol trimethylsilyl ether catalyst was used for these studies (Scheme 5-A, compound C) (Gotoh et al., *Org. Lett.* 2007, 9, 5307; Zu et al., *Adv. Synth. Catal.* 2007, 349, 2660; Wang et al., *Chem. Commun.* 2008, 1232; Garcia-Garcia et al., *Angew. Chem. Int. Ed* 2008, 47, 4719; Hayashi et al., *Angew. Chem. Int. Ed.* 2008, 47, 4722). Work began with examining solvent effects on both conversion of starting material and diastereoselectivity (Table 5-1). Polar protic solvents generally gave suitable results. Ethanol was selected for use in further screening reactions.

TABLE 5-1

Solvent Optimization for Michael Additions.

| Solvent | Enal | Conversion | d.r. |
|---|---|---|---|
| H₂O | A,B | N.R.* | n.d.* |
| MeOH | A,B | 65%, 90% | 5:1, 4.5:1 |
| EtOH | A,B | 91%, 91% | 7:1, ≥20:1 |
| iPrOH | A,B | 99%, 96% | 5:1, 20:1** |
| THF | A,B | N.R., 21.5% | n.d. |
| Et₂O | A,B | N.R., 93% | n.d., 3:1 |
| N,N-dimethylformamide | A,B | N.R. | n.d. |
| N-methylpyrrolidone | A,B | N.R. | n.d. |
| CH₂Cl₂ | A,B | 10%, 91% | 9:1, 20:1 |
| dichloroethane | A,B | N.R. | n.d. |

*N.R.: no reaction; n.d.: not determined
**While the d.r. for this reaction was good, unlike for EtOH, a minor diastereomer was obsvervable in the ¹H NMR spectrum.

A series of both basic and acidic co-catalysts were evaluated in both EtOH and CH₂Cl₂ solvents (Table 5-2). Benzoic acid was found to be the only single additive that provided suitable yields and stereoselectivity for both aldehydes.

TABLE 5-2

Co-Catalyst Optimization for Michael Additions (reaction times = 24 hours).

| Co-Catalyst | Enal | Solvent | Conversion | d.r. |
|---|---|---|---|---|
| benzoic acid | A,B | EtOH | 91%, 91% | 5:1, >20:1 |
| m-nitro-benzoic acid | A,B | EtOH | 10%, 83% | 5:1, 9:1 |
| acetic acid | A,B | EtOH | 90%, 94% | 7:1, >20:1 |
| H₂O | A,B | EtOH | 33%, 90% | n.d., >20:1 |
| N-methylmorpholine | A,B | CH₂Cl₂ | 6%, 95% | n.d., 1:1.5 |
| 2,4,6-Collidine | A,B | CH₂Cl₂ | 5%, 95% | n.d., 1:1.9 |
| triethylamine | A,B | CH₂Cl₂ | N.R., 27% | n.d., 1:2.5 |
| DBU | A,B | CH₂Cl₂ | 5%, N.R. | 1:1, n.d. |
| 3:1 2,4,6-Collidine:benzoic acid | A,B | EtOH | 90%*, 95%* | 5:1, >20:1 |

*reaction times were reduced to 12 hours and 2 hours for enals A and B, respectively The five-membered ring enal B is significantly more reactive than enal A, presumably due to increased ring strain. Base additives aid nitronate formation and a proton source is advantageous for iminium formation and hydrolysis (Hanessian et al., *Org. Lett.* 2006, 8, 4787). Thus, various combinations of benzoic acid and 2,4,6-collidine were screened as a 'buffered' co-catalyst system (Table 5-2, last entry). For both enals A and B, a 3:1 ratio of 2,4,6-collidine: benzoic acid (15 mol % and 5 mol % respectively) gave excellent yields and good diastereoselectivity. The increased reactivity allowed for a decrease in reaction time to 12 hours for enal A and to only two hours for enal B. Attempts to reduce catalyst loading or nitromethane equivalents resulted in decreased yield within optimized reaction times. Selected reactions were then evaluated for enantioselectivity using chiral HPLC (Table 5-3). For both enals, it was observed that the optimized conditions yielded the major diastereomer (or only diastereomer, in the case of enal B) in greater than 99% enantiomeric excess.

TABLE 5-3

Enantiomeric Excess for Selected Michael Reactions.

| Enal | Time (hrs) | Solvent | Co-Catalyst | Conversion | d.r. | e.e. |
|---|---|---|---|---|---|---|
| A | 24 | EtOH | benzoic acid | 91% | 5:1 | 99% |
| A | 24 | EtOH | Acetic acid | 90% | 5:1 | >99% |
| A | 12 | EtOH | 3:1 2,4,6-Collidine:benzoic acid | 90% | 5:1 | >99% |
| B | 24 | EtOH | benzoic acid | 91% | >20:1 | 95% |
| B | 24 | CH₂Cl₂ | benzoic acid | 91% | >20:1 | 78% |
| B | 24 | EtOH | acetic acid | 94% | >20:1 | 99% |
| B | 2 | EtOH | 3:1 2,4,6-Collidine:benzoic acid | 95% | >20:1 | >99% |

For 1-nitropropane (representative of monosubstituted nitroalkanes), the products were afforded in much lower diastereoselectivity. Four diastereomeric products were observed for the addition of 1-nitropropane to cyclic enal A (Scheme 5-1). However, the reaction for the addition of nitromethane is quite useful for preparation of at least two γ-amino acids of interest.

Scheme 5-1.

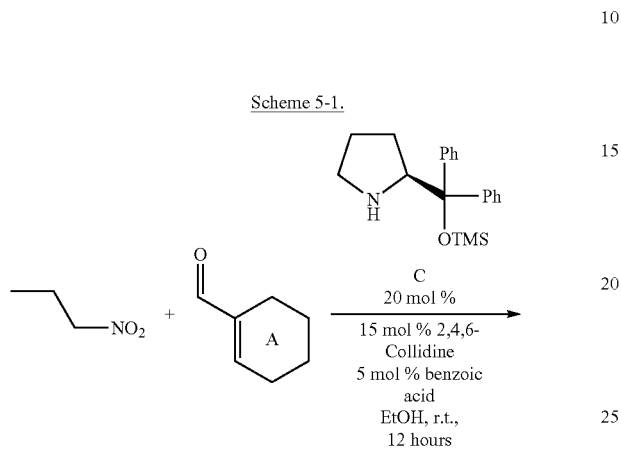

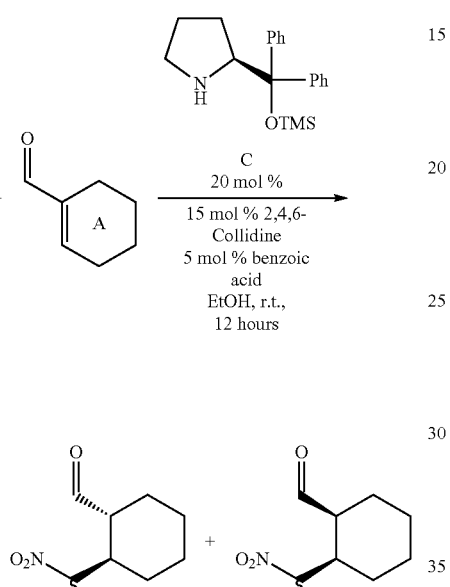

II. Preparation of N-Protected Monomers for Use in Solution-Phase Peptide Synthesis.

With a stereochemically pure γ-amino acid precursor in hand, a route was developed to obtain nitrogen-protected amino acid monomers that would be useful for solution-phase synthesis of γ- and α/γ-peptides. The route began with in situ sodium borohydride reduction of the γ-nitro aldehyde obtained from the Michael addition to the corresponding δ-nitro alcohol (Scheme 5-2).

Scheme 5-2. Synthesis of 2-(Aminomethyl)-1-Cyclopentane Carboxylic Acid (AMCP) Building Blocks.

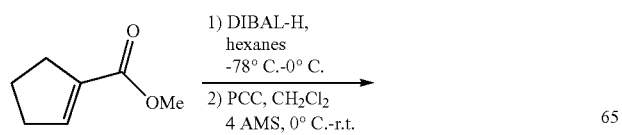

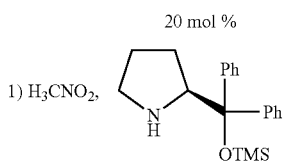

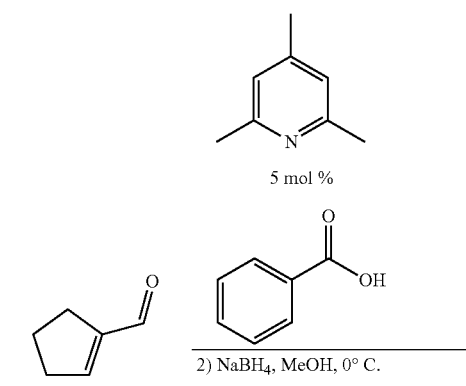

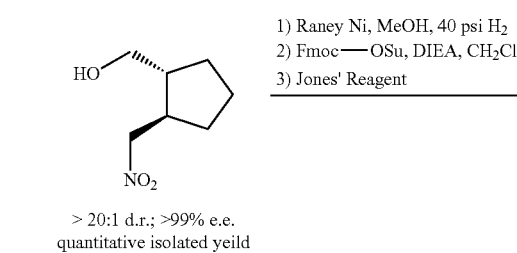

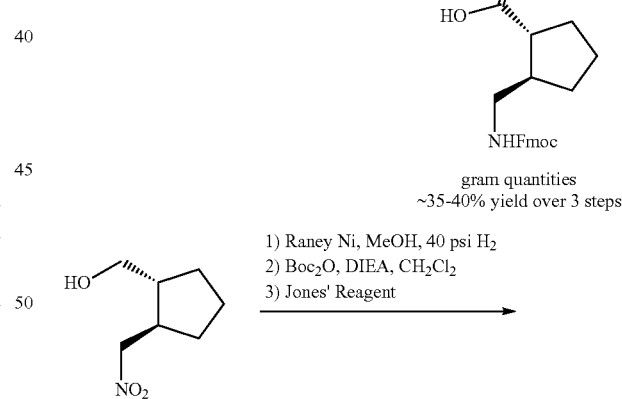

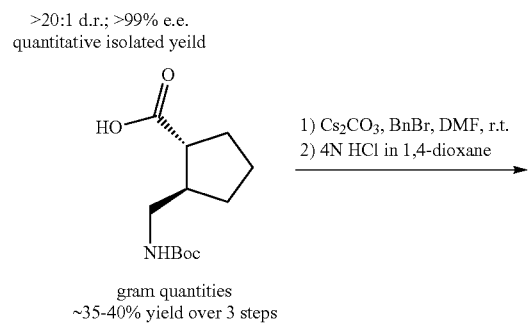

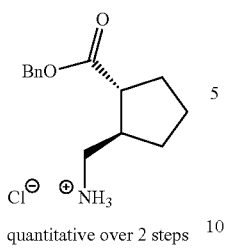

quantitative over 2 steps

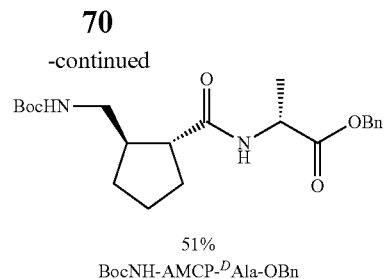

51%
BocNH-AMCP-$^D$Ala-OBn (a) Coupling of Boc-AMCP to $^L$Ala-OBn tosylate;
(b) Coupling of Boc-AMCP to $^D$Ala-OBn tosylate Previous routes by applicants carried the δ-nitro alcohol forward to a Jones' oxidation. That route proved unfruitful here due to difficulty of isolation of the γ-nitro acid product. Instead, the δ-nitro alcohol was reduced via Raney Ni and 40 psi H$_2$ to the corresponding amino alcohol. The crude material was carried directly into either a Fmoc- or Boc- protection reaction. These products were then carried forward through a Jones' oxidations to yield either Fmoc- or Boc-protected 2-(aminomethyl)-1-cyclopentane carboxylic acid (referred to herein as AMCP).

III. Dipeptides for Absolute Configuration Determination and α/γ-Peptide Studies.

A number of α/γ-dipeptides were prepared using Fmoc-AMCP and standard coupling reagents. However, all proved recalcitrant to crystallization from a wide range of solvent mixtures via slow evaporation. Boc-AMCP was therefore obtained and dipeptides using either D or L forms of Alanine benzyl ester tosylate were prepared (Scheme 5-3).

Scheme 5-3.

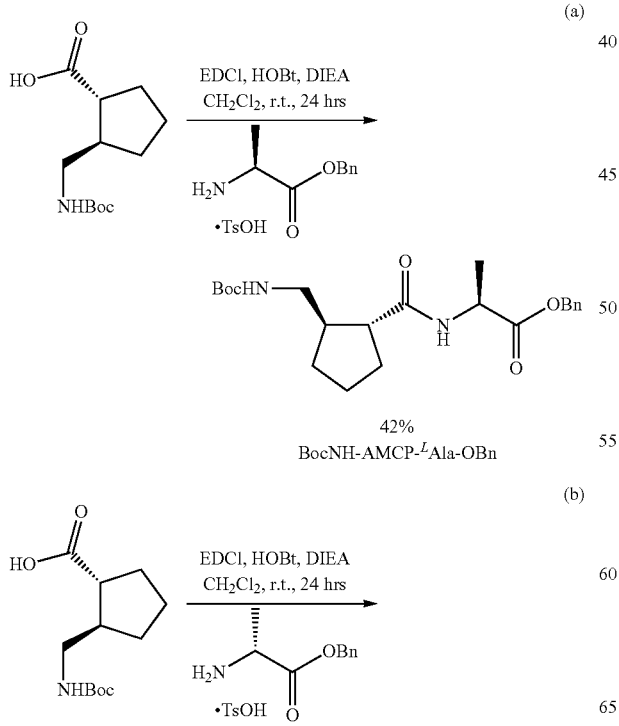

The couplings proceeded in moderate yields to provide useful amounts of both dipeptides. The dipeptides were isolated and several crystallization trials were set up using slow evaporation from mixtures of chloroform, ethyl acetate, methanol, heptane, and pentane. A mixture of ethyl acetate and heptane yielded large needles for the Boc-NH-AMCP-$^D$Ala-OBn dipeptide. These diffracted into the space group P1 and the X-ray crystal structure was solved. The absolute configuration of the AMCP residue was shown to be (R,R) for the ring stereocenters, resulting from the Michael addition using the (S) catalyst. The relative configuration of the stereocenters is trans.

The $C_\alpha$-$C_\beta$ (ζ) and $C_\beta$-$C_\gamma$ (θ) torsion angles obtained from this crystal structure were compared to theoretical calculations from the work of Hofmann et al. (Baldauf et al., *J. Org. Chem.* 2006, 71, 1200) (Table 5-4). The angles yielded from this structure compare favorably to those from Hofmann's calculations corresponding to the 10/12, 15/17, and 18/20 helices for α/γ-peptides. Furthermore, the sign of the angles (+, −) indicates that the (R,R)-AMCP residue can be used in combination with D-α-amino acid residues in the design of oligomers that can adopt helical conformations. Observation of the 15/17 or 18/20 helices in a crystal structure would represent the first such experimental evidence for either of these conformations. Based on the torsion angles observed for this residue, it is indeterminate whether β/γ-peptide oligomers incorporating it will adopt helical conformations.

TABLE 5-4

Torsion Angle Comparison of AMCP Residues with Hoffman Calculations.

| Reside/Helix | θ (°) | ζ (°) |
|---|---|---|
| (R,R)-AMCP residue | 54.7 | −112.9 |
| Hofmann 10/12 | 75.2 | −75.6 |
|  | 76.5 | −76.1 |
|  | 76.6 | −76.1 |
|  | 73.2 | −78.0 |
| Hofmann 18/20 | 64.9 | −168.0 |
|  | 60.9 | −78.6 |
|  | 76.7 | −81.5 |
|  | 73.2 | −84.8 |
| Hofmann 15/17 | 58.6 | −147.9 |
|  | 60.6 | −149.2 |
|  | 63.7 | −158.2 |
|  | 59.9 | +169.2 |

The synthesis of α/γ-peptide oligomers is detailed in Scheme 5-4 below. Boc-AMCP was coupled to D-Ala benzyl ester tosylate. This afforded a dipeptide with differentially protected N and C termini. Two aliquots of the dipeptide were carried forward. One was deprotected at the N-terminus with 4 N HCl in dioxane and the other was deprotected at the C-terminus using Pd/C and $H_2$. The segments were joined together using standard peptide coupling procedures.

hexamers and octamers) can be obtained through further iterations of differentially deprotected peptide N and C termini and subsequent amide coupling.

$^1$H NMR analysis of the tetramer shows evidence of hydrogen bonding. A single amide proton resonance is shifted far downfield at 8.2 ppm, attributable to a hydrogen bond (Scheme 5-5; curved arrow indicates non-sequential

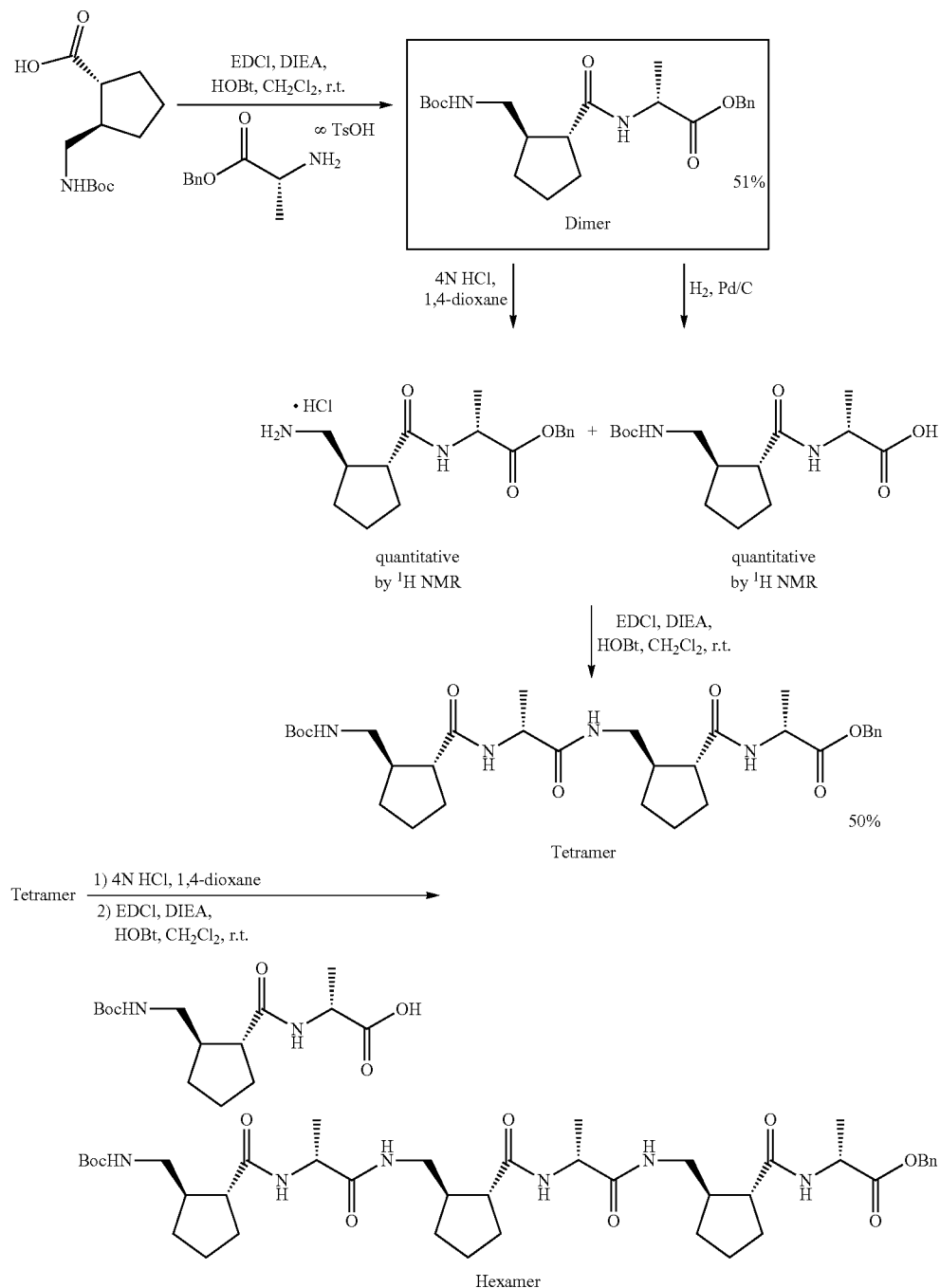

Scheme 5-4. Synthesis of 1:1 α/γ-peptide oligomers.

The synthesis provided the tetramer in modest yields. Increasing the reactant concentration in the coupling reaction should provide increased yields. Longer oligomers (e.g., NOE). 2D $^1$H NMR experiments (gCOSY, TOCSY, and ROESY) allowed for assignment of all proton resonances for the tetramer. The ROESY experiment showed an unambiguous NOE between the N—H of $^D$Ala(4) (involved in a hydrogen bond based on assignment) and the H$_\alpha$ of $^D$Ala(2). This indicates that a local conformation exists, presumably due to the torsion constraints of AMCP(3), such that $^D$Ala(2) and $^D$Ala(4) are brought close to one another in space. While the tetramer is not adopting a global helical conformation (likely due to its short length), the AMCP residue does appear to promote local structure within a peptide sequence. Preparation of longer oligomers with an alternating 1:1 α/γ residue pattern can be prepared to confirm this analysis.

Scheme 5-5. A 1:1 α/γ-peptide tetramer (NOEs shown by arrows).

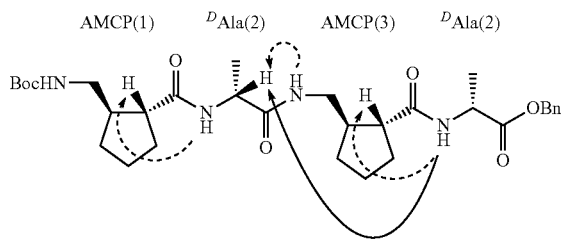

Peptides containing 1:2 and 2:1 ratios of α:γ residues as well as γ-peptide oligomers composed exclusively of AMCP residues can be prepared. The homo-oligomer preparation can include converting the Boc-AMCP to its benzyl ester HCl salt by standard methodology to provide the sequences illustrated in Scheme 5-6, where (a) is a 2:1 α/γ-peptide hexamer; (b) is a 1:2 α/γ-peptide hexamer; (c) is a γ-peptide homotetramer; and (d) is a γ-peptide homooctamer.

Using these techniques, a variety of new peptides can be prepared, where the peptide includes a novel γ-amino acid described herein, and any other amino acid. The peptides can be prepared with the amino acid residues in any order, such as αγ, ααγ, αγγ, ααγγ, and the like, and the peptides can be linked to other peptides, such as those that include β-amino acids.

In summary, peptides that incorporate a 5-membered ring-containing γ-amino acid have been prepared and analyzed. These peptides possess a unique set of torsion constraints in the design of novel foldamer secondary structures. An asymmetric organocatalytic reaction has also been developed that allows for the preparation of a γ-amino acid residue (e.g., AMCP) that contains a 5-membered ring constraint. The AMCP residue can be incorporated into α/γ-peptide sequences. Results indicate that such peptides allow for access to previously uncharacterized foldamer helices.

Example 6. Helix Formation in Preorganized β/γ-Peptide Foldamers: Hydrogen-Bond Analogy to the α-Helix without α-Amino Acid Residues Identification of new types of foldamers with strong and discrete secondary structural propensities is a subject of much ongoing research. These studies enhance our understanding of the relationship between local conformational preferences and molecular shape. In addition, new folding patterns can be valuable for specific applications. Foldamers that contain more than one type of subunit, i.e., oligomers that have heterogeneous backbones, have been a subject of extensive recent interest. Most examples involve a combination of α-amino acid residues with other types of subunits, Scheme 5-6.

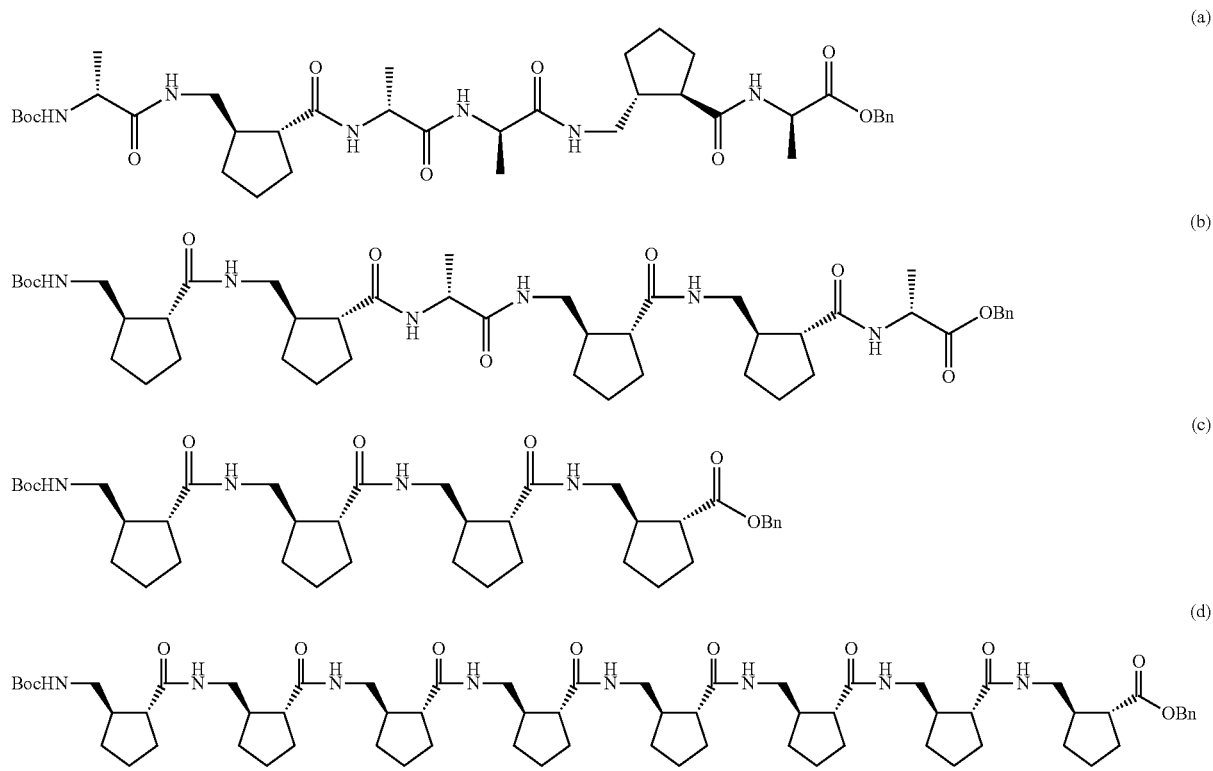

including those derived from β- or γ-amino acids or other building blocks. Heterogeneous backbones that do not include α-amino acid residues have received relatively limited attention, perhaps because α-amino acids are far more available than are other building blocks. Backbones with alternating β- and γ-amino acid residues (β/γ-peptides) are of particular interest because a β/γ-dipeptide has the same number of atoms between the N- and C-termini as an α-tripeptide. An extended β/γ-peptide can in principle form a helix containing 13-membered ring backbone H-bonds (C=O(i)-H—N(i+3)) that are analogous to the 13-membered ring backbone H-bonds characteristic of the α-helix conformations about the $C_\alpha$-$C_\beta$ ($\zeta$) and $C_\beta$-$C_\gamma$ ($\theta$) bonds in the γ-residues and a $C_\alpha$-$C_\beta$ torsion angle of ~90° in the β-residues. Based on these predictions and available data for the conformational propensities of constrained β- and γ-residues in other contexts, it was concluded that combining (R,R,R) γ-residue 1 (Scheme 6-1 with (R,R)-trans-2-aminocyclopentanecarboxylic acid (ACPC, 2) should favor formation of the left-handed β/γ-peptide 13-helix (the right-handed helix should be favored by residues with S configurations). This hypothesis was tested by preparation and analysis of tetramer 3, pentamer 4, and hexamer 5 (Scheme 6-1).

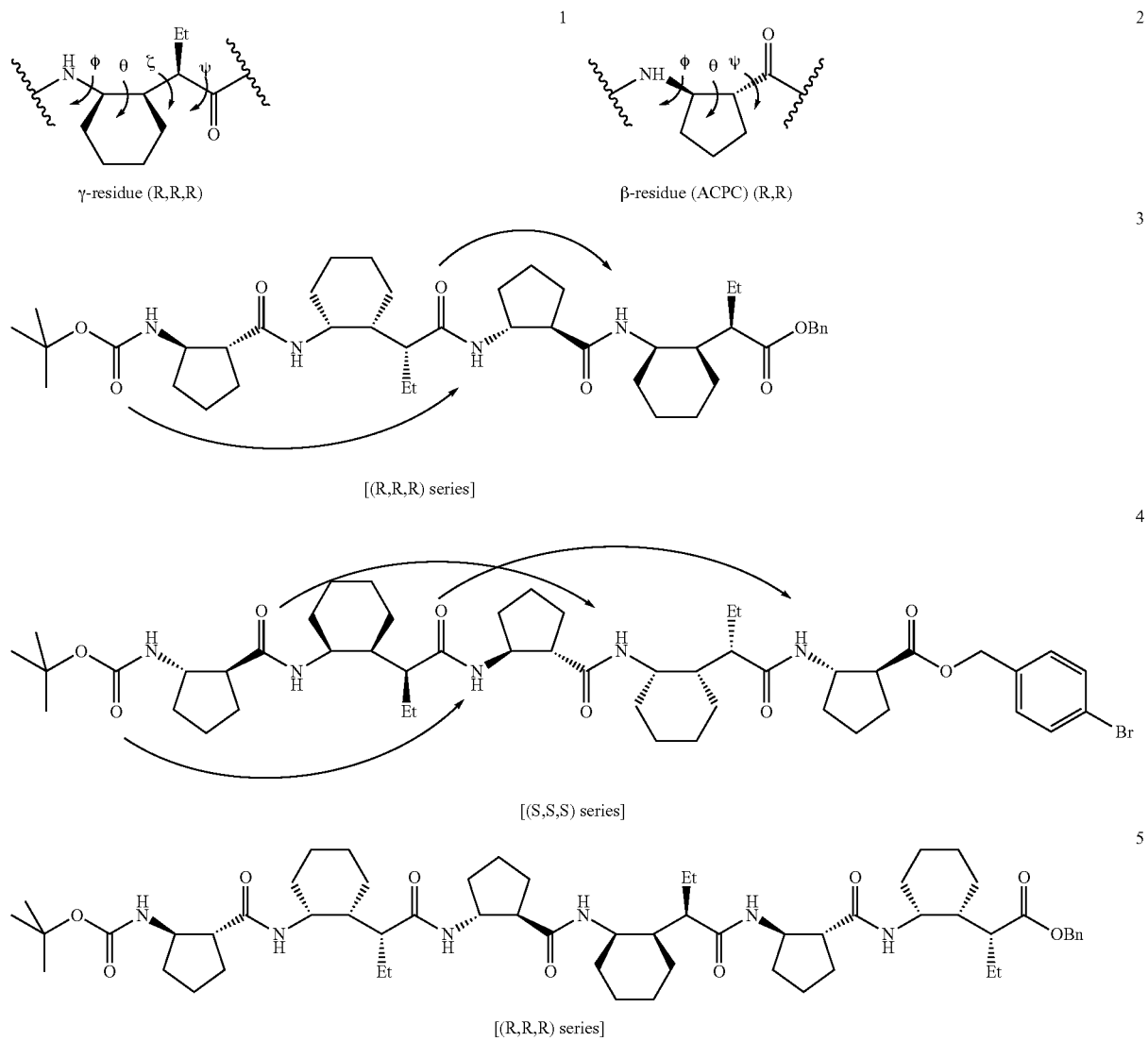

Scheme 6-1. Structures of β/γ-peptides, 3, 4, and 5 (arrows indicate H-bonds in the crystal structres of 3 and 4).

(C=O(i)-H—N(i+4)). However, Sharma, Kunwar et al. (*J. Am. Chem. Soc.* 2006, 128, 14657) have recently reported that flexible β/γ-peptides adopt a different type of helical conformation in solution. Here we show that β/γ-peptides containing appropriately preorganized subunits do indeed adopt the 13-helix in solution and the solid state.

The β/γ-peptide 13-helix is predicted by Hofmann et al. (*J. Org. Chem.* 2006, 71, 1200) to have g+, g+ or g−, g− local The crystal structure of (3/γ-peptide 3 contains two molecules in the asymmetric unit; the two conformations are very similar. Each independent molecule forms one 13-atom H-bonded ring, involving the NH group of the second ACPC residue and the carbonyl of the N-terminal Boc group. The other possible 13-atom ring H-bond does not form in either case [N—O distance ~4.9 Å]; instead, each molecule contains an 8-atom ring H-bond involving the carbonyl of the first γ-residue and the NH group of the second γ-residue. Despite this deviation from the 13-helical H-bonding pattern, the backbone torsion angles for the β- and γ-residues in 3 generally fall in ranges predicted by Hofmann et al. for the β/γ-peptide 13-helix (see *J. Am. Chem. Soc.* Vol. 132, No. 23, 2010, 7868-7869 and the supporting information therein).

Pentamer 4, containing β- and γ-residues with S configurations, adopts the right-handed 13-helix in the crystalline state. All three of the possible C=O(i)-H—N(i+3) H-bonds are formed. Table 6-1 compares backbone torsion angles for the β- and γ-residues in pentamer 4 with analogous values from the computational work of Hofmann et al. and from the NMR analysis of flexible β/γ-peptides in organic solvent by Sharma, Kunwar et al.

tons, six strong NOEs were observed between protons from residues that are not adjacent in the sequence: $C_\beta H(1)$-NH (3), $C_\beta H(1)$-$C_\alpha H(3)$, $C_\gamma H(2)$-NH(4), $C_\beta H(3)$-NH(5), $C_\beta H(3)$-$C_\alpha H(5)$, and $C_\gamma H(4)$-NH(6) (Scheme 6-2).

Scheme 6-2. Characteristic NOE patters observed for 1:1 β/γ-peptide hexamer 5 in pydine-d₅.

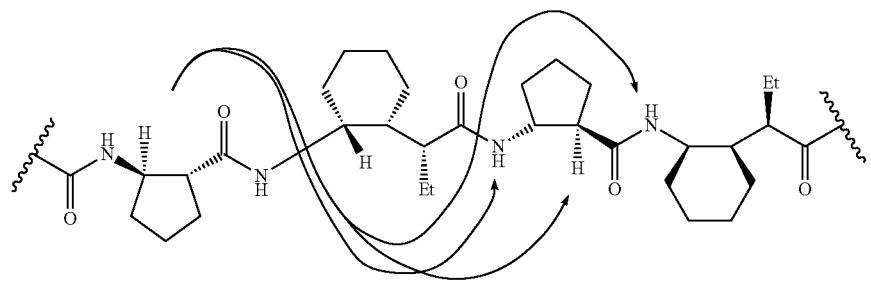

These NOEs are consistent with intramolecular proton-proton distances in the crystal structure of pentamer 4: $C_\beta H(1)$-NH(3)=3.5 Å, $C_\beta H(1)$-$C_\alpha H(3)$=2.7 Å, $C_\gamma H(2)$-NH(4)=2.8 Å, $C_\beta H(3)$-NH(5)=2.3 Å, and $C_\beta H(3)$-$C_\alpha H(5)$=2.2 Å. Thus, the three NOE patterns observed for 5, $C_\beta H(i)$-NH(i+2) and $C_\beta H(i)$-$C_\alpha H(i+2)$ for β-residues and $C_\gamma H(i)$-NH(i+2) for γ-residues, appear to be general indicators of β/γ-peptide 13-helical secondary structure.

The β/γ-peptide helix documented herein is interesting because of its relationship to the α-helix formed by pure α-residue backbones. Both helices contain 13-atom ring H-bonds. Detailed comparison of the two helices reveals further similarities: both have a rise-per-turn of 5.4 Å, and the radii are similar (2.5 vs 2.3 Å). These parameters indicate that the β/γ-peptide 13-helix is a suitable scaffold for functional mimicry of natural α-helices.

These results show that appropriately preorganized residues promote the formation of the 13-helical conformation in short β/γ-peptides. This secondary structure was estimated in computational studies, and hints of 13-helical propensity can be found in the local conformations observed in crystal structures for isolated β-γ segments, but the only previous analysis of β/γ-peptide oligomer folding indicated the formation of a different helical conformation, containing both 11- and 13-membered ring H-bonds (Sharma et al., *J. Am. Chem. Soc.* 2006, 128, 14657). Conformationally constrained β-amino acid residues have been shown to induce novel secondary structures, and the studies described herein highlight the prospect that constrained γ-amino acid residues will be similarly useful in controlling molecular shape.

TABLE 6-1

Backbone Torsion Angles (deg)[a] of Helical β/γ-Peptides.

| Peptides | residues | φ | θ | ζ | ψ |
|---|---|---|---|---|---|
| β/γ pentamer 4 | β1 | −107.7 | 93.3 | | −128.3 |
| | γ2 | −134.7 | 60.1 | 59.8 | −121.0 |
| | β3 | −133.6 | 113.5 | | −85.7 |
| | γ4 | −147.3 | 57.9 | 46.5 | −129.8 |
| | β5 | −167.9 | 141.4 | | −155.0 |
| computational study[b,5b] | β | 89.1 | −94.1 | | 121.9 |
| | γ | 124.9 | −60.4 | −62.2 | 132.0 |
| flexible β/γ tetramer (NMR)[5e] | β | 120 | 60 | | 0 |
| | γ | 120 | −60 | 60 | −120 |

[a]Nomenclature for the backbone torsion angles in b/g-peptides is described in Scheme 6-1.
[b]Average backbone torsion angles.
[5b]Karle et al., *J. Am. Chem. Soc.* 1997, 119, 9087.
[5e]Sharma et al., *J. Am. Chem. Soc.* 2006, 128, 14657.

The preorganized γ-residues in 4 display g⁺, g⁺ local conformations about the $C_\alpha$-$C_\beta$ (ζ) and $C_\beta$-$C_\gamma$ (θ) bonds and ψ and φ near −120°, with a somewhat wider distribution for the latter torsion angle. These values are consistent with the predictions for the 13-helical conformation from Hofmann et al. In contrast, the helical conformations deduced via NMR for flexible β/γ-peptides feature opposite signs for the ζ and θ torsion angles (g⁻, g⁺) and opposite signs for the ψ and φ torsion angles. The helical conformation deduced for these flexible β/γ-peptides has a distinctive H-bonding pattern with two types of interaction: C=$O_\gamma$(i)-H—$N_\beta$(i−1)) and C=$O_\beta$(i)-H—$N_\gamma$(i+3).

Hexamer 5 did not produce high-quality crystals, but 2D ¹H NMR analysis in pyridine-d₅ solution indicated that the 13-helix is significantly populated under these conditions. Among the unambiguous NOEs involving backbone pro-

Example 7. The γ-Peptide 14-Helix and Structural Parameters

Only one helical secondary structure has been documented among γ-peptides, the 14-helix, which is defined by C=O(i)-H—N(i+3) H-bonds. Although the existence of this conformation has been clearly established via 2D NMR studies, the paucity of crystallographic data has hindered identification of the structural parameters that are characteristic of this helix. Four new crystal structures of 14-helical γ-peptides are reported herein. These structures enabled the elucidation of robust structural parameters.

The complexity of structure and function among biopolymers has inspired chemists to extrapolate to non-natural analogues that are intended to emulate the natural prototypes. Extrapolation from the α-amino acid backbone of proteins to β-amino acid backbones, for example, has yielded a large family of β-peptide "foldamers" that display helix, sheet and reverse turn secondary structures comparable to (but different in detail from) the regular secondary structures found in proteins. β-Peptides manifest a wider range of secondary structure variation than do α-peptides; only two H-bonded helices are observed in proteins, the α-helix and the $3_{10}$-helix, but at least five H-bonded helices have been documented so far among β-peptides. Elucidation of folding rules for β-peptides has enabled function-directed design.

The structural and functional diversity displayed by β-peptides has encouraged exploration of higher amino acids as foldamer subunits; however, such efforts are hampered by the difficulty of obtaining stereochemically pure building blocks. Although γ-peptides that form discrete helix, sheet or reverse turn secondary structures have been reported, the pace of γ-peptide exploration lags behind that of β-peptides. The only experimentally documented γ-peptide helix, defined by 14-atom ring i,i+3 C=O—H—N H-bonds, was identified through pioneering efforts of Hanessian et al. and Seebach et al., but just one atomic-resolution structure containing this helix has been previously reported. A conformationally constrained γ-amino acid (Guo et al., J. Am. Chem. Soc. 2009, 131, 16018) was used to generate a set of crystal structures that allow derivation of characteristic parameters for the γ-peptide 14-helix, which was not possible from previously available data.

Solution-phase methods were used to prepare a homologous γ-peptide series, 3-7 (Scheme 7-1), which contain a Boc-protected residue derived from commercially available gabapentin (1) at the N-termini, and cyclically constrained residues derived from γ-amino acid 2 at all other positions. Stepwise synthesis of α-peptides typically proceeds from C-terminus to N-terminus, because carboxyl activation of α-amino acid derivatives in which the backbone nitrogen is part of an amide group (e.g., at the C-terminus of a peptide) often leads to epimerization via transient azlactone formation, while epimerization is suppressed when the amino group is part of a urethane (e.g., Boc). A complementary situation was found with γ-peptides constructed from 2: the N-Boc derivative of 2 is highly prone to γ-lactam formation under standard coupling conditions, and this side reaction is suppressed when the backbone nitrogen is part of an amide. Therefore, γ-peptides 3-7 were constructed via stepwise extension starting from the N-terminus. A gabapentin residue was placed at the N-terminus because N-Boc-gabapentin is not prone to γ-lactam formation during coupling reactions, and previous structural analysis of short gabapentin-containing peptides raised interesting questions, as discussed below.

Scheme 7-1. γ-Peptides 3-7 (arrows indicate H-bonds in the crystal structures of 3-7).

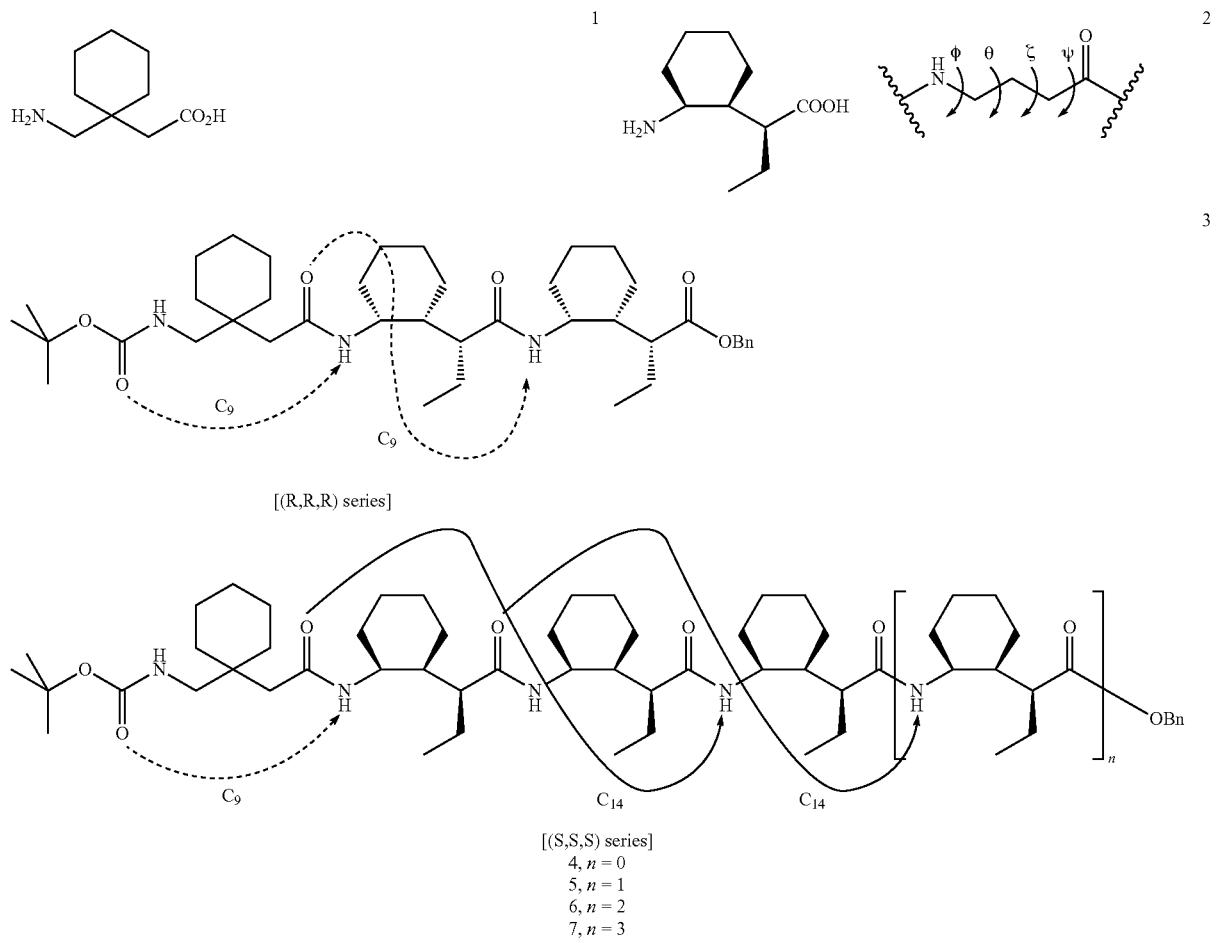

Figure 4:
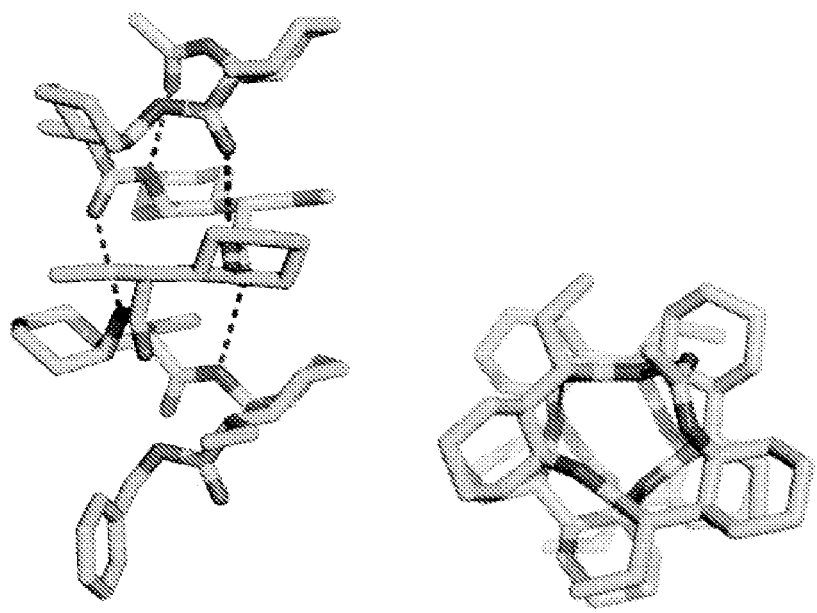
FIG. 4 illustrates the crystal structure of 7, highlighting the 14-helical segment (N-terminal gabapentin residue not shown), with a stereoview (left), and a view along the helical axis.

In the crystal structures of 4-7, the segments derived from 2 display the 14-helical conformation. See FIG. 4 for the crystal structure of 7. All possible 14-atom ring H-bonds are formed within each of these segments. This data set permits derivation of robust averages for the backbone torsion angles of a γ-amino acid residue involved in a canonical 14-helix (Table 7-1).

TABLE 7-1

Average Torsion Angles[a] from γ-Peptides 4-7.

| residues | φ | θ | ζ | ψ |
|---|---|---|---|---|
| gabapentin[b] | 98.6 | −67.2 | −76.7 | 82.5 |
| γ (14-helical)[c] | −154.5 | 60.2 | 59.5 | −126.8 |
| γ (C-terminal)[d] | −129.4 | 56.9 | 60.2 | −136.7 |

[a]Nomenclature for the backbone torsion angles in γ-residues is as illustrated in Scheme 7-1.
[b]Average torsion angles based on four independent gabapentin residues in 4-7.
[c]Average backbone torsion angles based on 14 independent γ residues of 4-7; the C-terminal residues were not included; see experimental details below).
[d]Average torsion angles based on four independent C-terminal residues in 4-7.

These average values correspond well to relevant torsion angles in the only previous crystal structure of a helical γ-peptide, a tetramer (Seebach et al., Chem. Commun. 2001, 207). The averages recited herein do not include the C-terminal residue from 4-7. The C-terminus itself is an ester in each case, and the lack of an H-bond donor at this position prevents incorporation of the C-terminal γ-residue into the helical H-bond pattern. Similarly, the C-terminus of the previously described Seebach tetramer is an ester, and in this case the C-terminal γ-residue displays torsion angles that deviate dramatically from those required for the 14-helix (for example, the (O=)CC$_\alpha$—C$_\beta$C$_\gamma$ (ζ) and C$_\alpha$C$_\beta$-C$_\gamma$N (θ) torsion angles are anti rather than gauche in this structure). Among 4-7, only minor backbone torsion angle variations are observed between the C-terminal residue and other residues derived from 2, a trend that presumably arises because the cyclic constraint of 2 confers strong conformational preorganization, in contrast to the modest conformational preference provided by an acyclic stereochemical control strategy.

Standard methods for deriving helical parameters such as the number of residues per turn (n), rise per turn (pitch; p), rise per residue (d) and radius (r) require atomic-resolution structures containing segments of four contiguous helical residues (Kahn, P. C. Comput. Chem. 1989, 13, 185). Hexa-γ-peptide 6 and hepta-γ-peptide 7 provide the first opportunities for such analysis among γ-peptides, with one four-residue segment in 6 and two in 7. The helical parameters deduced from these three segments are very similar to one another, as shown in Table 7-2.

TABLE 7-2

14-Helical Parameters from Structures of 6 and 7.

| peptides | res/turn n | rise/turn p (Å) | rise/res d (Å) | radius r (Å) |
|---|---|---|---|---|
| hexamer 6 | 2.5 | 5.4 | 2.1 | 2.9 |
| heptamer 7 | 2.6 | 5.5 | 2.1 | 2.9 |
|  | 2.5 | 5.5 | 2.2 | 2.9 |
| average | 2.5 | 5.5 | 2.1 | 2.9 |

A nine-atom ring H-bond (C=O(i)-H—N(i+2)) is observed across the gabapentin residue at the N-terminus of 3-7 in each crystal structure. Trimer 3 has a second $C_9$ H-bond, across the central residue, which indicates that this H-bond pattern is energetically reasonable for γ-amino acid residues derived from 2. However, no $C_9$ H-bond is observed in the crystal structures of the larger γ-peptides. Tetramer 4 is the smallest member of the series in which a 14-atom H-bond can form across a γ-peptide segment built entirely from 2. The dominance of this H-bonding pattern among 4-7 is evidence that the residue derived from 2 has an intrinsic conformational preference that supports formation of the $C_{14}$ H-bond. In contrast, data indicate that the gabapentin residue has a strong preference for the $C_9$ H-bond. Even when the gabapentin residue could participate in a 14-helix, as in 4-7, this residue consistently forms the shorter-range H-bond.

The conclusions derived regarding gabapentin conformational preferences are consistent with those suggested collectively by the many crystal structures of short gabapentin-containing peptides reported by Balaram et al. (Vasudev, et al., Acc. Chem. Res. 2009, 42, 1628). Although gabapentin residues are occasionally caught in other local conformations by crystallization, this subunit usually forms a $C_9$ H-bond. In early studies directed toward peptidic foldamer research, it was noted that adoption of compact and specific conformations by unnatural backbones would require subunits that are averse to formation of H-bonds between amide groups that are nearest neighbors in a covalent sense (Dado, G. P.; Gellman, S. H. J. Am. Chem. Soc. 1994, 116, 1054). The protein backbone displays this property because formation of so-called $C_5$ or $C_7$ H-bonds (C=O(i)-N—H(i) or C=O(i)-N—H(i+2)) is intrinsically unfavorable. Model studies suggested a comparable situation with β-amino acid residues, and these subunits have proven to be very successful as foldamer building blocks (Home, W. S.; Gellman, S. H. Acc. Chem. Res. 2008, 41, 1399). In contrast, model studies suggested that γ-amino acid residues might have too strong a tendency for nearest-neighbor H-bonding to be valuable as foldamer building blocks. Subsequent work has demonstrated that appropriate substitution patterns can render γ-amino acids competent as foldamer building blocks, the most recent examples being the results presented here.

Atomic-resolution conformational data for a series of 14-helical γ-peptides have enabled us to derive characteristic parameters for this secondary structure. This level of analysis was not previously possible among γ-peptides. These structural insights provide a basis for development of γ-peptides intended to display specific functions.

I. Materials and Instrumentation.

Proton nuclear magnetic resonance ($^1$H NMR) spectra were recorded on Bruker AC-300 (300 MHz) spectrometers. Chemical shifts were recorded in parts per million (ppm, δ) relative to tetramethylsilane (δ 0.00). $^1$H NMR splitting patterns are designated as singlet (s), doublet (d), triplet (t), or quartet (q). All first-order splitting patterns were assigned on the basis of the appearance of the multiplet. Splitting patterns that could not be easily interpreted are designated as multiplet (m) or broad (br). Carbon nuclear magnetic resonance ($^{13}$C NMR) spectra were recorded on a Bruker AC-300 (75 MHz) spectrometer. Mass spectra (MS) were obtained using an electrospray ionization (ESI) mass spectrometer. Optical rotations were measured using a 1 mL cell with a 1 dm path length on a Perkin-Elmer 241 digital polarimeter and are reported as follows: $[\alpha]^{rt}_D$(c in g per 100 mL solvent). Flasks were oven-dried overnight and cooled under a stream of nitrogen. Reagents were purchased from Aldrich Chemical Company. Flash chromatography was performed using silica gel 60 Å (32-63 mesh) from Sorbent Technologies. Reactions were monitored by thin layer chromatography (TLC) using 0.25 mm E. Merck pre-coated silica gel 60 (particle size 0.040-0.063 mm). Visualization was performed using a UV lamp or potassium permanganate stain.

II. Peptide Synthesis and Purification.

γ-Peptides 3-7 were synthesized by standard solution-phase methods. The tert-butyloxycarbonyl group (Boc) was used for N-terminal protection, and the C-terminal was protected as a benzy ester (OBn). Deprotection at the N-terminus was performed using 4 N HCl in dioxane, and hydrogenation was used to remove the C-terminal benzyl protecting groups.

N, N-Diisopropylethylamine (DIEA), 4-dimethylaminopyridine (DMAP) and coupling reagents (N,N-dimethylamino) propyl-3-ethylcarbodiimide hydrochloride (EDCI) and 1-hydroxybenzotriazole (HOBt) were purchased from Sigma-Aldrich and Chem-Impex.

Attempts for Synthesis of Homooligomers of γ-Amino Acid 2.

Experiments began by exploring homo-dimer synthesis with the thought that the longer homologues could be prepared in a convergent way by coupling dimers and tetramers. The preparation of cyclic γ-amino acid derivatives (e.g., $NO_2$-γ-OH (S2), Boc-γ-OH (S1)) was described in a paper from the laboratories of applicants (Guo et al., *J. Am. Chem. Soc.* 2009, 131, 16018).

The carboxylic acid group of Boc-γ-OH (S1) was protected as the benzyl ester by reaction with $Cs_2CO_3$ and benzyl bromide in DMF (90% yield, Scheme 7-2). The Boc group was removed from Boc-γ-OBn with 4 N HCl in dioxane to give HCl.$NH_2$-γ-OBn (S3). The coupling reaction between Si and S3 in the presence of 1-ethyl-3-(3-dimethylaminopropyl) carbodiimide hydrochloride (EDCI.HCl, a water-extractable coupling reagent) and DIEA proceeded in very low yield to provide homo-dimer S5 (<10%). Boc-protected acid Si was found to be highly prone to formation of γ-lactam S4 formation upon activation of the carboxylic acid. Next, the coupling reaction of HCl.$NH_2$-γ-OBn (S3) and $NO_2$-γ-OH (S2), with the nitro group serving as a protected amino group), was examined under identical conditions. This reaction led to a modest improvement (40% yield of desired amide 56). The poor yield may reflect the steric hindrance near the carboxylic acid group of $NO_2$-γ-OH (52) and the amino group of S3. These reaction conditions produce a significant yield of anhydride S7 (38%). Epimerization of dimer S6 at the nitro group occurred when the reaction was conducted in DMF; other observations suggest that this type of cis-to-trans epimerization is a general trend in polar solvents. This observation is significant because polar solvents are required for synthesis of longer oligomers. The observations summarized in Scheme 7-2 indicate that a target such as hexamer S9 cannot be efficiently prepared via coupling reactions involving homodimers and standard reagents and conditions.

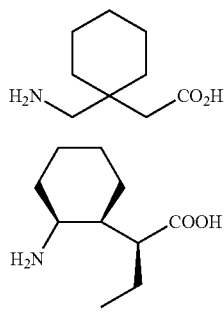

1

2

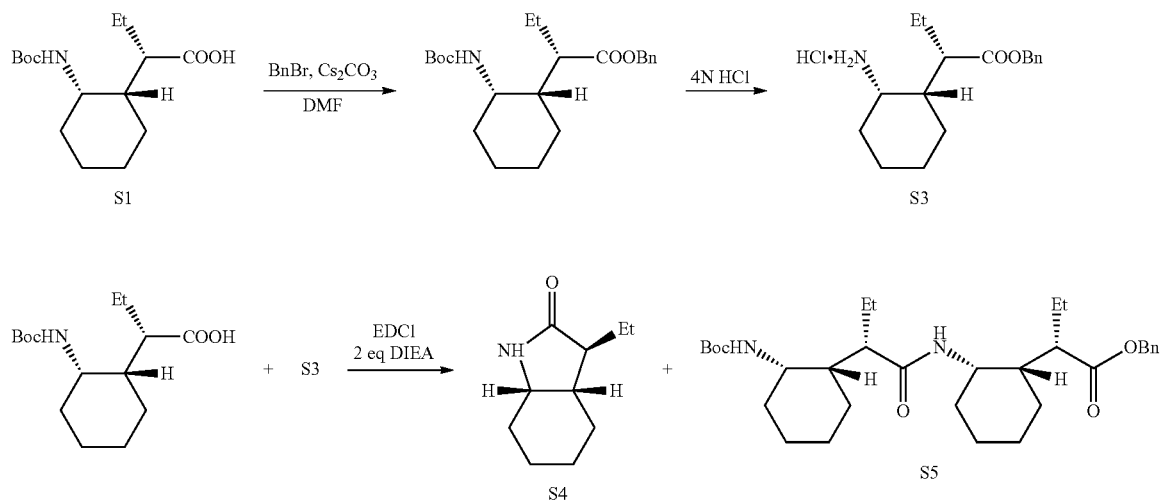

Scheme 7-2. Synthesis of a homo-dimer of γ-amino acid residue 2.

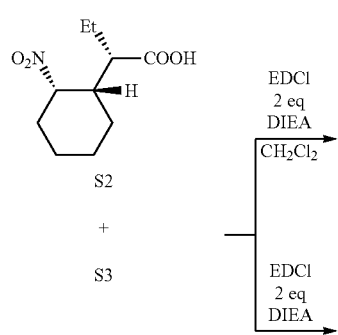
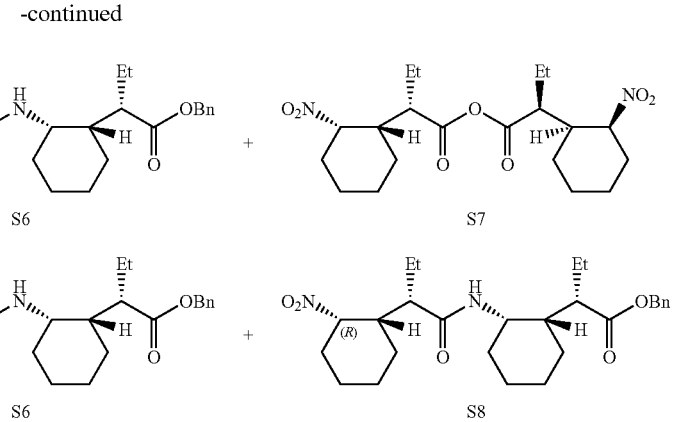

Attention was then turned to a new design, γ-peptide 7 (Scheme 7-3), which contains a gabapentin residue at the N-terminus. If constrained residue 2 proved to be sufficiently preorganized, it would be possible to retain γ-peptide folding when a more flexible gabapentin residue is placed at the N-terminus. Since gabapentin derivatives such as S10 lack a substituent at $C_\alpha$, carbonyl-activated derivatives should be intrinsically more reactive than those generated from S1 because of less steric hindrance near the carboxyl group.

this case) can undergo epimerization at the α-position. To solve this problem, HOBt was introduced along with EDCI.HCl. As an alternative, PyBOP, an HOBt-based phosphonium type coupling reagent, can be used instead of EDCI.HCl/HOBt. HOBt can react with O-acylurea S13 to form active OBt ester S14, which is less susceptible to epimerization. However, the preparation of the longer oligomers by using EDCI.HCl/HOBt was problematic due to the low reactivity of OBt active esters. Interestingly, OBt esters such

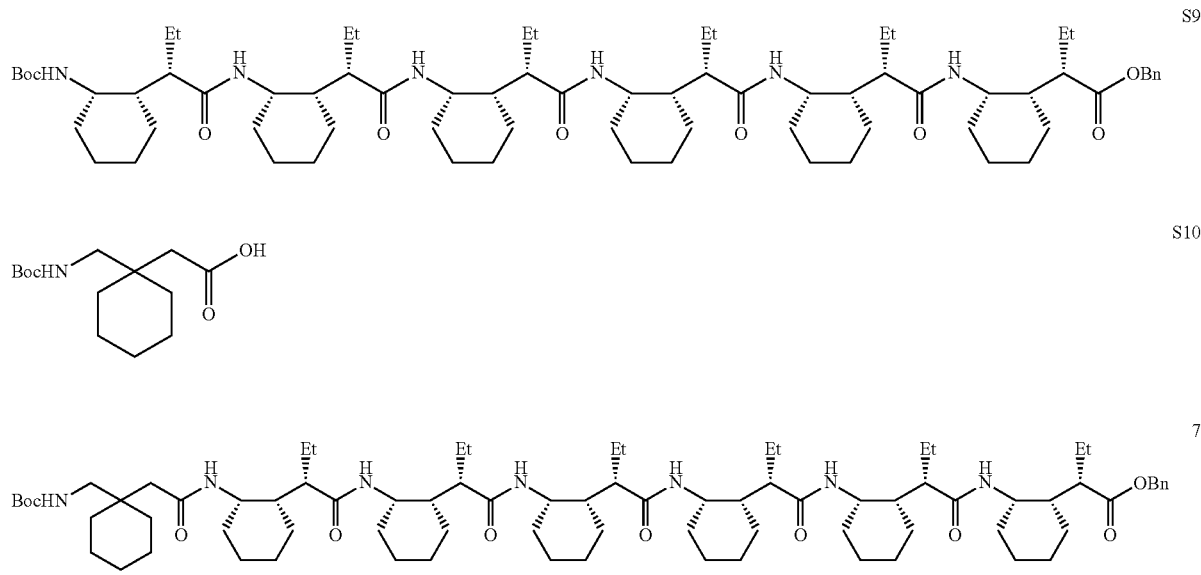

Boc-gabapentin-OH (S10) was coupled to the hydrochloride salt of S3 (HCl.NH$_2$-γ-OBn) using EDCI and DIEA to provide γ-dipeptide S11 in 90% yield. This dimer was then benzyl-deprotected (H$_2$, Pd/C), and the resulting acid, S12, was coupled with another equivalent of the hydrochloride salt of S3 (HCl.NH$_2$-γ-OBn). This coupling reaction was initially carried out with EDCI.HCl. The problem with carbodiimides is that the intermediate O-acylurea (S13 in as S14 are easily isolated (80%). They are stable in the presence of another equivalent of amine hydrochloride salt S3 under the EDCI/DIEA-mediated coupling conditions. Finally, the coupling reaction of S12 with S3 was performed in presence of EDCI.HCl and 4-dimethylaminopyridine (DMAP), which serves both as a nucleophilic catalyst and a base. γ-Tripeptide 3 was obtained in moderate yield (~60%).

Scheme 7-4. Synthesis of oligomers S11 and 3.

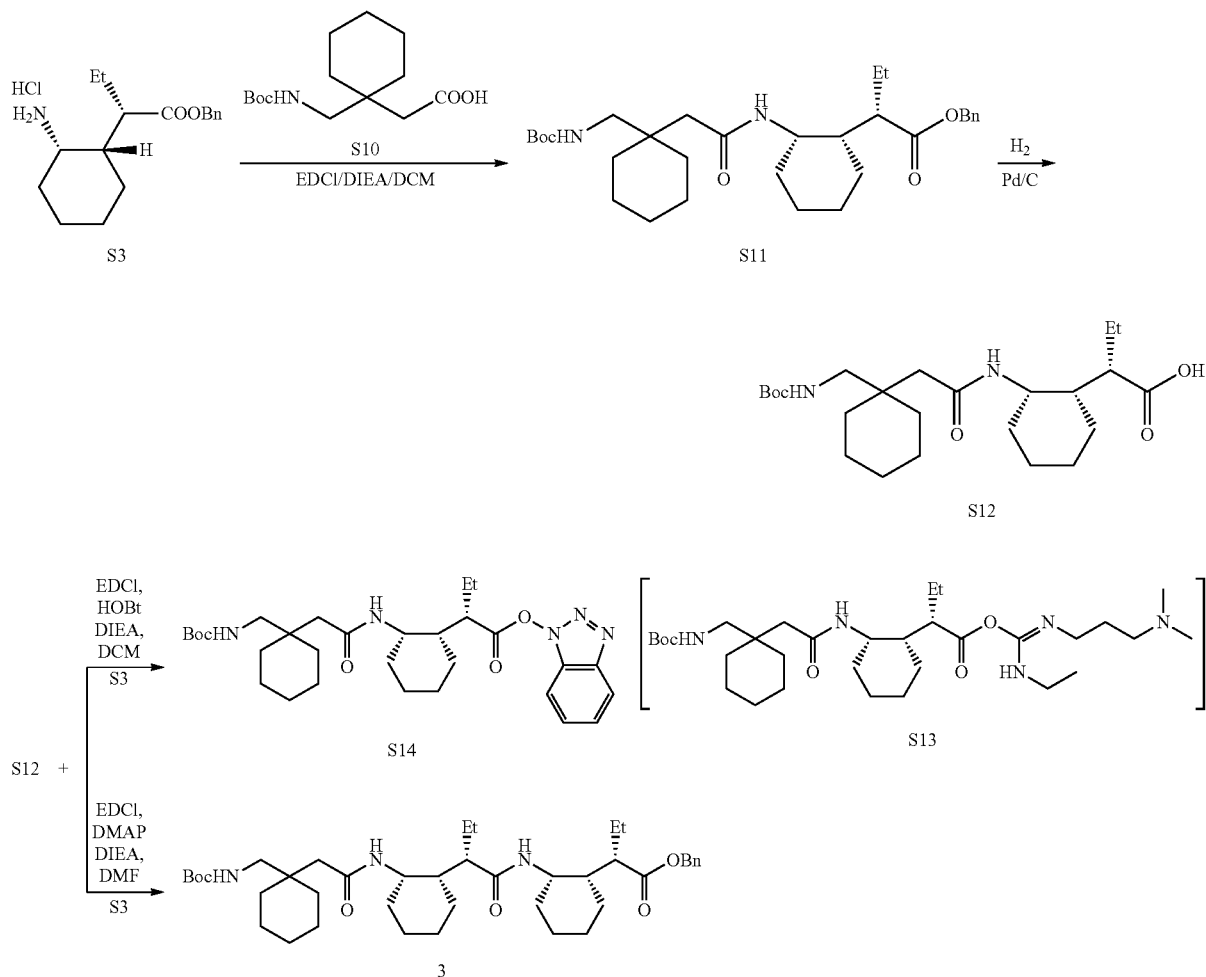

The production of trimer 3 through heptamer 7 was achieved through a series of coupling/deprotection reactions (Scheme 7-5). Residues were added in a stepwise fashion with the EDCI/DAMP mediated coupling followed by hydrogenolysis deprotection of the benzyl protected C-terminus. The coupling in each step was to the amine hydrochloride salt of S3; these reactions proceeded in moderate yield (~55%). Nevertheless, sufficient quantities of oligomers up to heptamer 7 could be obtained to allow physical characterization.

Scheme 7.5. Synthesis of oligomers 4-7.

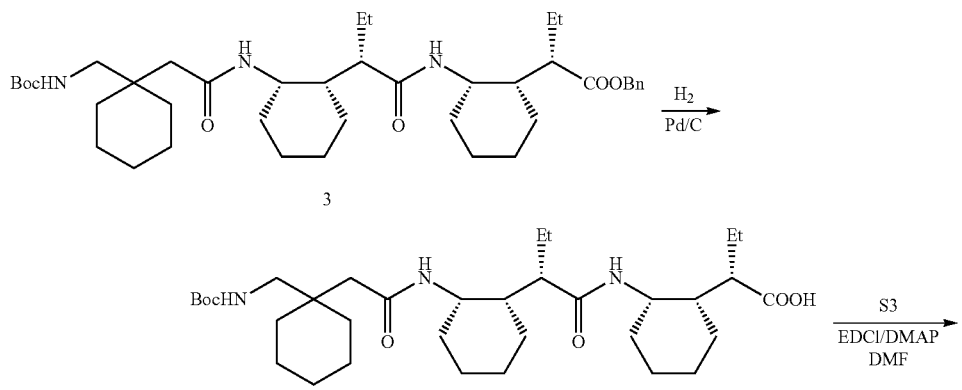

-continued

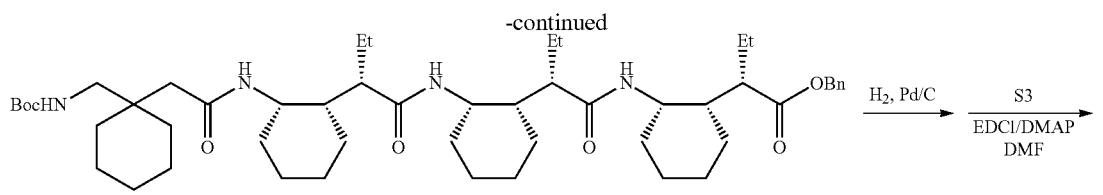

4

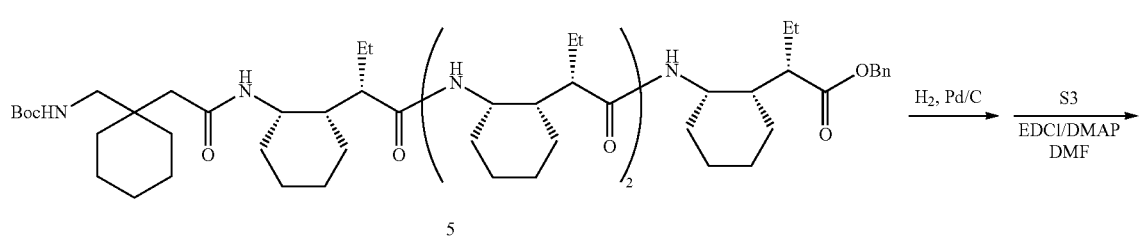

5

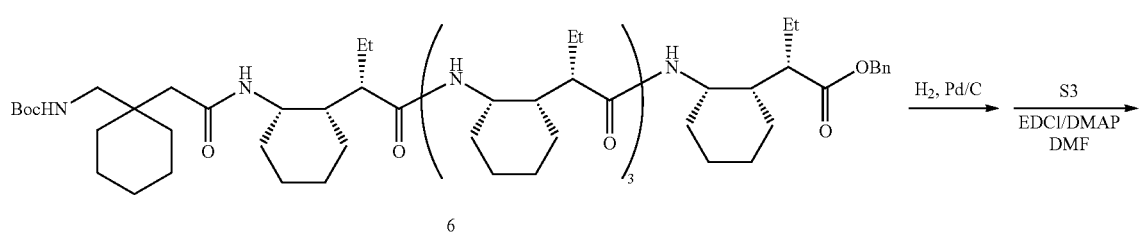

6

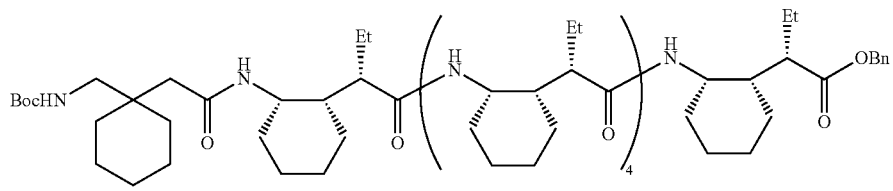

7

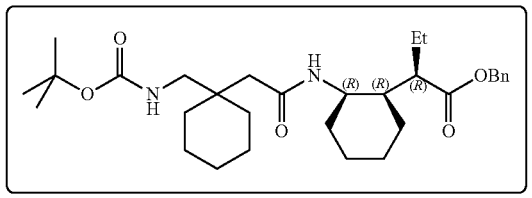

Dimer (Boc-Gabapentin-γ-OBn, R,R,R SERIES): Boc-Gabapentin-OH (518 mg, 1.91 mmol) was added directly to a solution of (R,R,R)—HCl.NH$_2$-γ-OBn (595 mg, 1.91 mmol), EDCI (480 mg, 2.50 mmol), HOBt (337 mg, 2.50 mmol), and N,N-diisopropylethylamine (523 μL, 3.00 mmol) in CH$_2$Cl$_2$ (15 mL). The resulting solution was stirred for 24-36 hrs at room temperature. The reaction mixture was diluted with EtOAc, washed with 1 M aqueous NaHSO$_4$, saturated aqueous NaHCO$_3$ and then brine. The organic layer was collected and dried over Na$_2$SO$_4$, filtered and concentrated to give a residue that was purified via column chromatography eluting with EtOAc and hexanes to yield the desired product (908 mg, 90% yield) as white foam. TLC $R_f$=0.69 (EtOAc/hexanes, v/v, 1:1). $^1$H NMR (300 MHz, CDCl$_3$) δ 7.44 (d, J=8.0 Hz, 1H), 7.38-7.28 (m, 5H), 5.22, 4.99 (AB, J$_{AB}$=12.4 Hz, 2H), 5.15 (X of ABX, 1H), 4.18 (m, 1H), 3.19, 3.03 (AB of ABX, JAB=14.5 Hz, JAX=6.4 Hz, JBX=7.5 Hz, 2H), 2.38 (td, J=10.2, 4.1 Hz, 1H), 2.08, 2.04 (AB, J$_{AB}$=13.1 Hz, 2H), 1.92-1.12 (m, 30H), 0.82 (t, J=7.4 Hz, 3H); $^{13}$C NMR: (75.4 MHz, CDCl$_3$) δ 175.72, 170.69, 157.44, 136.52, 128.62, 128.57, 128.15, 79.68, 66.37, 49.67, 47.68, 47.10, 42.84, 41.55, 37.35, 34.48, 34.36, 31.45, 28.57, 26.27, 26.03, 24.24, 23.30, 21.72, 20.84, 11.78; HRMS m/z (ESI): calcd. for: C$_{31}$H$_{49}$N$_2$O$_5$ [M+H]$^+$ 529.3636. found 529.3632.

General Procedure for Hydrogenolysis of C-Terminal Benzyl Ester Groups:

Boc-Gabapentin-γ-OBn was dissolved in methanol. and the flask was flushed with N$_2$. To the flask was added catalytic amount of 10% Pd/C, and the flask was attached to a Parr apparatus and shaken for 6-7 hours at a H$_2$ pressure of 10 psi. The reaction mixture was filtered through a pad of celite and concentrated to give Boc-Gabapentin-γ-OH as a white solid. The crude product was carried on without purification.

γ-Peptide 3 (R,R,R SERIES):

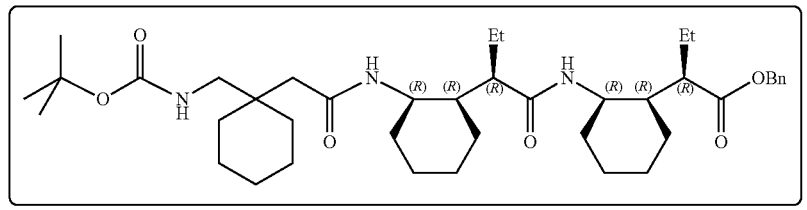

Boc-Gabapentin-γ-OH (662 mg, 1.51 mmol) was added directly to a solution of (R,R,R)—HCl.NH$_2$-γ-OBn (471 mg, 1.51 mmol), EDCI (347 mg, 1.81 mmol), DMAP (185 mg, 1.51 mmol), and N,N-diisopropylethylamine (526 μL, 3.02 mmol) in DMF (15 mL). The resulting solution was stirred for four days at room temperature. The reaction mixture was diluted with EtOAc, washed with 1 M aqueous NaHSO$_4$ and then brine. The organic layer was collected and dried over MgSO$_4$, filtered and concentrated to give a residue that was purified via column chromatography eluting with EtOAc and hexanes to yield the desired product (630 mg, 60% yield) as white foam. TLC R$_f$=0.56 (EtOAc/hexanes, v/v, 1:1). $^1$H NMR (300 MHz, CDCl$_3$) δ 7.72 (d, J=8.6 Hz, 1H), 7.44 (d, J=9.1 Hz, 1H), 7.40-7.24 (m, 5H), 5.26, 4.99 (AB, JAB=12.2 Hz, 2H), 5.17 (X of ABX, 1H), 4.29 (m, 2H), 3.18, 2.99 (AB of ABX, JAB=14.2 Hz, JAX=6.2 Hz, JBX=7.6 Hz, 2H), 2.58 (td, J=10.5, 3.9 Hz, 1H). 2.25, 2.16 (AB, JAB=12.8 Hz, 2H), 1.88-1.00 (m, 42), 0.79 (m, 6H); $^{13}$C NMR: (125.7 MHz, CDCl3) δ 176.18, 174.71, 171.91, 157.23, 136.73, 128.94, 128.52, 128.03, 79.72, 66.37, 50.20, 49.70, 48.06, 46.69, 42.49, 42.01, 37.70, 34.73, 34.60, 32.15, 30.74, 28.50, 26.13, 25.88, 23.88, 23.57, 23.26, 21.85, 21.64, 21.56, 20.56, 19.85, 12.57, 11.87; HRMS m/z (ESI): calcd. for C$_{41}$H$_{66}$N$_3$O$_6$ [M+H]$^+$ 696.4947. found 696.4938.

γ-Peptide 4 (S,S,S SERIES):

(115 μL, 0.66 mmol) in DMF (5 mL). The resulting solution was stirred for four days at room temperature. The reaction mixture was diluted with EtOAc, washed with 1 M aqueous NaHSO$_4$ and then brine. The organic layer was collected and dried over MgSO$_4$, filtered and concentrated to give a residue that was purified via column chromatography eluting with EtOAc and hexanes to yield the desired product (208 mg, 55% yield) as a white solid. TLC R$_f$=0.64 (EtOAc/hexanes, v/v, 1:1). $^1$H NMR (300 MHz, CDCl$_3$) δ 7.80 (d, J=9.4 Hz, 1H), 7.71 (d, J=8.6 Hz, 1H), 7.44 (m, 2H), 7.35-7.21 (m, 3H), 6.09 (d, J=8.4 Hz, 1H), 5.29, 5.01 (AB, JAB=12.6 Hz, 2H), 4.96 (X of ABX, 1H), 4.34 (m, 1H), 4.16 (m, 2H), 3.25, 3.00 (AB of ABX, JAB=14.5 Hz, JAX=6.7 Hz, JBX=7.4 Hz, 2H), 2.64 (td, J=10.3, 3.9 Hz, 1H), 2.17 (s, 2H), 2.06 (td, J=10.6, 4.4 Hz, 1H), 1.98-1.03 (m, 53H), 0.85 (m, 9H); $^{13}$C NMR: (125.7 MHz, CDCl3) delta 176.75, 175.05, 174.84, 170.93, 157.50, 137.09, 128.71, 128.43, 127.68, 80.05, 66.09, 50.57, 48.66, 48.45, 47.78, 47.73, 46.43, 41.98, 41.71, 41.49, 37.52, 34.66, 34.07, 32.24, 31.66, 30.21, 28.44, 26.36, 26.11, 26.03, 23.44, 23.39, 23.29, 23.07, 23.03, 22.93, 21.62, 21.52, 20.48, 20.25, 12.24, 11.95, 11.31; HRMS m/z (ESI):

4

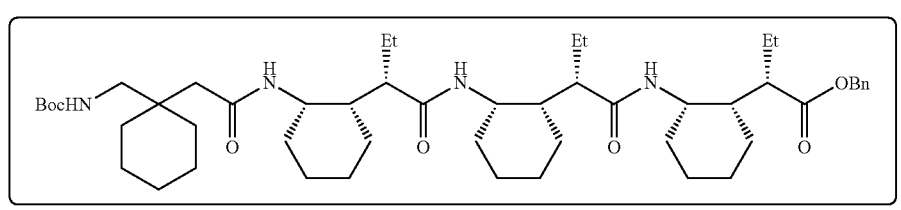

(S,S,S,S,S,S)-Boc-Gabapentin-γ-γ-OH (252 mg, 0.44 mmol) was added directly to a solution of (S,S,S)—HCl.NH$_2$-γ-OBn (141 mg, 0.45 mmol), EDCI (101 mg, 0.53 mmol), DMAP (54 mg, 0.44 mmol), and DIEA calcd. for: C$_{51}$H$_{82}$N$_4$O$_7$Na [M+Na]$^+$ 885.6076. found 885.6039.

γ-Peptide 5 (S,S,S SERIES):

5

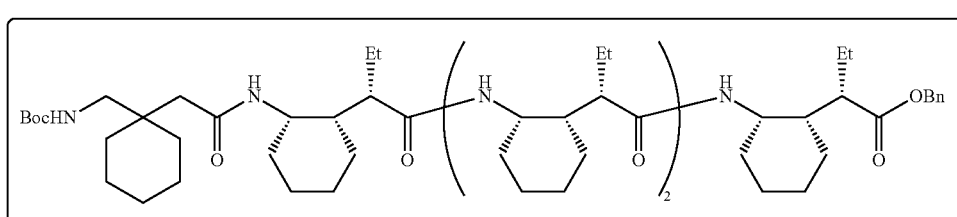

Boc-Gabapentin-γ-γ-γ-OH (58 mg, 0.075 mmol) was added directly to a solution of HCl.NH$_2$-γ-OBn (24 mg, 0.075 mmol), EDCI (17 mg, 0.090 mmol), DMAP (9 mg, 0.075 mmol), and DIEA (16 µL, 0.090 mmol) in DMF (2 mL). The resulting solution was stirred for four days at room temperature. The reaction mixture was diluted with EtOAc, washed with 1 M aqueous NaHSO$_4$ and then brine. The organic layer was dried over MgSO$_4$, filtered and concentrated to give a residue that was purified via column chromatography eluting with EtOAc and hexanes to yield the desired product (39 mg, 50% yield) as white foam. TLC R$_f$=0.66 (EtOAc/hexanes, v/v, 1:1). $^1$H NMR (300 MHz, CDCl$_3$) δ 7.88 (d, J=8.3 Hz, 1H). 7.79 (d, J=9.8 Hz, 1H), 7.48 (m, 2H), 7.35-7.20 (m, 3H), 6.99 (d, J=8.4 Hz, 1H), 5.78 (d, J=10.1 Hz. 1H), 5.33, 5.03 (AB, JAB=12.6 Hz, 2H), 4.91 (X of ABX, 1H), 4.44 (m, 1H), 4.17 (m. 2H), 4.10 (m, 1H), 3.40, 2.89 (AB of ABX, JAB=14.6 Hz, JAX=5.6 Hz, JBX=8.3 Hz, 2H), 2.69 (m, 1H), 2.22 (td, J=11.0, 4.3 Hz, 1H), 2.12 (s, 2H), 2.10-1.05 (m, 65H), 0.89 (m, 12H); $^{13}$C NMR: (125.7 MHz, CDCl3) delta 176.96, 175.63, 174.72, 174.31, 170.74, 157.72, 137.36, 128.56, 128.37, 127.46, 80.15, 65.94, 51.00, 48.80, 47.86, 47.45, 46.76, 46.09, 41.32, 41.22, 40.81, 40.24, 37.48, 34.74, 33.77, 32.67, 32.48, 31.32, 30.49, 28.45, 26.47, 26.17, 26.10, 25.78, 24.20, 23.97, 23.79, 23.47, 23.40, 22.90, 22.63, 21.58, 21.36, 20.74, 20.51, 20.39, 20.05, 11.82, 11.47, 11.18, 11.00; HRMS m/z (ESI): calcd. for: C$_{61}$H$_{99}$N$_5$O$_8$Na [M+Na]$^+$ 1052.7386. found 1052.7387.

γ-Peptide 6 (S,S,S SERIES):

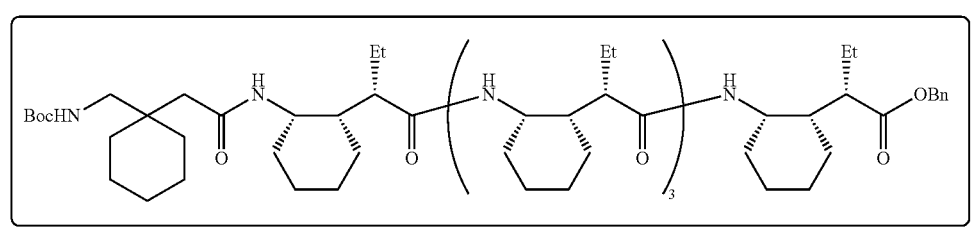

Boc-Gabapentin-γ-γ-γ-γ-OH (50 mg, 0.053 mmol) was added directly to a solution of HCl.NH$_2$-γ-OBn (17 mg, 0.053 mmol), EDCI (13 mg, 0.068 mmol), DMAP (7 mg, 0.057 mmol), and DIEA (12 µL, 0.068 mmol) in DMF (1 mL). The resulting solution was stirred for five days at room temperature. The reaction mixture was diluted with EtOAc, washed with 1 M aqueous NaHSO$_4$ and then brine. The organic layer was collected and dried over MgSO$_4$, filtered and concentrated to give a residue that was purified via column chromatography eluting with EtOAc and hexanes to yield the desired product (32 mg, 51% yield) as a white solid. TLC R$_1$=0.68 (EtOAc/hexanes, v/v, 1:1). $^1$H NMR (300 MHz, CDCl$_3$) δ 7.77 (m, 2H), 7.49 (m, 2H), 7.38-7.19 (m, 5H), 5.74 (d, J=10.4 Hz, 1H), 5.32, 5.06 (AB, JAB=12.7 Hz, 2H), 4.91 (X of ABX, 1H), 4.48 (m, 1H), 4.19 (m, 3H), 4.10 (m, 1H), 3.37, 2.93 (AB of ABX, JAB=14.5 Hz, JAX=6.1 Hz, JBX=7.8 Hz, 2H), 2.75 (ddd, J=10.9, 8.6, 3.8 Hz, 1H), 2.26 (m, 2H), 2.13 (m, 3H), 2.09-1.02 (m, 75H), 0.87 (m, 15H); $^{13}$C NMR: (125.7 MHz, CDCl3) delta 176.86, 175.65, 174.48, 174.03, 170.75, 157.53, 137.35, 128.41, 128.21, 127.26, 80.01, 65.73, 50.78, 48.77, 48.70, 47.67, 47.09, 46.92, 46.12, 46.00, 41.26, 40.98, 40.84, 39.71, 38.37, 37.35, 34.49, 33.76, 33.06, 32.74, 32.51, 31.95, 31.54, 30.60, 29.72, 29.38, 28.35, 26.43, 26.31, 26.00, 25.75, 24.15, 23.91, 23.77, 23.72, 23.64, 23.41, 22.70, 21.51, 21.27, 20.69, 20.40, 20.19, 20.04, 14.13, 11.77, 10.74, 10.60, 9.73; HRMS m/z (ESI): calcd. for: C$_{71}$H$_{116}$N$_6$O$_9$Na [M+Na]+1219.8696. found 1219.8692.

γ-Peptide 7 (S,S,S SERIES):

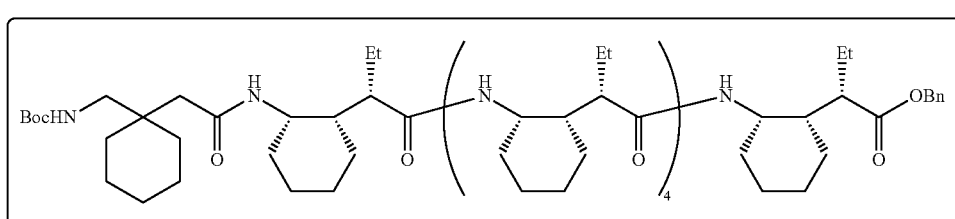

Boc-Gabapentin-γ-γ-γ-γ-γ-OH (23 mg, 0.021 mmol) was added directly to a solution of HCl.NH$_2$-γ-OBn (13 mg, 0.042 mmol), EDCI (5 mg, 0.025 mmol), DMAP (3 mg, 0.021 mmol), and DIEA (5 µL, 0.025 mmol) in DMF (1 mL). The resulting solution was stirred for five days at room temperature. The reaction mixture was diluted with EtOAc, washed with 1 M aqueous NaHSO$_4$ and then brine. The organic layer was collected and dried over MgSO$_4$, filtered and concentrated to give a residue that was purified via column chromatography eluting with EtOAc and hexanes to yield the desired product (14 mg, 51% yield) as a white solid. TLC R$_f$=0.69 (EtOAc/hexanes, v/v, 1:1). $^1$H NMR (300 MHz, CDCl$_3$) δ 7.93 (d, J=10.1 Hz, 1H), 7.71 (d, J=10.1 Hz, 1H), 7.66 (d, J=8.3 Hz, 1H), 7.49 (m, 2H), 7.41 (d, J 10.1 Hz, 1H), 7.35-7.19 (m, 4H), 5.81 (d, J=10.6 Hz, 1H), 5.31, 5.08 (AB, JAB=12.6 Hz, 2H), 4.89 (X of ABX, 1H), 4.49 (m, 1H), 4.23 (m, 3H), 4.13 (m, 2H), 3.34, 2.97 (AB of ABX, JAB=14.5 Hz, JAX=6.1 Hz, JBX=7.8 Hz, 2H), 2.81 (ddd, J=10.9, 8.3, 3.7 Hz, 1H), 2.37-1.07 (m, 92H), 1.00-0.80 (m, 18H); $^{13}$C NMR: (125.7 MHz, CDCl$_3$) δ 179.42, 178.35, 178.31, 177.92, 176.93, 176.73, 173.27, 160.00, 139.87, 130.99, 130.73, 129.80, 82.53, 68.29, 52.94, 51.31, 50.90, 50.23, 50.22, 49.69, 49.57, 49.05, 48.64, 48.59, 43.95, 43.54, 43.26, 42.03, 41.87, 40.56, 39.85, 36.93, 36.36, 36.34, 35.85, 35.72, 35.54, 35.10, 34.27, 33.42, 33.39, 30.89, 29.01, 28.86, 28.53, 28.48, 28.46, 28.27, 26.69, 26.34, 26.12, 25.82, 25.45, 25.41, 25.30, 25.18, 25.15, 24.03, 23.83, 23.20, 22.89, 22.88, 22.72, 22.68, 22.54, 14.28, 14.25, 14.21, 13.25, 12.99, 12.97, 11.96; HRMS (ESI): calcd. for: $C_{81}H_{133}N_7O_{10}Na$ [M+Na]$^+$ 1387.0070. found 1387.0096.

III. Crystal structures of γ-Peptides 3-7.

X-ray crystallography was used to investigate the conformational preferences of the γ-peptides we prepared. Five γ-peptides were crystallized that range in length from trimers to heptamers. The X-ray quality crystals were grown from various solvent mixtures by slow evaporation (Table 7-3).

TABLE 7-3

Crystallization conditions for γ-peptides 3-7.

| γ-peptide | Crystallization conditions | γ-peptide | Crystallization conditions |
|---|---|---|---|
| trimer 3 (R,R,R series) | Slow evaporation (EtOAc/hexanes) | hexamer 6 | Slow evaporation (CHCl$_3$/heptanes) |
| tetramer 4 | Slow evaporation (ClCH$_2$CH$_2$Cl/heptanes) | heptamer 7 | Slow evaporation (CHCl$_3$/heptanes) |
| pentamer 5 | Slow evaporation (ClCH$_2$CH$_2$Cl/heptanes) | | |

Scheme 7-6. Trimer 3, tetramer 4, and pentamer (S,S,S)-5.

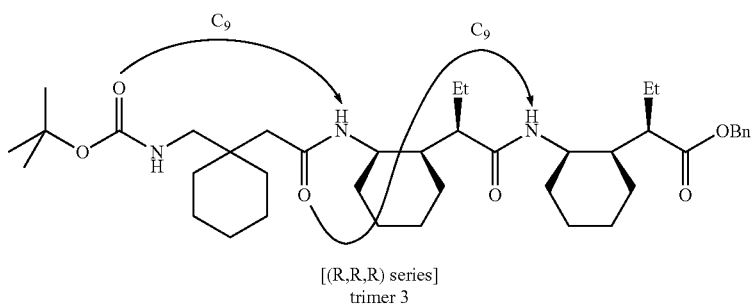

[(R,R,R) series]
trimer 3

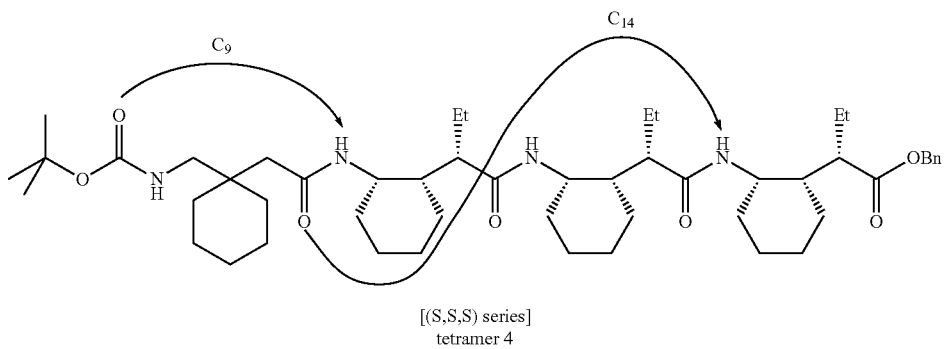

[(S,S,S) series]
tetramer 4

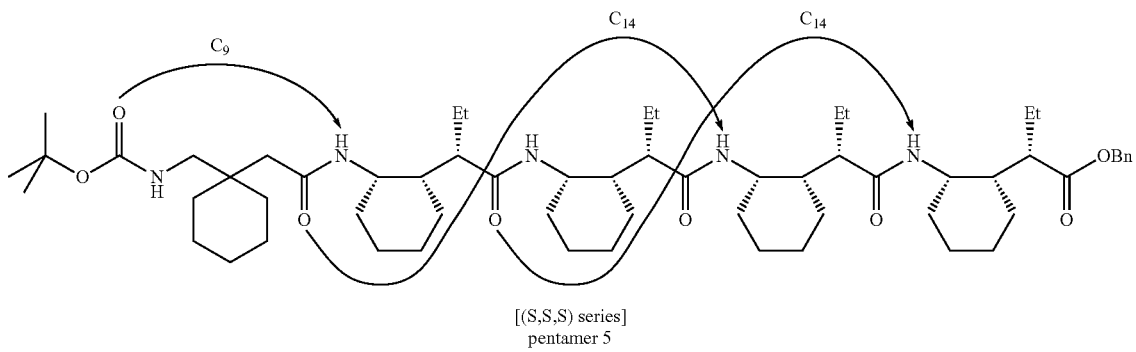

[(S,S,S) series]
pentamer 5

The X-ray crystallography structures of pentamer 5, hexamer 6 and heptamer 7 showed that each of the three molecules adopts an almost perfect 14-helical conformation in the segment containing γ-residues derived from 2. In addition, a $C_9$ H-bond was observed across the N-terminal gabapentin residue, which adopted torsion angles of opposite signs compared to γ-residues from 2. In each case the maximum number of 14-atom C=O(i)-H—N(i+3) H-bonds is formed in the segment containing γ-residues derived from 2, as illustrated below in Scheme 7-7 and 7-8.

of a full sphere to a resolution of 0.82 Å. A total of 59953 data were harvested by collecting 18 sets of frames with 0.6° scans in ω and φ with an exposure time 4-8 sec per frame. These highly redundant datasets were corrected for Lorentz and polarization effects. The absorption correction was based on fitting a function to the empirical transmission surface as sampled by multiple equivalent measurements. [Bruker-AXS. (2007) APEX2, SADABS, and SAINT Software Reference Manuals. Bruker-AXS, Madison, Wis., USA.]

Scheme 7-7. Hexamer 6.

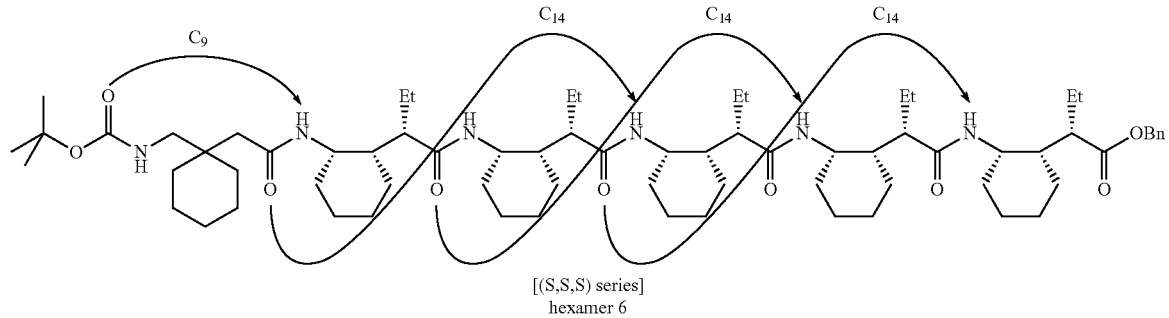

[(S,S,S) series]
hexamer 6

Scheme 7-8. Heptamer 7.

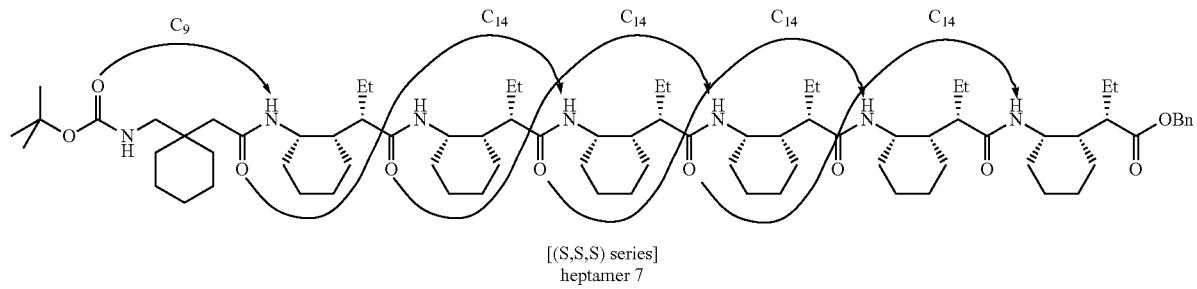

[(S,S,S) series]
heptamer 7

Data Collection.

A colorless crystal with approximate dimensions 0.54×0.32×0.29 mm3 was selected under oil under ambient conditions and attached to the tip of a MiTeGen MicroMount©. The crystal was mounted in a stream of cold nitrogen at 100(1) K and centered in the X-ray beam by using a video camera.

The crystal evaluation and data collection were performed on a Bruker SMART APEXII diffractometer with Cu $K_\alpha$ (λ=1.54178 Å) radiation and the diffractometer to crystal distance of 4.03 cm. Bruker SMART APEXII diffractometer with Cu Kα (λ=1.54178 Å) radiation and the diffractometer to crystal distance of 4.03 cm.

The initial cell constants were obtained from three series of ω scans at different starting angles. Each series consisted of 41 frames collected at intervals of 0.6° in a 25° range about ω with the exposure time of 4 seconds per frame. The reflections were successfully indexed by an automated indexing routine built in the APEXII program. The final cell constants were calculated from a set of 9121 strong reflections from the actual data collection.

The data were collected by using the full sphere data collection routine to survey the reciprocal space to the extent Structure Solution and Refinement.

The systematic absences in the diffraction data were uniquely consistent for the space group $P2_12_12_1$ that yielded chemically reasonable and computationally stable results of refinement. [Sheidrick, G. M. (2008) SHELXL. Acta Cryst. A64, 112-122; Dolomanov et al., J. Appl. Cryst. (2009) 42, 339-341; Guzei, I. A. (2006-2008); Internal laboratory computer programs "Inserter", "FCF_filter", "Modicifer".]

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms attached to carbons were included in the structure factor calculation at idealized positions and were allowed to ride on the neighboring atoms with relative isotropic displacement coefficients. The hydrogen atoms attached to nitrogen atoms were located in the difference map and refined independently with bond length restraints. There are three hydrogen bonding interactions of the type N—H...O present. The absolute configuration at atoms C15, C20, C21, C25, C30, and C31 was determined to be R.

The final least-squares refinement of 469 parameters against 7575 data resulted in residuals R (based on $F^2$ for I≥2σ) and wR (based on $F^2$ for all data) of 0.0302 and 0.0837, respectively. The final difference Fourier map was featureless. The molecular diagram was drawn with 50% probability ellipsoids.

Backbone Torsion Angle Analysis.

Table 7-4 compares backbone torsion angles for the gabapentin- and γ-residue 2 in oligomers 3-7 with analogous values of γ-residues from crystallographic analysis of gabapentin tetramer from Balaram et al. (Vasudev et al., *Angew. Chem. Int. Ed.* 2005, 44, 4972), and from the crystal structure of tetrapeptide containing $γ^{2,3,4}$-amino acid residues from Seebach et al. (Seebach et al., D.; *Chem. Commun.* 2001, 207). Each γ-residue I in trimer 3 displays a $g^-$, $g^-$ local conformation about the $C_α$-$C_β$ (ζ) and $C_β$-$C_γ$ (θ) bonds, and the gabapentin residue displays $g^+$, $g^+$. The local helical conformations for γ-residue 2 with S configurations deduced via crystallographic analysis for γ-peptides 4-7 feature opposite signs for the ζ and θ torsion angles ($g^+$, $g^+$), and opposite signs for the ψ and φ torsion angles. These values are consistent with values observed in the crystal structure of tetrapeptide for the 14-helical conformation from Seebach et al. The acyclic γ-residues in this case have absolute configurations analogous to that of (S,S,S)-γ-residue 2. Interestingly, the gabapentin residues in 4-7 adopt $g^-$, $g^-$ local conformations. The gabapentin adopts a C9 conformation despite the neighboring presence of a 14-helical segment. In γ-peptide containing gabapentin residues reported by Balaram, the signs of the four torsion angles between adjacent gabapentin residues are sometimes inverted (torsion angles ζ and θ for the residues 1 and 4 are opposite to that of residues 2 and 3) as shown in Table 7-4. This observation indicates that there is no preferred relation between the local fold of adjacent $C_9$ units on a gabapentin oligomer, and that such oligomers adopt a family of interconverting oligo-C9 conformations.

TABLE 7-4

Backbone Torsion Angles (deg) for the gabapentin/γ-peptides 3-7.

| Peptides | residues | φ | θ | ζ | ψ |
|---|---|---|---|---|---|
| trimer 3 (R,R,R SERIES) | gabapentin(1) | −95.6 | 71.0 | 74.8 | −93.3 |
| | γ(2) | 99.8 | −65.7 | −77.5 | 90.7 |
| | γ(3) | 137.2 | −50.8 | −49.3 | 119.3 |
| tetramer 4 (S,S,S SERIES) | gabapentin(1) | 90.9 | −71.2 | −76.1 | 78.4 |
| | γ(2) | −157.2 | 57.8 | 60.5 | −123.5 |
| | γ(3) | −162.2 | 66.0 | 67.9 | −134.9 |
| | γ(4) | −138.6 | 55.7 | 64.0 | −143.6 |
| pentamer 5 (S,S,S SERIES) | gabapentin(1) | 95.6 | −67.1 | −77.6 | 89.4 |
| | γ(2) | −159.6 | 54.1 | 48.6 | −115.0 |
| | γ(3) | −154.8 | 65.2 | 57.2 | −130.7 |
| | γ(4) | −144.0 | 57.9 | 64.0 | −135.5 |
| | γ(5) | −112.8 | 53.2 | 54.3 | −144.0 |
| hexamer 6 (S,S,S SERIES) | gabapentin(1) | 105.0 | −67.2 | −74.3 | 86.8 |
| | γ(2) | −146.5 | 52.6 | 60.2 | −122.0 |
| | γ(3) | −160.1 | 62.4 | 54.4 | −127.2 |
| | γ(4) | −148.5 | 60.0 | 61.2 | −128.8 |
| | γ(5) | −155.1 | 60.3 | 64.3 | −125.6 |
| | γ(6) | −131.6 | 61.5 | 66.5 | −140.9 |
| heptamer 7 (S,S,S SERIES) | gabapentin(1) | 102.7 | −63.3 | −78.9 | 75.5 |
| | γ(2) | −159.0 | 55.5 | 50.8 | −123.4 |
| | γ(3) | −148.6 | 64.0 | 58.1 | −132.7 |
| | γ(4) | −150.8 | 59.7 | 62.1 | −131.1 |
| | γ(5) | −152.9 | 62.1 | 60.7 | −123.6 |
| | γ(6) | −163.3 | 65.3 | 62.3 | −120.8 |
| | γ(7) | −134.6 | 57.4 | 55.8 | −118.3 |

TABLE 7-4-continued

Backbone Torsion Angles (deg) for the gabapentin/γ-peptides 3-7.

| Peptides | residues | φ | θ | ζ | ψ |
|---|---|---|---|---|---|
| γ-peptide 4.12 (gabapentin) | gabapentin(1) | 100.5 | −69.6 | −72.8 | 84.5 |
| | gabapentin(2) | −103.8 | 69.9 | 73.4 | −90.5 |
| | gabapentin(3) | −112.2 | 66.8 | 72.6 | −88.4 |
| | gabapentin(4) | 104.6 | −70.7 | −71.5 | 97.2 |
| γ-peptide 4.4 (R,R,R SERIES) ($γ^{2,3,4}$ amino acid) 14-helix | γ(1) | 114.3 | −68.7 | −52.4 | 151.2 |
| | γ(2) | 150.5 | −71.0 | −61.0 | 126.4 |
| | γ(3) | 156.4 | −61.7 | −50.5 | 123.3 |
| | γ(4) | 109.1 | 174.6 | −178.6 | 51.0 |

V. Calculation of Helical Parameters.

TABLE 7-5

14-Helical parameters calculated from four-residue segments in the crystal structures of 6 and 7.

| peptides | res/turn n | rise/turn P (Å) | rise/res d (Å) | radius r (Å) |
|---|---|---|---|---|
| hexamer 6 | 2.5 | 5.4 | 2.1 | 2.9 |
| heptamer 7 | 2.6 | 5.5 | 2.1 | 2.9 |
| | 2.5 | 5.5 | 2.2 | 2.9 |
| average | 2.5 | 5.5 | 2.1 | 2.9 |

Example 8. New Secondary Structures that Include γ-Amino Acid Residues

Figure 5A:
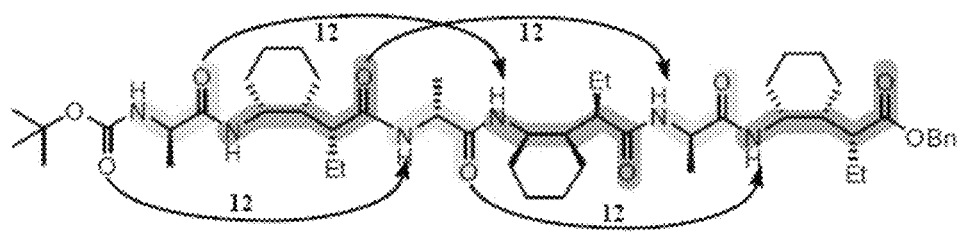

The studies described herein demonstrate that a variety of novel secondary structures of peptides that contain one or more γ-amino acids, such as compounds of the formulas described herein can now be prepared. These secondary structures include peptides that for a 12 Helix, a 13 Helix, and a 14 Helix. For example, as described above, a 1:1 α/γ-peptide, e.g., -α-γ-α-γ-α-γ-α-γ-, where the α is any α-amino acid and each γ is any γ-amino acid, such as AMCH or AMCP, can be prepared according to the methods described herein to provide a 12 Helix. A specific example is shown in FIG. 5A, formed from D-alanine and an (R,R,R)-γ-amino acid.

Figure 5B:
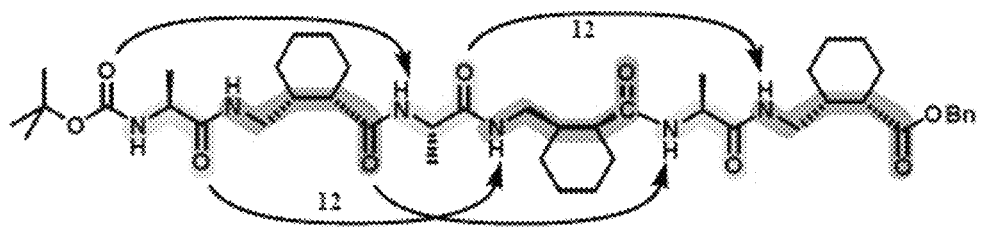

Other 12 Helix peptides can be prepared using L-α-amino acids and other γ-amino acids, such as those described in Examples 4 and 5 above. One example is the 12 Helix of FIG. 5B, which includes L-alanine and (1S,2R)-γ-amino acids residues. See also the compounds of Scheme 4-3 above.

Figure 5C:
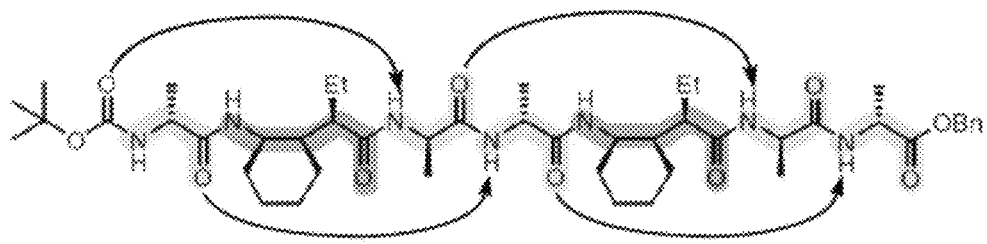

A 12 Helix can also be prepared using the γ-amino acids described herein by preparing a γαα-peptide, such as in FIG. 5C.

Figure 5D:
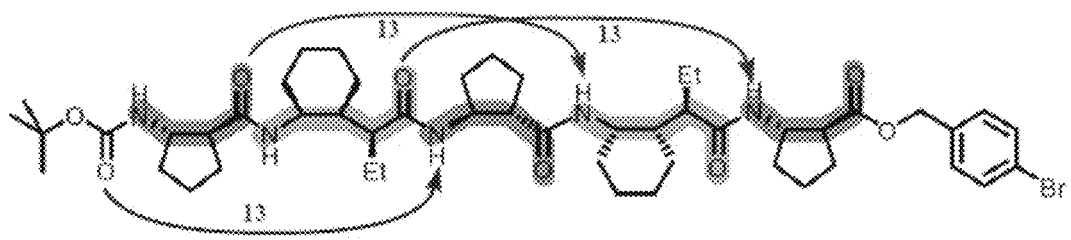

Novel secondary structures that include a 1:1 β/γ-peptides motif to achieve a 13 Helix. These peptides can also be prepared from one or more γ-amino acids, such as compounds of the formulas described, for example, such as AMCH or AMCP, or substituted variations thereof. An example of a 1:1 β/γ-peptides 13 Helix is shown in FIG. 5D. The 1:1 β/γ-peptides 13 Helix is a 1:1 β/γ-dipeptide that has the same number of atoms between the N- and C-terminus as an α-tripeptide, which is an important characteristic for foldamer analysis and protein design.

Peptides can also be formed from γ-amino acids to form a 14 Helix, such as the compound of Scheme 8-1.

Scheme 8-1. γ-Peptides-14 Helix.

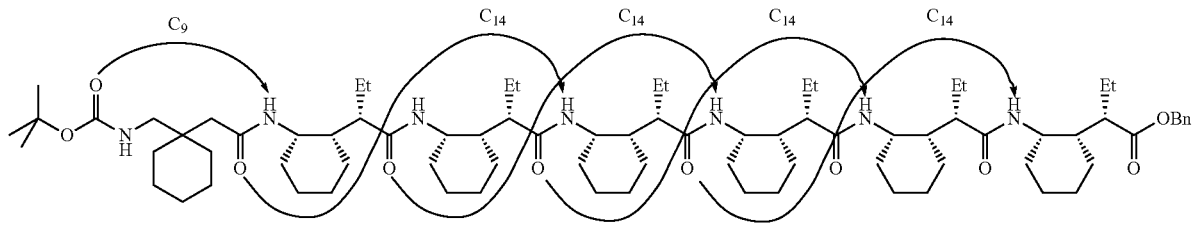

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of Formula V:

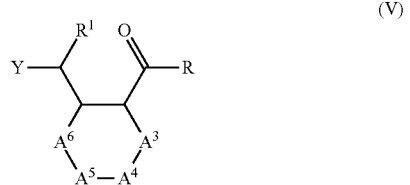

wherein
Y is $NO_2$ or NHA, wherein A is H, a nitrogen protecting group, an amino acid, or a chain of two or more amino acids;
R is H, an amino acid, a chain of two or more amino acids, or OB, wherein B is H or a carboxylic acid protecting group;
$R^1$ is alkyl, cycloalkyl, aryl, heteroaryl, or heterocycle; wherein the alkyl, cycloalkyl, aryl, heteroaryl, or heterocycle of $R^1$ is optionally substituted with one to five alkyl, alkoxy, fluoro, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups;
$A^3$ is carbon;
$A^4$ is carbon or nitrogen;
$A^5$ is carbon, or nitrogen provided that $A^6$ is not a direct bond;
$A^6$ is carbon, or a direct bond; and
each of $A^3$-$A^6$ are optionally substituted with one or two alkyl, alkoxy, halo, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups, or one nitrogen protecting group;
or a salt or solvate thereof.

2. A method of preparing a compound of Formula VI:

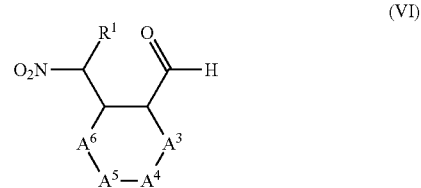

wherein
$R^1$ is hydrogen, alkyl, cycloalkyl, aryl, heteroaryl, or heterocycle; wherein the alkyl, cycloalkyl, aryl, heteroaryl, or heterocycle of $R^1$ is optionally substituted with one to five alkyl, alkoxy, fluoro, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups;
$A^3$ is carbon;
$A^4$ is carbon or nitrogen;
$A^5$ is carbon, or nitrogen provided that $A^6$ is not a direct bond;
$A^6$ is carbon, or a direct bond; and
each of $A^3$-$A^6$ are optionally substituted with one or two alkyl, alkoxy, halo, protected hydroxy, aryl, (aryl)alkyl, heteroaryl, heterocycle, cycloalkyl, alkanoyl, alkoxycarbonyl, protected amino, alkylamino, dialkylamino, acylamino, trifluoromethyl, trifluoromethoxy, carboxy, carboxyalkyl, keto, arylsulfonyl, cyano, or azide groups, or one nitrogen protecting group;
comprising contacting:
a compound of Formula VII:

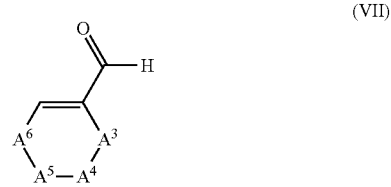

wherein $A^3$-$A^6$ are as defined for Formula VI; and
a compound of Formula VIII:

wherein $R^1$ is as defined for Formula VI;
in the presence of an organic solvent and a proline derivative, for a period of time sufficient to provide the compound of Formula VI, or a salt thereof.

3. The method of claim 2 wherein the contacting is carried out in the presence of a carboxylic acid, the proline derivative is a chiral pyrrolidine catalyst, and the compound of Formula VI is prepared in an enantiomerically enriched form.

4. The compound of claim 1, wherein Y is $NO_2$ or $NH_2$.

5. The compound of claim 1, wherein R is H or OH.

6. The compound of claim 1, wherein Y is $NO_2$ or $NH_2$ and R is H or OH.

7. The compound of claim 1, wherein $R^1$ is alkyl, cycloalkyl, aryl, heteroaryl, or heterocycle.

8. The compound of claim 7, wherein Y is $NO_2$ or $NH_2$.

9. The compound of claim 7, wherein R is H or OH.

10. The compound of claim 7, wherein Y is $NO_2$ or $NH_2$ and R is H or OH.

\* \* \* \* \*